US010711300B2

(12) United States Patent
Kamtekar et al.

(10) Patent No.: US 10,711,300 B2
(45) Date of Patent: Jul. 14, 2020

(54) METHODS AND COMPOSITIONS FOR DELIVERY OF MOLECULES AND COMPLEXES TO REACTION SITES

(71) Applicant: Pacific Biosciences of California, Inc., Menlo Park, CA (US)

(72) Inventors: Satwik Kamtekar, Mountain View, CA (US); Keith Bjornson, Fremont, CA (US); Leewin Chern, Fremont, CA (US); Steven Lin, Palo Alto, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 0 days.

(21) Appl. No.: 15/656,622

(22) Filed: Jul. 21, 2017

(65) Prior Publication Data
US 2018/0023134 A1    Jan. 25, 2018

Related U.S. Application Data

(60) Provisional application No. 62/365,630, filed on Jul. 22, 2016.

(51) Int. Cl.
| | | |
|---|---|---|
| *C12Q 1/68* | (2018.01) | |
| *C12Q 1/6874* | (2018.01) | |
| *G01N 27/447* | (2006.01) | |
| *G01N 33/487* | (2006.01) | |
| *C12Q 1/6834* | (2018.01) | |
| *G01N 30/88* | (2006.01) | |

(52) U.S. Cl.
CPC ......... *C12Q 1/6874* (2013.01); *C12Q 1/6834* (2013.01); *G01N 27/447* (2013.01); *G01N 33/48721* (2013.01); *G01N 2030/8827* (2013.01)

(58) Field of Classification Search
CPC ............ C12Q 2521/101; C12Q 1/6874; C12Q 1/6834; C12Q 2521/543; C12Q 1/6806; G01N 27/447; G01N 33/48721
See application file for complete search history.

(56) References Cited

U.S. PATENT DOCUMENTS

| | | |
|---|---|---|
| 5,001,050 A | 3/1991 | Blanco et al. |
| 5,034,506 A | 7/1991 | Summerton et al. |
| 5,198,543 A | 3/1993 | Blanco et al. |
| 5,235,033 A | 8/1993 | Summerton et al. |

(Continued)

FOREIGN PATENT DOCUMENTS

| | | |
|---|---|---|
| WO | WO 2007/041342 A2 | 4/2007 |
| WO | 2007075987 A2 | 7/2007 |

(Continued)

OTHER PUBLICATIONS

Albà, M. "Protein Family Review: Replicative DNA Polymerases" Genome Biology 2(1):reviews 3002.1-3002.4 (2001).

(Continued)

*Primary Examiner* — Betty J Forman
(74) *Attorney, Agent, or Firm* — Monicia Elrod-Erickson

(57) ABSTRACT

The present invention provides methods, compositions, and systems for distributing molecules and complexes into reaction sites. In particular, the methods, compositions, and systems of the present invention result in an active loading of molecules and complexes into reaction sites with improved efficiency over loading by passive diffusion methods alone.

20 Claims, 25 Drawing Sheets

(56) References Cited

U.S. PATENT DOCUMENTS

| | | |
|---|---|---|
| 5,328,824 A | 7/1994 | Ward et al. |
| 5,476,928 A | 12/1995 | Ward et al. |
| 5,576,204 A | 11/1996 | Blanco et al. |
| 5,867,266 A | 2/1999 | Craighead |
| 6,214,246 B1 | 4/2001 | Craighead |
| 6,438,279 B1 | 8/2002 | Craighead et al. |
| 6,635,163 B1 | 10/2003 | Craighead et al. |
| 6,753,200 B2 | 6/2004 | Craighead et al. |
| 6,917,726 B2 | 7/2005 | Levene et al. |
| 7,033,764 B2 | 4/2006 | Korlach et al. |
| 7,041,812 B2 | 5/2006 | Kumar et al. |
| 7,052,847 B2 | 5/2006 | Korlach et al. |
| 7,056,661 B2 | 6/2006 | Korlach et al. |
| 7,056,676 B2 | 6/2006 | Korlach et al. |
| 7,302,146 B2 | 11/2007 | Turner et al. |
| 7,315,019 B2 | 1/2008 | Turner et al. |
| 7,316,769 B2 | 1/2008 | Craighead et al. |
| 7,427,343 B2 | 9/2008 | Han et al. |
| 7,692,783 B2 | 4/2010 | Lundquist et al. |
| 7,715,001 B2 | 5/2010 | Lundquist et al. |
| 7,745,116 B2 | 6/2010 | Williams |
| 7,833,398 B2 | 11/2010 | Craighead et al. |
| 7,907,800 B2 | 3/2011 | Foquet et al. |
| 7,918,979 B2 | 4/2011 | Han et al. |
| 7,968,702 B2 | 6/2011 | Wegener et al. |
| 7,995,202 B2 | 8/2011 | Lundquist et al. |
| 8,153,375 B2 | 4/2012 | Travers et al. |
| 8,669,374 B2 | 3/2014 | Shen et al. |
| 8,802,600 B2 | 8/2014 | Rank et al. |
| 8,889,886 B2 | 11/2014 | Yue et al. |
| 8,906,612 B2 | 12/2014 | Shen et al. |
| 8,906,670 B2 | 12/2014 | Gray et al. |
| 8,906,831 B2 | 12/2014 | Eid et al. |
| 8,993,307 B2 | 3/2015 | Zaccarin et al. |
| 8,994,946 B2 | 3/2015 | McCaffrey et al. |
| 9,051,263 B2 | 6/2015 | Shen |
| 9,062,091 B2 | 11/2015 | Bjornson et al. |
| 9,223,084 B2 | 12/2015 | Grot et al. |
| 9,372,308 B1 | 6/2016 | Saxena et al. |
| 9,551,030 B2 | 1/2017 | Turner et al. |
| 9,624,540 B2 | 4/2017 | Lundquist et al. |
| 9,658,161 B2 | 5/2017 | Saxena et al. |
| 2003/0044781 A1 | 3/2003 | Korlach et al. |
| 2003/0124576 A1 | 7/2003 | Kumar et al. |
| 2003/0146145 A1* | 8/2003 | Krotz ........ B01D 67/003 210/243 |
| 2003/0215937 A1* | 11/2003 | Matson ........ B01J 19/0046 435/287.2 |
| 2004/0028613 A1* | 2/2004 | Quay ........ A61K 45/06 424/45 |
| 2005/0003399 A1* | 1/2005 | Blackburn ........ B82Y 15/00 435/6.11 |
| 2006/0141485 A1* | 6/2006 | Su ........ B01J 19/0046 435/6.11 |
| 2007/0036511 A1 | 2/2007 | Lundquist et al. |
| 2007/0072196 A1 | 3/2007 | Xu et al. |
| 2007/0196846 A1 | 8/2007 | Hanzel et al. |
| 2008/0032301 A1 | 2/2008 | Rank et al. |
| 2008/0108082 A1 | 5/2008 | Rank et al. |
| 2008/0176769 A1* | 7/2008 | Rank ........ B01J 19/0046 506/32 |
| 2009/0286245 A1 | 11/2009 | Bjornson et al. |
| 2009/0208957 A1 | 12/2009 | Travers et al. |
| 2009/0298075 A1 | 12/2009 | Travers et al. |
| 2010/0075332 A1 | 3/2010 | Patel et al. |
| 2010/0093555 A1 | 4/2010 | Bjornson et al. |
| 2010/0112645 A1 | 5/2010 | Clark et al. |
| 2010/0152424 A1 | 6/2010 | Korlach et al. |
| 2010/0167299 A1 | 7/2010 | Korlach |
| 2011/0059505 A1 | 3/2011 | Hanzel et al. |
| 2011/0189659 A1 | 8/2011 | Clark et al. |
| 2012/0014837 A1 | 1/2012 | Fehr et al. |
| 2012/0019828 A1 | 1/2012 | McCaffrey et al. |
| 2012/0021525 A1 | 1/2012 | Fehr et al. |
| 2012/0034602 A1 | 2/2012 | Emig et al. |
| 2012/0085894 A1 | 4/2012 | Zhong et al. |
| 2013/0217007 A1 | 8/2013 | Kamtekar et al. |
| 2013/0327644 A1 | 12/2013 | Turner et al. |
| 2014/0051068 A1 | 2/2014 | Cherf et al. |
| 2014/0094374 A1 | 4/2014 | Kamtekar et al. |
| 2014/0094375 A1 | 4/2014 | Kamtekar et al. |
| 2014/0318965 A1* | 10/2014 | Hayden ........ C12Q 1/6874 204/451 |
| 2015/0005202 A1 | 1/2015 | Gray |
| 2015/0050659 A1 | 2/2015 | Sebo et al. |
| 2015/0065353 A1 | 3/2015 | Turner et al. |
| 2015/0086994 A1 | 3/2015 | Williams et al. |
| 2015/0167071 A1 | 6/2015 | Bjornson et al. |
| 2016/0310926 A1 | 10/2016 | Sun et al. |
| 2017/0136433 A1 | 5/2017 | Sun et al. |
| 2017/0159119 A1 | 6/2017 | Sheikholeslami et al. |

FOREIGN PATENT DOCUMENTS

| | | |
|---|---|---|
| WO | 2007076057 A2 | 7/2007 |
| WO | WO 2007/075987 A2 | 7/2007 |
| WO | WO 2007/076057 A2 | 7/2007 |
| WO | 2007123763 A2 | 11/2007 |
| WO | WO 2007/123763 A2 | 11/2007 |
| WO | 2008051530 A2 | 5/2008 |
| WO | WO 2008/051530 A2 | 5/2008 |
| WO | 2009114182 A1 | 9/2009 |
| WO | WO 2009/114182 A1 | 9/2009 |
| WO | 2013096819 A2 | 6/2013 |
| WO | WO 2013/096819 A2 | 6/2013 |
| WO | 2013192106 A1 | 12/2013 |
| WO | WO 2013/192106 A1 | 12/2013 |
| WO | 2007041342 A2 | 4/2017 |

OTHER PUBLICATIONS

Anaspec, "TAT (47-57)," https://www.anaspec.com/products/product.asp?id=32173, Last accessed on Oct. 4, 2017, 2 pages.

Aoki A., "Microwell Cluster for Processing Electron Microscope Sections for Immunocytochemistry", Biotech. Histochem. 67: 98-9 (1992).

Burgers et al. "Eukaryotic DNA polymerases: proposal for a revised nomenclature" J Biol Chem. 276(47):43487-90 (2001).

Chen, T., et al., "Nature-Inspired Creation of Protein-Polysaccharide Conjugate and its Subsequent Assembly onto a Patterned Surface", 2003, Langmuir, 19(22):9382-9386.

Clackson et al. "Making antibody fragments using phage display libraries" Nature 352:624-628 (1991).

Crameri et al. "DNA shuffling of a family of genes from diverse species accelerates directed evolution" Nature 391:288-291 (1998).

Deng, T. et al., "Prototyping of Masks, Masters, and Stamps/Molds for Soft Lithography Using an Office Printer and Photographic Reduction", Anal. Chem. 72:3176-80 (2000).

Driscoll, R. J., et al., Atomic-Scale Imaging of DNA Using Scanning Tunneling Microscopy. Nature, 346(6281): 294-296 (1990).

Eid, J. et al., "Real-time DNA sequencing from single polymerase molecules", Science, 323(5910), 133-138 (2009).

Fairhead, M., et al., "SpyAvidin Hubs Enable Precise and Ultrastable Orthogonal Nanoassembly", J. Am. Chem. Soc., 136(35): 12355-12363 (2014).

Franklin, M. et al., Structure of the Replicating Complex of a Pol α Family DNA Polymerase, et al., Cell, vol. 105, 657-667, 2001.

Gibbs et al. "Degenerate oligonucleotide gene shuffling (DOGS): a method for enhancing the frequency of recombination with family shuffling" Gene 271:13-20 (2001).

Goodwin, P. M., et al., "Application of Single Molecule Detection to DNA Sequencing", Nucleosides & Nucleotides, 16(5-6): 543-550 (1997).

Han, J., et al., "Separation of Long DNA Molecules in a Microfabricated Entropic Trap array" Science, vol. 288(5468), p. 1026-1029 (May 12, 2000).

Hiraga and Arnold General method for sequence-independent site-directed chimeragenesis: J. Mol. Biol. 330:287-296 (2003).

(56) References Cited

OTHER PUBLICATIONS

Howorka, S., et al., "Sequence-Specific Detection of Individual DNA Strands using Engineered Nanopores", Nature Biotechnology, 19(7): 636-639 (2001).

Hübscher et al. "Eukaryotic DNA Polymerases" Annual Review of Biochemistry vol. 71: 133-163 (2002).

Kane et al., Patterning Proteins and Cells Using Soft Lithography, Biomaterials. 20: 2363-76 (1999).

Kim, E. et al., "Chitosan to Connect Biology to Electronics: Fabricating the Bio-Device Interface and Communicating Across this Interface", Polymers, 7:1-46 (2015).

Korlach et al. "Long, Processive Enzymatic DNA Synthesis Using 100% Dye-Labeled Terminal Phosphate-Linked Nucleotides", (2008) Nucleosides, Nucleotides and Nucleic Acids 27:1072-1083.

Korlach et al. "Selective Aluminum Passivation for Targeted Immobilization of Single DNA Polymerase Molecules in Zero-Mode Waveguide Nanostructures", (2008) PNAS U.S.A. 105(4):1176-1181.

Levene, et al., "Zero-mode waveguides for single-molecule analysis at high concentrations", Science 299:682-686, Jan. 2003.

Liu, A., et al., (2009), "*Nanocomposite Films Assembled from Genetically Engineered Filamentous Viruses and Gold Nanoparticles: Nanoarchitecture- and Humidity-Tunable Surface Plasmon Resonance Spectra*", Adv. Mater., 21: 1001-1005. doi:10.1002/adma.200800777.

Lundquist, P., et al., "Parallel Confocal Detection of Single Molecules in Real Time", Optics Letters, vol. 33, Issue 9, pp. 1026-1028.

Meijer et al. "Φ29 Family of Phages" Microbiology and Molecular Biology Reviews, 65(2):261-287 (2001).

Meller, A., et al., Rapid Nanopore Discrimination Between Single Polynucleotide Molecules, Proceedings of the National Academy of Sciences of the United States of America, 97(3): 1079-1084 (2000).

Nam, K. T., et al. "*Genetically Driven Assembly of Nanorings Based on the M13 Virus*" Nano Letters, 2004, 4 (1), pp. 23-27.

Rigler, et al., DNA-Sequencing at the Single Molecule Level, Journal of Biotechnology, 86(3): 161 (2001).

Seker, U., et al., "*Material binding peptides for nanotechnology*", Molecules. Feb. 9, 2011;16(2):1426-51. doi: 10.3390/molecules16021426.

Shi, X-W, et al., "*Chitosan Biotinylation and Electrodeposition for Selective Protein Assembly*", 2008, Macromolecular Bioscience, 8:451-457.

Steitz "DNA polymerases: structural diversity and common mechanisms" J Biol Chem 274:17395-17398 (1999).

Travers, K., et al., "*A Flexible and Efficient Template Format for Circular Consensus Sequencing and SNP Detection*", (2010) Nucl. Acids Res. 38(15):e159.

Wu, L-Q., et al., "*Voltage-Dependent Assembly of the Polysaccharide Chitosan onto an Electrode Surface*", Langmuir, 18:8620-8625 (2002).

Zhu, H., et al., "*Analysis of Yeast Protein Kinases Using Protein Chips*", Nature Genet. 26:283-9 (2000).

\* cited by examiner

FIG. 18A
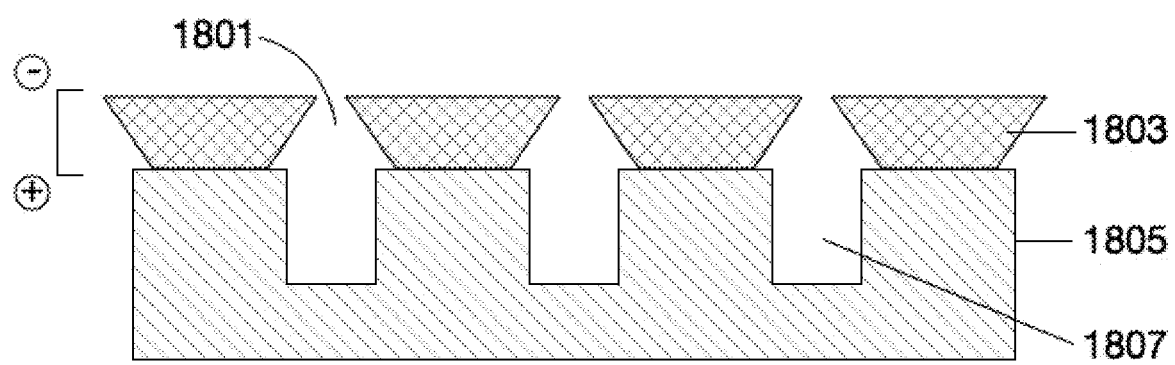
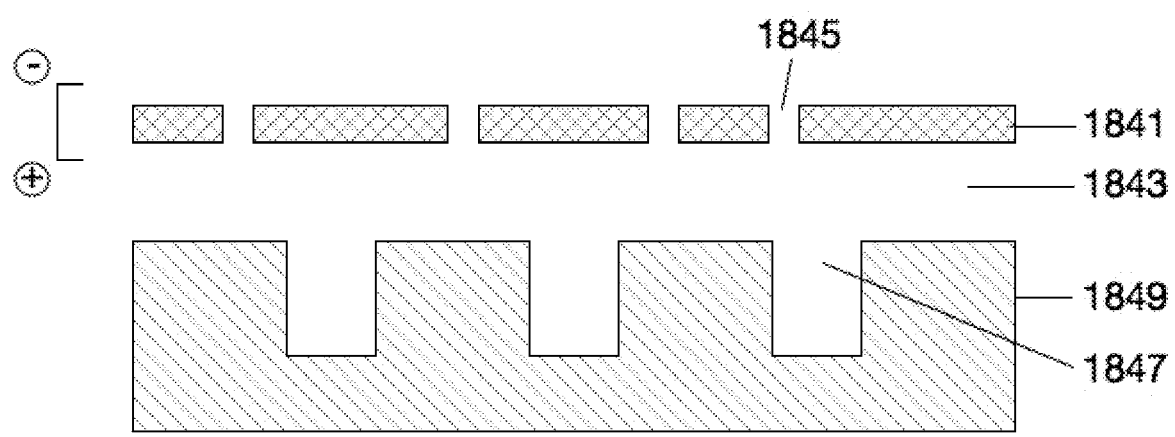
FIG. 18B

METHODS AND COMPOSITIONS FOR DELIVERY OF MOLECULES AND COMPLEXES TO REACTION SITES

CROSS-REFERENCE TO RELATED APPLICATIONS

The present application claims priority of U.S. Provisional Patent Application No. 62/365,630 filed Jul. 22, 2016, the entire contents of which is incorporated herein for all purposes by this reference.

BACKGROUND OF THE INVENTION

Techniques in molecular biology and molecular medicine often rely on analysis of single biological molecules. Such techniques include DNA and RNA sequencing, polymorphism detection, the detection of proteins of interest, the detection of protein-nucleic acid complexes, and many others. The high sensitivity, high throughput and low reagent costs involved in single molecule analysis make this type of analysis an increasingly attractive approach for a variety of detection and analysis problems in molecular medicine, from low cost genomics to high sensitivity marker analysis.

The small observation volumes often used for single molecule analysis methods are typically provided by immobilizing or otherwise localizing molecules of interest within an optical confinement reaction/observation region, such as an array of extremely small wells as in an array of Zero Mode Waveguides (ZMWs), and delivering molecules of interest (including for example, a template, primers, enzymes etc.,) to the reaction region. One difficulty in performing single molecule analyses occurs in loading the reaction/observation region of single molecule analysis devices with the molecules of interest (e.g., template or other analyte and/or enzyme). Entropic barriers to loading can be significant when attempting to load large reactant molecules into these nanoscale reaction sites.

While passive distribution methods are effective in ensuring that, in most cases, not more than a single template or enzyme (or other analyte) molecule is loaded in each observation/reaction volume in an array such as a ZMW array, it would be desirable to develop methods and compositions for increasing the efficiency and density of loading in such reaction sites. The present invention provides these and other features that will be apparent upon complete review of the following.

SUMMARY OF THE INVENTION

Accordingly, the present disclosure provides methods, compositions, and systems for distribution of molecules of interest into reaction sites. In particular, the methods, compositions, and systems described herein result in an active loading of molecules of interest into reaction sites, resulting in an increased density of loading and/or increased efficiency of loading than is seen with passive diffusion methods alone.

In one aspect, the present disclosure provides a method of delivering a molecule to a site that includes the steps of: (a) providing a tethering nucleic acid at the site, where at least a portion of the tethering nucleic acid is located outside of the site and the tethering nucleic acid includes (i) a first strand comprising a capture moiety at a position that is located outside of the site, and (ii) a second strand; (b) exposing the tethering nucleic acid to a molecule comprising a binding moiety, where the binding moiety and the capture moiety interact to attach the molecule to the tethering nucleic acid; (c) degrading the second strand of the tethering nucleic acid, where the first strand contains self-complementary regions that hybridize together to collapse the first strand into a hairpin, and the collapse of the first strand further serves to carry the attached molecule into the interior of the site, thereby delivering the molecule to the site. In some embodiments, the capture moiety includes biotin and the binding moiety includes streptavidin. In further embodiments, the second strand includes RNA, and in yet further embodiments the second strand includes at least one deoxyuridine (dU).

In further embodiments and in accordance with the above, the first strand is resistant to exonuclease, and the second strand is sensitive to exonuclease, and the degrading step (c) includes applying an exonuclease to the tethering nucleic acid.

In further embodiments and in accordance with any of the above, the molecule is a member selected from the group consisting of: a template nucleic acid, a polypeptide, an antibody, and a small molecule. In still further embodiments, the molecule is part of a complex. In yet further embodiments, the molecule includes a template nucleic acid complexed with a polymerase enzyme. In still further embodiments, the complex further comprises a primer hybridized to the template nucleic acid. In yet further embodiments, the binding moiety is associated with the polymerase enzyme.

In further embodiments and in accordance with any of the above, the tethering nucleic acid includes capture moieties at both ends. In further embodiments, the capture moieties at the two ends are identical or are different.

In further embodiments and in accordance with any of the above, the tethering nucleic acid is immobilized to the site by an interaction between a capture moiety at one end and an appropriate binding moiety on the site.

In further embodiments and in accordance with any of the above, the tethering nucleic acid is at least 1000 nucleotides in length.

In further embodiments and in accordance with any of the above, the site includes a nanoscale well. In still further embodiments, the site is at the base of a nanoscale well. In some embodiments, the site includes a nanopore.

In further embodiments and in accordance with any of the above, the second strand does not include a capture moiety.

In further embodiments and in accordance with any of the above, the method further includes step (d) immobilizing the molecule to the site. In still further embodiments, the immobilizing includes an interaction between a first reaction moiety on the site and a second reaction moiety on the molecule.

In further embodiments and in accordance with any of the above, the second strand includes RNA and the degrading step includes applying RNAse.

In further embodiments and in accordance with any of the above, the capture moiety includes a scaffold, and the scaffold includes (i) a core with conjugation adaptors and (ii) multiple arms with biotin moieties. In still further embodiments, the arms include oligonucleotides. In yet further embodiments, the oligonucleotides are about 25 to about 250 or 50-100 basepairs (bp) in length.

In one aspect, the present disclosure provides a method of delivering molecules to an array of nanoscale wells that includes the steps of: (a) providing a surface including a plurality of nanoscale wells, where each of the nanoscale wells includes an immobilized tethering nucleic acid molecule; (b) distributing molecules to the surface, such that the tethering nucleic acid molecules are able to encounter and capture at least one molecule, where that capture increases effective concentration of the at least one molecule to the openings of the nanoscale wells to favor loading of the nanoscale wells with the at least one molecule, thus delivering molecules to the array of nanoscale wells. In further embodiments, the nanoscale wells further include polymerases that process the tethering nucleic acid molecules such that their captured molecules are drawn into the nanoscale wells. In still further embodiments, the tethering nucleic acid molecule is of sufficient length to have at least a portion protruding outside the nanoscale well, for example about 1000 nucleotides in length. In yet further embodiments, the processing proceeds until the captured molecules are themselves immobilized in the nanoscale wells, and in some further embodiments, the captured molecules are immobilized through an interaction between a moiety on the captured molecules and a moiety in the nanoscale wells.

In further embodiments and in accordance with any of the above, the molecules are a member selected from the group consisting of: a template nucleic acid, a polypeptide, an antibody, and a small molecule.

In further embodiments and in accordance with any of the above, the template nucleic acids include a 5' overhang and the tethered nucleic acid molecules include a 3' overhang, such that the capture of the template nucleic acids is by hybridization of matching overhangs between the tethered nucleic acid molecules and the template nucleic acids.

In further embodiments and in accordance with any of the above, the molecules are part of complexes. In still further embodiments, the molecules include template nucleic acid complexed with a polymerase enzyme. In yet further embodiments, a primer is hybridized to the template nucleic acid. In further embodiments, a binding moiety is associated with the polymerase enzyme, and that binding moiety can include in further embodiments streptavidin. In some embodiments, the polymerase enzyme is maintained in a stalled state until the molecules are delivered into the nanoscale wells.

In further embodiments and in accordance with any of the above, there is a cleavable linker between the tethering nucleic acid and the surface.

In further embodiments and in accordance with any of the above, the method further includes step (c) applying a protease to the nanoscale wells to release the tethering nucleic acid molecules.

In further embodiments and in accordance with any of the above, the tethering nucleic acid molecules comprise a double stranded nucleic acid in which the 3' end of one strand is linked to the 5' end of the other strand with a hairpin oligonucleotide.

In some aspects, the present disclosure provides a method of delivering template nucleic acid monomers to an array of nanoscale wells that includes the steps of: (a) providing a surface that has a plurality of nanoscale wells, where each of the nanoscale wells includes an immobilized tethering nucleic acid molecule; (b) distributing a first plurality of template nucleic acid monomers to the surface under conditions for ligation of the template nucleic acid monomers to the tethering nucleic acid molecules to form ligated sequencing templates; (c) processing the ligated sequencing templates, thus delivering the ligated sequencing templates into the interior of the nanoscale wells. In some embodiments, the tethering nucleic acid molecule is of sufficient length to have at least a portion protruding outside the nanoscale well. In further embodiments, the nanoscale wells further include polymerases that act during the processing step (c) such that the ligated sequencing templates are drawn into the nanoscale wells.

In further embodiments and in accordance with any of the above, the tethering nucleic acid molecules are at least about 1000 to about 5000 nucleotides in length.

In further embodiments and in accordance with any of the above, the method further includes a step of distributing a second plurality of template nucleic acid monomers to the ligated sequencing templates to attach additional monomers to the ligated sequencing templates. In still further embodiments, the method includes distributing a desired number of additional pluralities of template nucleic acid monomers to form ligated sequencing templates that comprise concatemers of the distributed monomers. In yet further embodiments, prior to each distributing of additional pluralities of template nucleic acid molecules, linker molecules are ligated to the end of each ligated sequencing template to designate the end of one monomer and the start of the next monomer, and those linker molecules may in some embodiments include an oligonucleotide of known sequence. In yet further embodiments, the concatemers have a length greater than 10 kb.

In further embodiments and in accordance with any of the above, the nanoscale wells further include polymerase enzymes, and the processing is accomplished by the activity of the polymerase enzymes.

In further embodiments and in accordance with any of the above, the ligated sequencing templates further include a hairpin loop at one end.

In further embodiments and in accordance with any of the above, the tethering nucleic acid molecules are immobilized to the base of the nanoscale wells through association with a polymerase immobilized at the base. In still further embodiments, the polymerase is maintained in an inactive state until processing step (c).

In further embodiments and in accordance with any of the above, the linker molecules are distributed to the surface along with the template nucleic acid monomers, and the linker molecules and the template nucleic acid monomers have complementary overhangs, to form ligated sequencing templates that comprise concatemers of the monomers separated by the linkers.

In some aspects, the present disclosure provides a method of immobilizing reactants at the base of nanoscale wells that includes the steps of: (a) providing an array that includes (i) a plurality of nanoscale wells, (ii) a solution layer above the nanoscale wells; and (iii) a conducting layer that allows exposure of cathodes at or near the base of each nanoscale well; (b) providing capture molecules to the array, where the capture molecules have a pKa near neutral pH and are water soluble in their protonated form and insoluble in their deprotonated form; (c) attaching the reactants to the capture molecules; and (d) applying voltage through an anode in the solution to selectively deposit the capture molecules onto the bases of the nanoscale wells, thereby immobilizing reactants to the bases of the nanoscale wells. In further embodiments, the capture molecules include chitosan. In still further embodiments, the reactants include polymerase enzyme complexes, which in further embodiments can include a polymerase enzyme associated to a template nucleic acid which is optionally hybridized to a primer. In some embodiments, step (c) is performed before step (b). In some embodiments, step (c) is performed after step (d).

In further embodiments and in accordance with any of the above, the method further includes step (e) exposing the nanoscale wells to an aqueous solution with pH less than 4 in order to remove the capture molecules and reactant to prepare the nanoscale wells for delivery of a new set of capture molecules.

In further aspects, the present disclosure provides a method of immobilizing reactants at the base of nanoscale wells that includes the steps of: (a) providing an array that includes (i) a plurality of nanoscale wells; (ii) a solution layer above the nanoscale wells; and (iii) a conducting layer that allows exposure of anodes at or near the base of each nanoscale well; (b) providing capture molecules to the array, where the capture molecules are water soluble in their charged form and insoluble in their uncharged form; (c) attaching the reactants to the capture molecules; and (d) applying voltage through a cathode in the solution to selectively deposit the capture molecules onto the bases of the nanoscale wells, thereby immobilizing reactants to the bases of the nanoscale wells.

In further aspects, the present disclosure provides a method of delivering template nucleic acids to nanoscale wells that includes the steps of: (a) providing an array of nanoscale wells; (b) providing an array of chambers over the array of nanoscale wells, where the chambers have narrower openings than the nanoscale wells; (c) applying a solution that contains template nucleic acids to the array of chambers; (d) applying pressure or voltage to the solution to drive the template nucleic acids into the chambers; (e) allowing the template nucleic acids to passively diffuse from the chambers into the nanoscale wells, thereby delivering template nucleic acids to nanoscale wells. In some embodiments, the array of chambers includes a cathode, and the voltage applied in step (d) is through an anode in the solution. In further embodiments, the array of chambers is designed such that the chambers align with the nanoscale wells. In still further embodiments, the nanoscale wells further include polymerase enzymes. In yet further embodiments, the upper openings of the chambers are narrower than the openings of the nanoscale wells.

In some aspects, the present disclosure provides a method of delivering template nucleic acids to nanoscale wells that includes the steps of: (a) providing an array of nanoscale wells, where a fluid-filled chamber is located above the array of nanoscale wells; (b) providing a loading screen to the top of the fluid-filled chamber where the loading screen includes randomly placed holes; (c) applying a solution with template nucleic acids to the loading screen; (d) applying pressure or voltage to the solution to drive the template nucleic acids into the fluid-filled chamber through the holes of the loading screen; (e) allowing the template nucleic acids to passively diffuse from the fluid-filled chamber into the nanoscale wells, thereby delivering template nucleic acids to nanoscale wells. In some embodiments, the nanoscale wells are about 50 nm in diameter. In further embodiments, the randomly placed holes are about 30 to about 75 nm in diameter. In yet further embodiments, the template nucleic acids are from about 5 kb to about 20 kb in length. In still further embodiments, the nanoscale wells further include polymerase enzymes.

In some aspects, the present disclosure provides method of delivering polymerase enzyme complexes to nanoscale wells that includes the steps of: (a) providing a surface that includes an array of nanoscale wells; (b) coating the surface with a positively charged peptide to form a coated surface; (c) applying a composition with polymerase enzyme complexes to the coated surface such that at least a portion of the polymerase enzyme complexes attach to the positively charged peptides; (d) releasing the polymerase enzyme complexes from the positively charged peptides or polypeptides to allow the polymerase enzyme complexes to passively diffuse into the nanoscale wells, thereby delivering polymerase enzyme complexes to the nanoscale wells. In some embodiments, the releasing step includes applying a solution containing high salt to the coated surface. In some embodiments, the releasing step includes applying trypsin to the coated surface. In some embodiments, the releasing step includes applying a size exclusion resin to the coated surface.

In further embodiments and in accordance with any of the above, the positively charged peptide or polypeptide is a member selected from the group consisting of Tat, poly-lysine, poly-arginine, and histone.

In further embodiments and in accordance with any of the above, the polymerase enzyme complexes include polymerase enzymes attached to template nucleic acid molecules. In still further embodiments, the template nucleic acid molecules are further hybridized to a primer. In yet further embodiments, the template nucleic acid molecules are at least 5 kb long or are about 3 kb to about 20 kb in length.

In further embodiments and in accordance with any of the above, the delivering of the polymerase enzyme complexes is accomplished about 4 to about 100 times faster than seen with diffusion loading alone.

In further embodiments and in accordance with any of the above, the delivering of the polymerase enzyme complexes is accomplished at least 30, 40, 50, 60, 70 or 80 times faster than seen with diffusion loading alone. In still further embodiments, the delivering of the polymerase enzyme complexes is accomplished about 30 to about 150 times faster than seen with diffusion loading alone. In yet further embodiments, the delivering of the polymerase enzyme complexes is accomplished about 20 to about 80 times faster than seen with diffusion loading alone.

In some aspects, the present disclosure provides a method of delivering template nucleic acids to nanoscale wells that includes the steps of: (a) providing an array of nanoscale wells; (b) providing at least one channel over the array of nanoscale wells, wherein the at least one channel comprises regions of greater and lesser confinement; (c) applying a solution containing template nucleic acids to the at least one channel; (d) applying a driving force to the solution to move the template nucleic acids through the channel over the nanoscale wells, where the regions of greater confinement serve as entropic barriers to delay or substantially prevent progress of the template nucleic acids along the channel; (e) allowing the template nucleic acids to passively diffuse from the at least one channel into the nanoscale wells, thus delivering template nucleic acids to nanoscale wells. In further embodiments, the regions of greater confinement are located near the nanoscale wells, such that the entropic barriers posed by the regions of greater confinement serve to enrich the concentration of the template nucleic acids over the nanoscale wells. In yet further embodiments, the driving force includes an electrical potential or hydrodynamic pressure.

In further embodiments and in accordance with any of the above, the regions of greater and lesser confinement are alternately spaced along the channel.

In further embodiments and in accordance with any of the above, the region of greater confinement has a depth of between about 5 nm and about 500 nm, about 2 nm and about 100 nm, or about 30 nm and about 50 nm.

In further embodiments and in accordance with any of the above, the applying step (d) comprises a first phase and a second phase, where the first phase includes a high driving force to load the template nucleic acids into the channel and the second phase includes reducing the driving force to collect the template nucleic acids at or near the entropic barriers.

In further embodiments and in accordance with any of the above, the template nucleic acids are complexed with a polymerase enzyme in polymerase enzyme complexes that are delivered to the nanoscale wells. In still further embodiments, the complexes further include a primer hybridized to the template nucleic acid. In yet further embodiments, the method further includes the step of immobilizing the complexes to the bottom of the nanoscale wells, and in still further embodiments, that immobilizing includes an interaction between a first reaction moiety on the bottom and a second reaction moiety on the polymerase enzyme or template nucleic acid.

In further embodiments and in accordance with any of the above, the at least one channel includes a number of channels equal to the number of columns of nanoscale wells that are present in the array.

In further embodiments and in accordance with any of the above, the method includes a step (f) analyzing the template nucleic acids located within the nanoscale wells.

BRIEF DESCRIPTION OF THE DRAWINGS

FIG. 18A-FIG. 18B is a schematic illustration of exemplary configurations of devices for use in electrophoretic loading techniques, in side view.

DETAILED DESCRIPTION OF THE INVENTION

Figure 1:
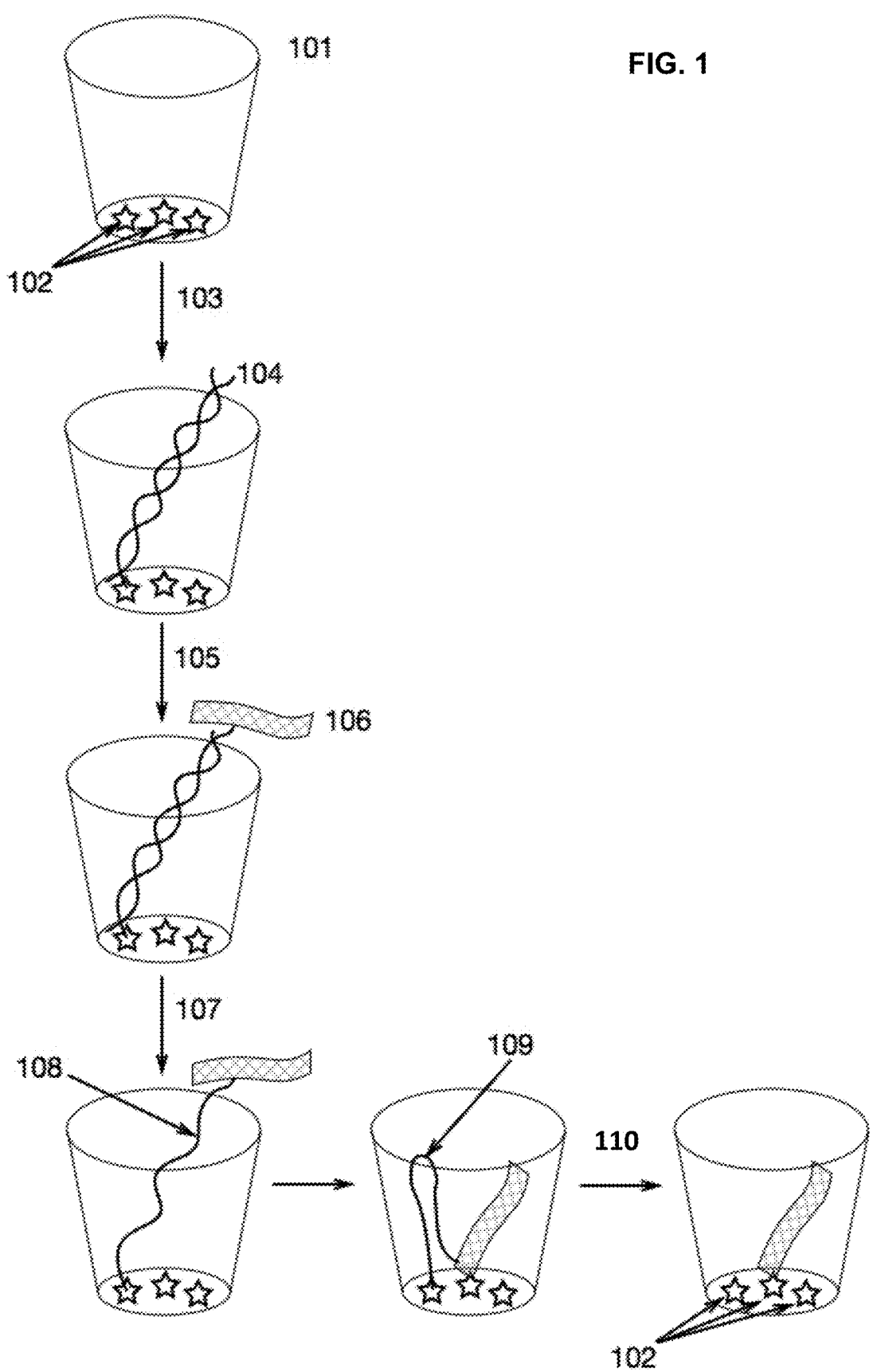
FIG. 1 is a schematic illustration of a loading method that utilizes helix drive mechanisms.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, phage display, and detection of hybridization using a label. Specific illustrations of suitable techniques can be had by reference to the examples herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), Stryer, L. (1995) *Biochemistry* (4th Ed.) Freeman, N.Y., Gait, "*Oligonucleotide Synthesis: A Practical Approach*" 1984, IRL Press, London, Nelson and Cox (2000), *Lehninger, Principles of Biochemistry* $3^{rd}$ Ed., W. H. Freeman Pub., New York, N.Y. and Berg et al. (2002) *Biochemistry*, $5^{th}$ Ed., W. H. Freeman Pub., New York, N.Y., all of which are herein incorporated in their entirety by reference for all purposes.

Note that as used herein and in the appended claims, the singular forms "a," "an," and "the" include plural referents unless the context clearly dictates otherwise. Thus, for example, reference to "a polymerase" refers to one agent or mixtures of such agents, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, compositions, formulations and methodologies which are described in the publication and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this invention. Accordingly, it is intended that the methods and compositions can include additional steps and components (comprising) or alternatively including steps and compositions of no significance (consisting essentially of) or alternatively, intending only the stated method steps or compositions (consisting of).

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". The term "about" also includes the exact value "X" in addition to minor increments of "X" such as "X+0.1" or "X−0.1." It also is to be understood, although not always explicitly stated, that the reagents described herein are merely exemplary and that equivalents of such are known in the art.

By "nucleic acid" or "oligonucleotide" or grammatical equivalents herein means at least two nucleotides covalently linked together. A nucleic acid of the present invention will generally contain phosphodiester bonds, although in some cases, nucleic acid analogs are included that may have alternate backbones, comprising, for example, phosphoramide, phosphorothioate, phosphorodithioate, and peptide nucleic acid backbones and linkages. Other analog nucleic acids include those with positive backbones; non-ionic backbones, and non-ribose backbones, including those described in U.S. Pat. Nos. 5,235,033 and 5,034,506. The template nucleic acid may also have other modifications, such as the inclusion of heteroatoms, the attachment of labels, such as dyes, or substitution with functional groups which will still allow for base pairing and for recognition by the enzyme. The length of a nucleic acid can be indicated in either nucleotides (measured on one strand of a single or double stranded nucleic acid) or base pairs (measured on both strands of a nucleic acid that is or that can be double stranded if hybridized to a complementary strand); units of nucleotides and base pairs thus can be used interchangeably to refer to an identical length, as will be clear to one skilled in the art.

As used herein, a "substantially identical" nucleic acid is one that has at least 80%, 85%, 90%, 95%, 96%, 97%, 98% or 99% A sequence identity to a reference nucleic acid sequence. The length of comparison is preferably the full length of the nucleic acid, but is generally at least 20 nucleotides, 30 nucleotides, 40 nucleotides, 50 nucleotides, 75 nucleotides, 100 nucleotides, 125 nucleotides, or more.

I. Overview

The active loading methods described herein enhance the loading of sites (also referred to herein as "reaction regions" and "array regions" and "nanoscale wells") with an active mechanism that serves to overcome entropic barriers that can be encountered by such molecules entering a site, particularly the entropic barriers that large molecules encounter during loading into confined sites, for example when large template nucleic acids (e.g., larger than 5 kb) are loaded into nanoscale wells. For ease of discussion, the loading methods described herein will often refer to arrays of nanoscale wells. Such nanoscale wells can in certain examples be zero mode waveguides (ZMWs), and in further examples, those ZMWs may have biotionylated bases and passivated sides, which can be of use in the methods of loading described herein as well as in later downstream applications, such as sequencing reactions. As will be appreciated, any discussion herein referring to nanoscale wells and/or ZMWs is applicable to any form of reaction sites and encompass all types of surfaces, shapes and configurations of regions into which molecules of interest can be loaded. These active loading methods provide the advantages of reducing the amount of input molecules needed for effective loading, reducing time required for loading, and/or reducing background noise for downstream reactions (such as sequencing reactions) by enriching for the molecules of interest, thus increasing performance (for example, for enriched loading of polymerases and polymerase complexes, downstream sequencing reactions show increased yield, readlength and accuracy).

For any of the methods described herein, the molecule of interest being delivered can be any molecule, including without limitation a template nucleic acid, a polypeptide, an antibody, and a small molecule. In certain examples, the molecule is a complex—for example, a polymerase associated with a template nucleic acid and optionally a primer hybridized to the template nucleic acid. For the ease of discussion, much of the discussion provided herein refers to molecules of interest, but as will be appreciated, any of the descriptions provided herein that refers to a molecule or molecules are equally applicable to a complex or complexes.

In some examples, the methods described herein utilize the ability of self-complementary nucleic acids to form hairpin structures—this "helix drive" mechanism allows any molecules associated with those self-complementary nucleic acids to be drawn along as the hybridization between complementary regions occurs. In general, these mechanisms involve the use of a tethering nucleic acid that is located at a reaction site. The tethering nucleic acid is double stranded, and at least one of the strands includes self-complementary regions. One of the strands (which contains self-complementary regions) includes at least one capture moiety at one or both ends—that capture moiety can associate with a molecule of interest. Once the molecule of interest is attached to that strand through interaction with that capture moiety, the other (second) strand (the one without the capture moiety) is removed using methods known in the art, including for example enzymatic degradation, leaving the first strand attached to the molecule of interest. The self-complementary regions of the first strand then hybridize to each other, forming a hairpin—the formation of the more closed and compact configuration of that hairpin serves to draw the attached molecule of interest closer into the reaction site and thus delivers the molecule of interest to the reaction site. The molecule of interest may in some examples then be immobilized to the reaction site for further processing.

In some examples, the methods described herein utilize "guidewires" to guide molecules of interest into the reaction site. In general, such reaction sites include nanoscale wells such as ZMWs. In general, the guidewire comprises a linear molecule immobilized in a nanoscale well. The nanoscale well can be part of a surface comprising an array of such nanoscale wells. The immobilized linear molecule has a length that allows it to interact with molecules of interest that are distributed to the surface and through that interaction capture at least one of those molecules. The immobilized linear molecule may be long enough to protrude outside of the nanoscale well, or it may be of sufficient length to reach partway up the height of the nanoscale well. The linear molecule may capture the molecules of interest by any mechanisms known in the art, including through electrostatic interactions, specific binding moieties, or any other binding pairs. That capture increases the effective concentration of the molecules of interest at the opening of the nanoscale well, resulting in an improved loading efficiency of those molecules into the nanoscale wells than is seen with passive diffusion alone. In further embodiments, the linear molecule is processed in order to draw the linear molecule (and its captured molecule(s) of interest) into the nanoscale well. That processing may involve any mechanism that serves to physically bring the end of the linear molecule that is attached to the molecule of interest into closer proximity to the point at which the linear molecule is immobilized in the well (in specific examples, to the base of the well). Once the molecule of interest is inside the well, it can in further embodiments be immobilized in the well in turn. In specific embodiments, the processing does not involve the use of a motor protein.

In some examples, the methods described herein utilize a "winching" or "fishing" mechanism to guide molecules of interest into the reaction site. These methods include the use of a tethering nucleic acid molecule immobilized in the reaction site, which can be a nanoscale well. As in the guidewire methods described herein, the tethering nucleic acid molecule may be long enough to protrude outside of the nanoscale well, or it may be of sufficient length to reach partway up the height of the nanoscale well. In these winching methods, a plurality of template nucleic acid monomers is distributed under conditions that allow for the ligation of those template nucleic acid monomers to the tethering nucleic acid molecules. Those ligated molecules can then be processed to draw the molecule into the nanoscale wells. The processing may include any method that serves to physically bring the ligated molecules into the wells—in certain examples, the processing includes the use of a polymerase enzymes within the nanoscale wells. The enzymes generate a nascent strand from the ligated molecules and by that method draw the ligated molecules into the wells. In further examples, prior to being processed to draw the molecules into the well, further pluralities of template nucleic acid monomers can be distributed to ligate additional monomers to the ends of the tethering nucleic acid. Any number of monomers can be so distributed, resulting in a ligated molecule that comprises a concatemer of the monomers distributed. The monomers making up that concatemer may be identical to each other, or they may be different. The concatemers may further include intervening linker molecules to designate the end of one monomer and the start of the next.

In some examples, the methods described herein utilize a mechanism in which a capture molecule is delivered to a reaction site through the use of electrodeposition. Such mechanisms include the use of a capture molecule that is water soluble and charged at one pH and water insoluble and uncharged at another pH. Thus, changing pH and applying a voltage differential can drive the capture molecule (and any associated molecules, such as template nucleic acids, polymerases, and/or complexes containing both a template nucleic acid and a polymerase) to a reaction region site. In further examples, these electrodeposition methods are used to immobilize reactants at the base of nanoscale wells. In such examples, the nanoscale wells may be part of an array. These arrays may further include a solution layer above the wells as well as a conducting layer that allows exposure of cathodes at or near the base of each nanoscale well. Capture molecules are provided to the array, and those capture molecules will in certain examples have a pKa near neutral pH. In some examples, the capture molecules are water soluble in their protonated form and insoluble in their deprotonated form. Reactants can be attached to the capture molecules, and a voltage applied through an anode in the solution layer to selectively deposit the capture molecules onto the bases of the nanoscale wells, thus immobilizing the attached reactants to the bases of the nanoscale wells. As will be appreciated, this configuration can be altered for capture molecules based on their pKa, such that the voltage differential is produced by using a cathode in the solution layer and having the conducting layer that allows exposure of anodes at or near the base of the nanoscale wells.

In some examples, the methods described herein utilize a mechanism in which template nucleic acids or similarly charged molecules are delivered to a reaction site through the application of pressure or voltage. In one example, the reaction sites are overlaid by an array of chambers such that the chambers line up directly with the reaction sites. Voltage or pressure is used to drive molecules into the chambers. Then, because the reaction sites will typically have larger openings than the upper openings of the chambers, the molecules within the chambers are more likely to diffuse into the reaction site rather than out of the chambers. In another example, a fluid-filled chamber is located above the reaction sites, and a loading screen is provided to the top of the fluid-filled chamber, wherein the loading screen comprises randomly placed holes. A solution containing template nucleic acids is applied to the loading screen and then pressure or voltage is applied to the solution to drive the template nucleic acids into the fluid-filled chamber through the holes of the loading screen. The template nucleic acids then passively diffuse from the fluid-filled chamber into the nanoscale wells.

In some examples, the methods described herein utilize a mechanism involving affinity loading. In general, a surface containing reaction sites, such as nanoscale wells, is coated with a positively charged peptide. A composition containing molecules of interest containing negative charges (such as polymerase enzyme complexes) is applied to the coated surface such that at least a portion of the molecules attach to the positively charged peptides. The molecules are then released from the positively charged surface to allow the polymerase enzyme complexes to passively diffuse into the nanoscale wells.

Any of the above described methods may be used alone or in any combination with each other. In addition, any of the methods described herein may be used in any combination with Super Poisson loading methods and/or density loading methods known in the art and described for example in U.S. Pat. No. 8,906,831, U.S. Ser. No. 15/078,915, filed Mar. 23, 2016 and U.S. Ser. No. 62/257,152, filed Nov. 18, 2015, hereby incorporated by reference in their entirety for all purposes and in particular for all teachings related to methods and compositions for loading reaction sites, such as nanoscale wells, with molecules of interest, such as polymerase enzyme-template complexes.

The above aspects and further exemplary embodiments are described in further detail in the following discussion.

II. Helix Drive

In one aspect, the present disclosure provides methods of loading molecules onto sites by providing in the sites self-complementary single stranded tethering nucleic acids that are initially held in an un-collapsed linear double-stranded state such that at least a portion of that tethering nucleic acid is outside the site. The tethering nucleic acid will in general contain a capture moiety on one of the strands that is able to interact with a molecule of interest, generally through a binding moiety associated with that molecule of interest. This interaction between the tethering nucleic acid and the molecule of interest may be direct or indirect. The capture moiety on the tethering nucleic acid may directly interact with a binding moiety on the molecule of interest, or there may be an intervening entity through which the tethering nucleic acid associates with the molecule of interest. For example, as has been described herein, a molecule of interest in accordance with any of the methods described herein may be part of a complex. In an exemplary embodiment, the molecule of interest is a template nucleic acid that is complexed with a polymerase, and the polymerase is what comprises the binding moiety that then interacts with the capture moiety on the tethering nucleic acid to attach the complex to the tethering nucleic acid.

After attachment of the molecule to the tethering nucleic acid, the strand of the tethering nucleic acid that is not attached to the molecule (e.g., the strand that does not contain the capture moiety) is degraded, causing the remaining strand, which is self-complementary, to collapse into a large hairpin in which the ends are brought together. That movement of collapsing into the hairpin configuration serves to bring the tethering nucleic acid and its attached molecule into the reaction site.

FIG. 1 provides an exemplary illustration of the helix drive process. A reaction site 101 contains immobilization regions 102. In step (103), a tethering nucleic acid 104 is immobilized to the immobilization regions, generally via only one of the two strands. That same strand contains a capture moiety. Molecules of interest are distributed (105) such that at least one molecule of interest (106) interacts with that capture moiety to attach to that strand. The other strand of the tethering nucleic acid is removed (107), leaving the single tethering nucleic acid strand (108) attached to the molecule of interest (106). The single tethering nucleic acid strand contains self-complementary regions that cause the tether to fold into a hairpin shape (109), thus bringing the attached molecule into the interior of the reaction site. In further step(s) 110, the molecule of interest can be immobilized to the base of the reaction site, including in a further exemplary embodiment to an immobilization region 102. In further embodiments, the remaining tethering nucleic acid strand can be removed, leaving the molecule of interest in the reaction site. The two strands of the tethering nucleic acid are optionally different molecules as shown in FIG. 1, or can be part of the same molecule (e.g., a large hairpin or a circular nucleic acid). Although discussed for simplicity in terms of a single tethering nucleic acid per well or site, it will be evident that the well or site optionally includes multiple tethering nucleic acids.

In certain embodiments, the reaction site is a nanoscale well, and the molecule of interest is a complex containing a polymerase enzyme complexed with a template nucleic acid with a primer optionally also hybridized to the template nucleic acid. In embodiments in which the molecule is a template nucleic acid or a complex containing template nucleic acid, the template nucleic acid may comprise DNA, RNA, or a combination of both.

In certain embodiments the capture of the molecule of interest involves an interaction between a capture moiety on the tethering nucleic acid and a binding moiety on the molecule of interest. As will be appreciated, in embodiments involving complexes, the binding moiety may be located on any component of the complex—for example, for complexes containing a polymerase enzyme and a template nucleic acid, the binding moiety may be on the template nucleic acid or on the polymerase enzyme. The capture moiety on the tethering nucleic acid and the binding moiety on the molecule of interest may comprise any pair that can react with each other, including without limitation antigen-antibody binding pairs, receptor-ligand binding pairs, aptamer-epitope binding pairs, GST/glutathione pairs, nucleic acid hybridization pairs, and the like. In specific embodiments, the capture moiety and the binding moiety comprise biotin and streptavidin respectively (or vice versa). It will be evident that avidin, traptavidin, neutravidin, or other known biotin-binding moieties can be substituted for streptavidin wherever streptavidin is specified herein.

In certain embodiments, the tethering nucleic acid contains capture moieties on both ends of the strand that is not degraded. That capture moiety may be any member of the pairs described above. In specific embodiments, the capture moiety is a biotin, and the binding moiety on the molecule of interest is streptavidin. In further embodiments, the reaction site also contains binding moieties, and the tethering nucleic acid is immobilized to the reaction site through an interaction between the capture moiety on one end and the binding moiety on the reaction site. In some embodiments, the capture moieties on both ends of the tethering nucleic acid are identical. In some embodiments, the capture moieties on the two ends of the tethering nucleic acid are different from each other. In such embodiments, the tethering nucleic acid can be designed to have a polarity with respect to the reaction site, such that the capture moiety designed to pair with the molecule of interest is left free while the other end of the tethering nucleic acid is immobilized to the reaction site.

In some embodiments and in accordance with any of the above, the tethering nucleic acid is immobilized to a surface, generally a surface of a reaction site, including for example the base of a nanoscale well. In further embodiments, the immobilization to the surface is through any means of attachment, including the binding pairs discussed above or any other noncovalent or covalent attachment, electrostatic interaction, attachment through a linker or some other intervening molecule, or any other method by which the tethering nucleic acid molecule is connected to the reaction site.

In certain aspects, the collapsing of the tethering nucleic acid strand into a hairpin serves to bring the attached molecule of interest and/or complex close enough to the reaction site to allow the complex to become immobilized to the reaction site through any number of interactions, including covalent attachment, electrostatic interaction, attachment through a linker or some other intervening molecule, or any other method by which the molecule of interest is connected to the reaction site. In certain embodiments, the complex is immobilized to a reaction site using peptide linker systems, including for example SpyTag/SpyCatcher systems such as those described in for example Fairhead et al., (J. Am. Chem. Soc., 2014, 136: 12355-12363), which is hereby incorporated in its entirety for all purposes including all teachings related to assembling complexes utilizing SpyTag and SpyCatcher components. In an exemplary embodiment, streptavidin tetramers are used in which one of the four subunits bears the SpyTag and the SpyCatcher component is on the polymerase, although the reverse configuration can also be used. Similar constructs are further described in detail in Fairhead et al. For example, the base of a nanoscale well can bear biotin groups to which a SpyTagged streptavidin is bound. The nucleic acid tether can then be immobilized to the base of the well by binding to a biotin capture moiety on one end of the tether. A SpyCatcher-polymerase/template complex is captured by the other end of the tether and brought into the well, where the SpyCatcher fusion polymerase can react with the SpyTagged streptavidin, immobilizing the polymerase/template complex. In other embodiments, a biotinylated polymerase can be immobilized via streptavidin binding to a biotinylated site, e.g., the base of a nanoscale well.

In further embodiments, the tethering nucleic acid contains multiple capture moieties, thus increasing the points at which molecule(s) of interest can be captured and/or points at which the tethering nucleic acid can be immobilized to the reaction site. In some embodiments, the tethering nucleic acid includes a scaffold comprising multiple capture moieties. In further embodiments, the scaffold is a star-shaped scaffold. Generally, the core of the scaffold is a polymer, although any molecule or composition capable of attachment to multiple functional moieties may be used as the core. In certain non-limiting examples, the core of the scaffold is a multi-arm polyethylene glycol molecule or a DNA construct. In still further examples, the core of the scaffold is attached to multiple arms containing capture moieties that are able to interact with binding moieties on the molecule of interest. In some embodiment these arms comprise oligonucleotides that are about 25 to about 250, about 50 to about 100, about 75 to about 200 bp in length. Scaffolds of use with any of the tethering molecules described herein are described for example in U.S. Ser. No. 15/078,915, filed Mar. 23, 2016, which is hereby incorporated by reference in its entirety for all purposes and in particular for all teachings related to scaffold constructs and methods for binding molecules to same.

As discussed above, one part of the helix drive process is that the strand of the tethering nucleic acid that is not bound to the molecule of interest is degraded to allow the bound strand to collapse into a hairpin due to its self-complementary regions. That degradation of the unbound "second" strand can be accomplished by any method known in the art, including enzymatic degradation. The degradation method used will be determined by the design of the tethering nucleic acid, particularly the second strand. In general, the first strand bound to the molecule of interest is protected from degradation in some way and the second strand is designed to be sensitive. For example, if the first strand is resistant to exonuclease, and the second is sensitive (or is made sensitive at some point through treatment with a nickase, etc.), incubation with exonuclease would degrade the sensitive strand and generate the above-described hairpin. In further embodiments, the second strand comprises RNA and the first strand comprises DNA—the use of RNAse would then degrade the second strand while the first strand remains intact. In still further embodiments, the second strand contains dU (deoxyuridine)—in such embodiments, application of UDG (uracil-DNA glycosylase) followed by endonuclease VIII would result in selective degradation of the second strand. In other embodiments, the second strand contains deoxyinosine; in such embodiments, application of endonuclease V would result in selective degradation of the second strand.

In further embodiments and in accordance with any of the above, the molecule of interest that is captured by the tethering nucleic acid is a member selected from the group consisting of: a template nucleic acid, a polypeptide, an antibody, and a small molecule. In still further embodiments, the molecule is part of a complex. In yet further embodiments, the complex includes a template nucleic acid complexed with a polymerase enzyme and may optionally include a primer hybridized to the template nucleic acid.

In certain embodiments, the tethering nucleic acid molecule is of sufficient length to protrude outside of the reaction site. In embodiments in which the reaction site comprises a nanoscale well, this would mean that the tether is at or above the opening of the well. In other embodiments, the tethering nucleic acid molecule may not protrude outside of the reaction site, but nevertheless has sufficient length to interact with molecules that are in proximity to the reaction site. In further embodiments, the tethering nucleic acid is at least or about 500, 750, 1000, 1500, 2000, 2500, 3000, 3500, 4000, 4500, 5000, 5500, 6000, 6500, 7000, 7500, 8000, 8500, 9000, 9500, 10000 basepairs/nucleotides in length.

Any of the above-described helix drive loading methods may also be used for reaction sites that are nanopores. In such embodiments, the tethering nucleic acids are generally located proximal to the nanopore rather than directly inside the nanopore. Any of the above described methods for the helix drive process are applicable to use with reaction sites comprising nanopores.

In yet further embodiments, any of the helix drive loading methods described herein may be combined with other loading methods, including Super Poisson loading and density loading methods known in the art and described for example in U.S. Pat. No. 8,906,831, U.S. Ser. No. 15/078, 915, filed Mar. 23, 2016 and U.S. Ser. No. 62/257,152, filed Nov. 18, 2015, hereby incorporated by reference in their entirety for all purposes.

III. Guidewire

In one aspect, the present disclosure provides methods for active loading of molecules, including without limitation template nucleic acids and complexes that include template nucleic acids, into a reaction site that includes a "guidewire" to guide the desired molecule into the reaction site. In general, such reaction sites include nanoscale wells such as ZMWs.

Figure 2:
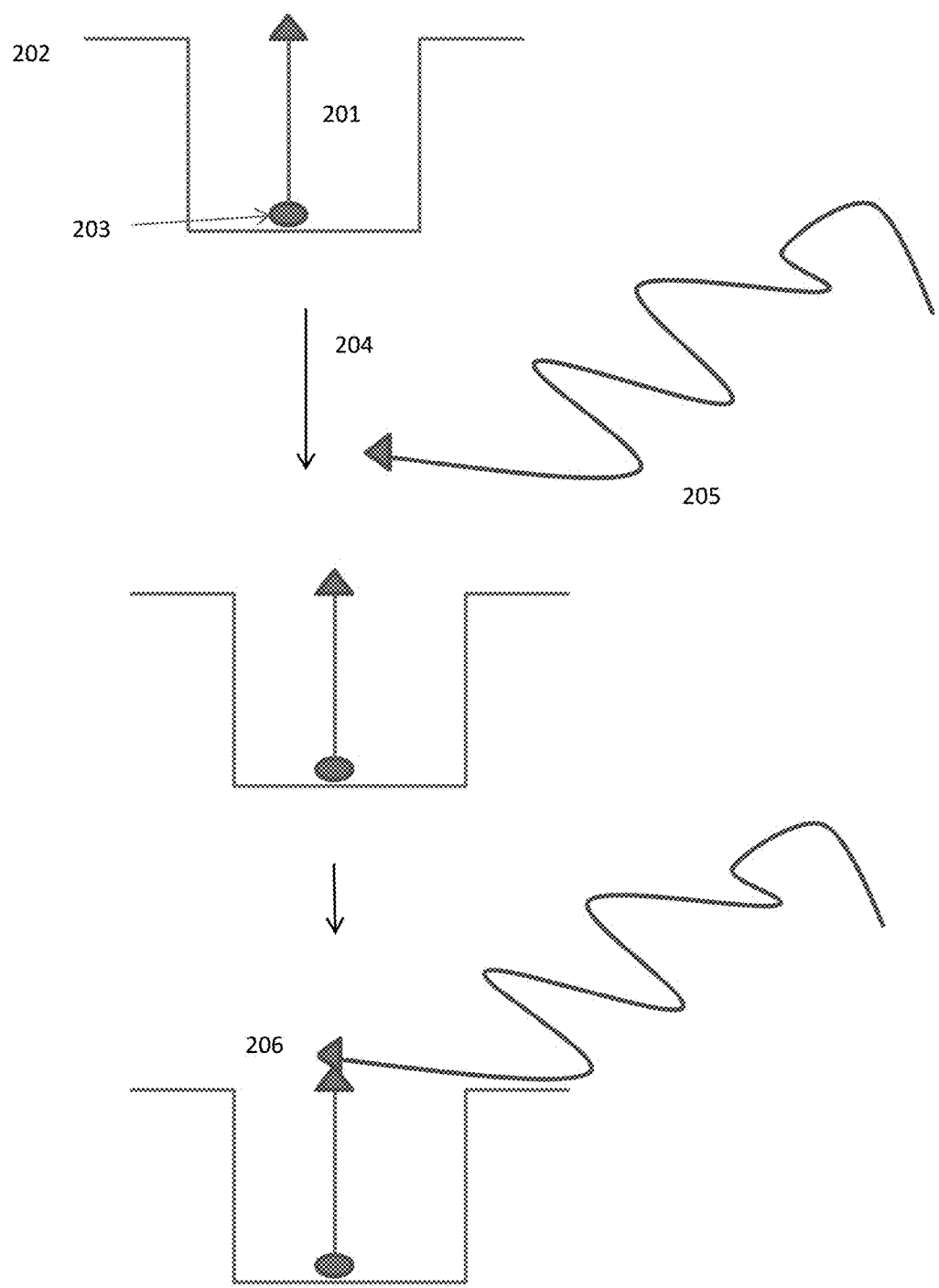
FIG. 2 is a schematic illustration of a loading method that utilizes guidewire mechanisms.

FIG. 2 provides a schematic illustration of an example of a method of loading utilizing a guidewire. In this exemplary aspect, the guidewire comprises a linear molecule (201) immobilized in a nanoscale well (202). The nanoscale well can be part of a surface comprising an array of such nanoscale wells. The immobilized linear molecule has a length that allows it to interact with molecules of interest (205) that are distributed to (e.g., disposed on the surface or in a solution disposed on the surface) (204) and capture at least one of those molecules (206). The immobilized linear molecule may be long enough to protrude outside of the nanoscale well, or it may be of sufficient length to reach partway up the height of the nanoscale well, e.g., when one end is immobilized at the base of the well (203). In further embodiments, the linear molecule has a length that is at least about 2×, 3×, 4×, 5×, 10×, 15×, 20×, 25×, 30×, 40×, 50× the height of the nanoscale well. In further embodiments, the linear molecule has a length that is at least about 3×, 4×, 5×, 10×, 15×, 20×, 25×, 30×, 40×, 50× the cross-sectional diameter of the linear molecule. The linear molecule may capture the molecules of interest by any mechanisms known in the art, including through electrostatic interactions, specific binding moieties, or any other binding pairs, including without limitation biotin-streptavidin binding pairs, antigen-antibody binding pairs, receptor-ligand binding pairs, aptamer-epitope binding pairs, GST/glutathione pairs, nucleic acid hybridization pairs, and the like. In embodiments in which the molecule of interest includes a template nucleic acid, the template nucleic acid may comprise a 5' overhang and the guidewires can comprise tethered nucleic acid molecules that comprise a 3' overhang, such that the capture of the template nucleic acids is by hybridization of matching overhangs between the tethered nucleic acid molecules and the template nucleic acids. In another example, the tethering nucleic acid is single-stranded or includes a single-stranded portion that hybridizes to a single-stranded portion of the template, e.g., to a hairpin loop in a SMRT-bell™ or other primarily double-stranded molecule. In other embodiments, the capture of the molecule of interest involves an interaction between a capture moiety on the guidewire and a binding moiety on the molecule of interest. As will be appreciated, in embodiments involving complexes, the binding moiety may be located on any component of the complex—for example, for complexes containing a polymerase enzyme and a template nucleic acid, the binding moiety may be on the template nucleic acid or on the polymerase enzyme.

Whatever mechanism of capture is used, the result is an increase in the effective concentration of the molecules of interest at or near the opening of the nanoscale well, resulting in an improved loading efficiency of those molecules into the nanoscale wells than is seen with passive diffusion alone. In further embodiments, the linear molecule is processed in order to draw the linear molecule (and its captured molecule(s) of interest) into the nanoscale well. That processing may involve any mechanism that serves to physically bring the end of the linear molecule that is attached to the molecule of interest into closer proximity to the point at which the linear molecule is immobilized in the well (in specific embodiments, at the base of the well). Once the molecule of interest is inside the well, it can in further embodiments be immobilized in the well in turn, e.g., at the base of the well. In specific embodiments, the processing does not involve the use of a motor protein.

In specific aspects, the guidewire comprises a tethering nucleic acid molecule immobilized in a nanoscale well, generally at the base of the well. In further aspects, each nanoscale well will have multiple guidewires/tethering nucleic acid molecules. The tethering nucleic acid may include without limitation a single stranded nucleic acid, a double stranded nucleic acid, or a partially double stranded and a partially single stranded nucleic acid. In specific embodiments, the tethering nucleic acid comprises DNA. In further specific embodiments, the tethering nucleic acid is a circular construct, such as those described in, e.g., U.S. Pat. No. 7,315,019 and U.S. patent application Ser. No. 12/220,674, filed Jul. 25, 2008, and alternate functional circular constructs as described in US Pat. App. Pub. No. 20090298075, the full disclosures of each of which are incorporated herein by reference in their entirety for all purposes and in particular for all teachings related to nucleic acid constructs. Briefly, such alternate constructs include template sequences that possess a central double stranded portion that is linked at each end by an appropriate linking oligonucleotide, such as a hairpin loop segment. In further embodiments, there is a cleavable linker between the guidewire and the point at which it is immobilized to the reaction site surface. In yet further embodiments, the guidewire methods described herein include a step of applying a composition to cleave the cleavable linker the guidewires once the molecules of interest have been successfully loaded into the reaction site and optionally immobilized. In specific embodiments, the cleavable linker includes a protease recognition site, and the guidewire is released by application of a protease to the reaction site. In further embodiments, the cleavable linkage may be part of the guidewire or a moiety on the guidewire. In one non-limiting example, the guidewire is immobilized to the reaction site through a streptavidin molecule, and the cleavage site is located within the streptavidin molecule itself.

As discussed above, in some embodiments, the tethering nucleic acid is long enough to protrude outside the well, whereas in some embodiments the tethering nucleic acid is shorter than the height of the nanoscale well. In embodiments involving an array of nanoscale wells, all the tethering nucleic acids may protrude outside the well, all the tethering nucleic acids may be shorter than the height of the nanoscale well, or there may be a mixture of protruding and shorter tethering nucleic acids.

Because they are generally small (around 1000 basepairs) and can be provided at relatively high concentration, the tethering nucleic acids can be loaded efficiently into the reaction sites. In certain embodiments, the tethering nucleic acids are from about 750 to about 4000 bp/nt in length. In further embodiments, the tethering nucleic acids are 1000-1500, 1000-2000, 1250-3500, 1500-3000, 1750-2000, 1000-5000 bp/nt in length. In still further embodiments, the tethering nucleic acids are at least or about 500, 750, 1000, 1500, 2000, 2500, 3000, 3500, 4000, 4500, 5000, 5500, 6000, 6500, 7000, 7500, 8000, 8500, 9000, 9500, 10000 bp/nt in length.

In certain embodiments, the tethering nucleic acid molecules are processed after capture of the molecules of interest to further draw the tethering nucleic acids and the captured molecules into the nanoscale wells. In an exemplary embodiment, the tethering nucleic acid molecule is processed by a polymerase enzyme (i.e., is employed as a template), and the act of the polymerase generating a nascent strand serves to draw the tethering nucleic acid molecule and its captured molecule into the nanoscale well where the polymerase is immobilized. In further embodiments, the processing proceeds until the captured molecules are themselves immobilized in the nanoscale wells using methods known in the art and described herein. In specific embodiments, the captured molecules are immobilized through an interaction between a moiety on the captured molecules and a moiety in the nanoscale wells.

As discussed herein, the molecules of interest can include any molecule including without limitation a template nucleic acid, a polypeptide, an antibody, and a small molecule, as well as complexes involving one or more of such molecules.

In an exemplary embodiment, the molecules of interest comprise template nucleic acids. In a further embodiment, the template nucleic acids are complexed with a polymerase and optionally are also hybridized to a primer. In certain embodiments, these complexes are maintained in an inactive or locked state. In embodiments in which the tethering nucleic acid is drawn into the nanoscale well by the processing action of a polymerase that is immobilized at the base of the well, maintaining the complex of interest in a locked state allows the polymerase at the base of the well to proceed without allowing the polymerase in the complex to begin its own reaction until needed (i.e., until the complex is brought into the nanoscale well). This locked state allows the complex to be loaded into the nanoscale well before it is activated for downstream reactions, particularly sequencing reactions—thus, the guidewire methods allow the surface to be properly loaded with the complexes prior to starting the reactions that allow generation of data such as sequencing data. In further embodiments, the locked state may be maintained by binding a complex including a modified recombinant polymerase with a nonhydrolyzable hexaphosphate analog (unlike nonhydrolyzable triphosphates, the hexaphosphate analog will generally not bind well to wild-type polymerase enzymes, such as those that would in further embodiments be used to process the tethering nucleic acid to bring it and its attached complex into the reaction site/nanoscale well; suitable modified polymerases are described hereinbelow).

Figure 13A:
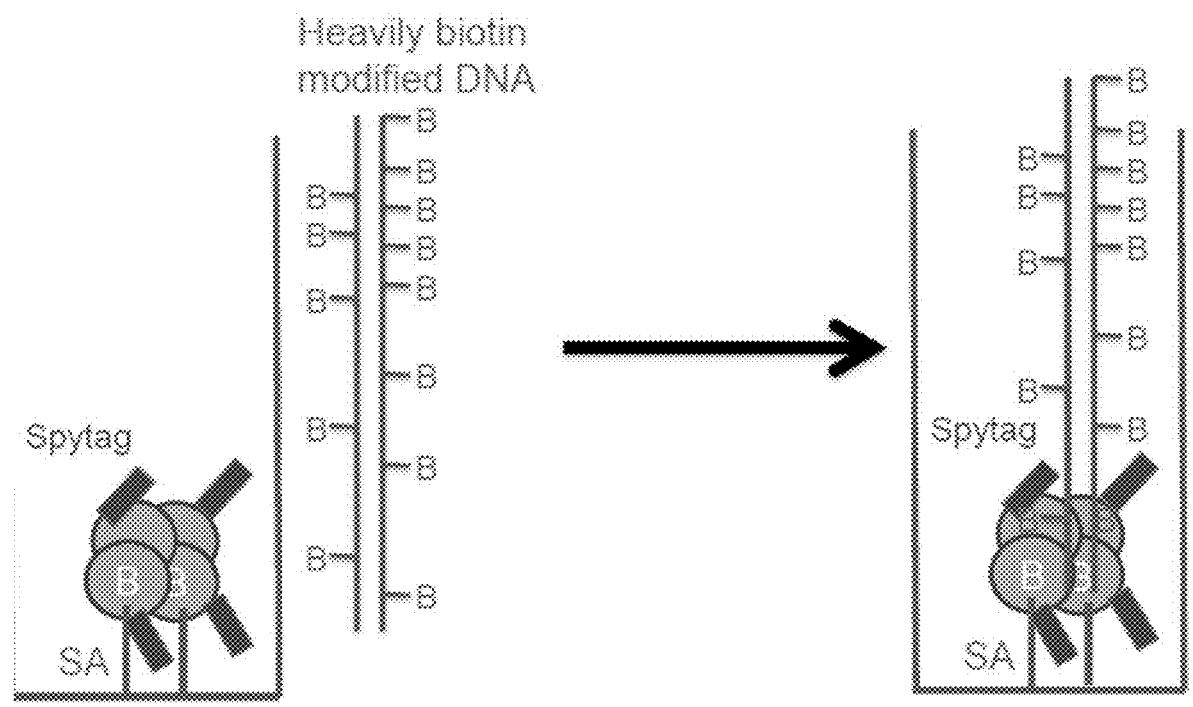
FIG. 13A-FIG. 13C is a schematic illustration of a loading method that utilizes guidewire mechanisms.
Figure 13B:
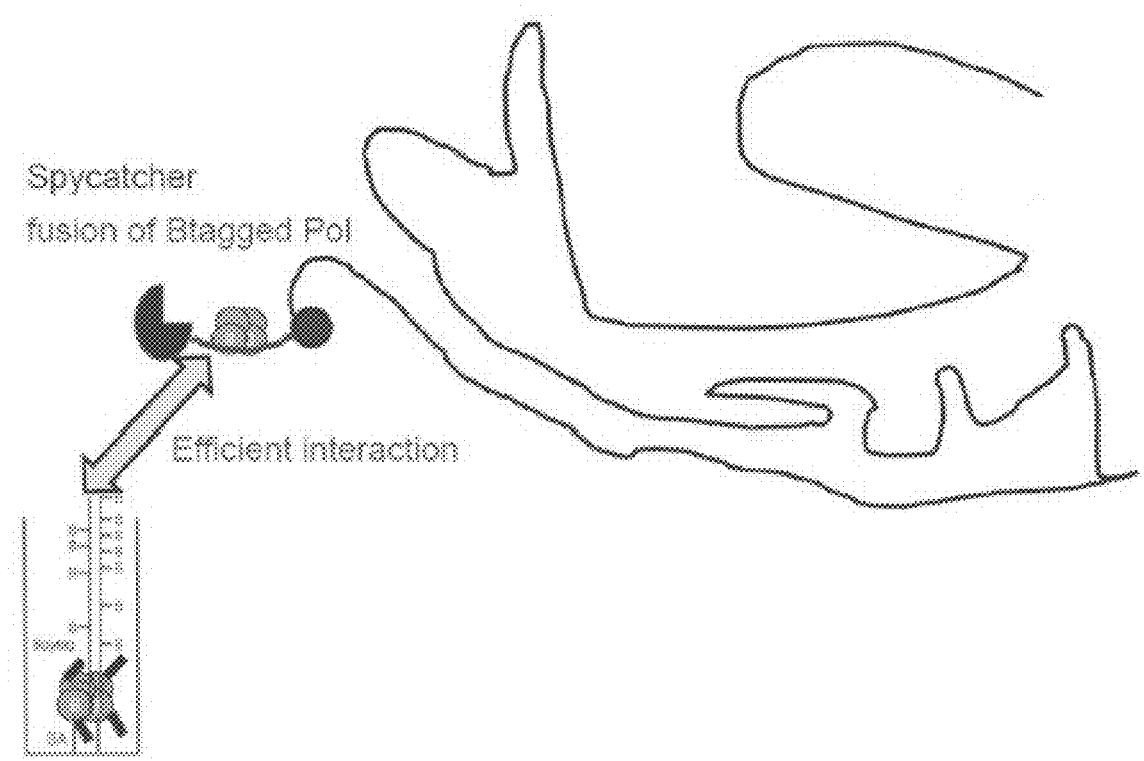
Figure 13C:
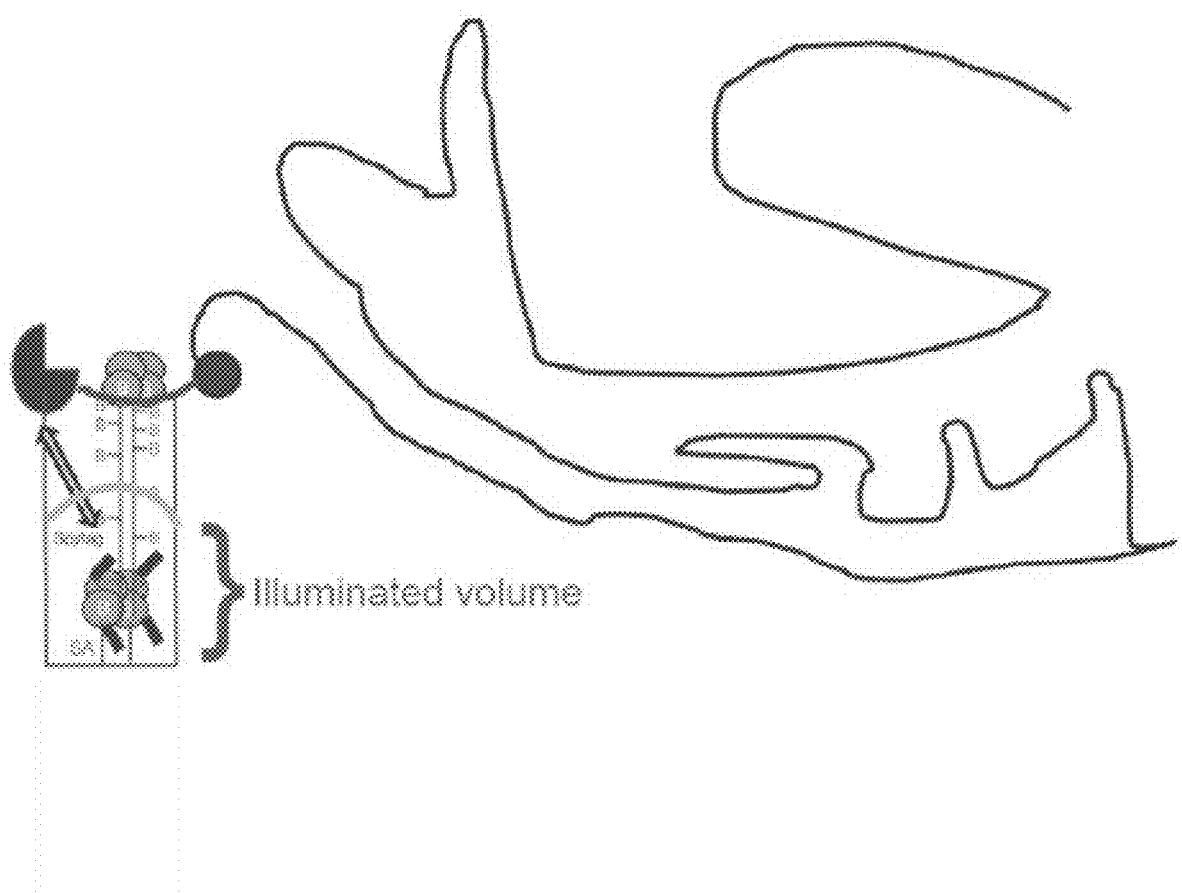

A specific embodiment of the guidewire method is illustrated in FIGS. 13A-C. The first step, shown in FIG. 13A, involves adding a heavily biotinylated duplex to a chip coated with spytag-streptavidin. Although one copy is shown, generally multiple biotinylated DNA molecules would be immobilized in a ZMW well. The second step shown in FIG. 13B involves binding a polymerase/nucleic acid complex containing a spycatcher/biotin-tagged polymerase fusion to the guidewire molecule, via streptavidin that binds to biotins both on the guidewire and on the spycatcher-polymerase fusion. As shown in FIG. 13C, the complex is now bound to the guidewire. Next spontaneous formation of the spycatcher-spytag bond immobilizes the polymerase and its bound template nucleic acid at the base of the ZMW, inside the illuminated volume.

In certain embodiments, the guidewire molecule is not a nucleic acid molecule. As will be appreciated, any molecule or composition that is able to capture a molecule of interest and guide it into the reaction site could be used in these guidewire mechanisms. In an exemplary embodiment, the guidewire/tether involves M13 phage particles. These particles are stiff rods that can be placed in a reaction site and have length to reach out of the reaction site (or at least to a height that allows interaction with distributed molecules of interest). Any M13 phage particles known in the art can be used in accordance with the methods described herein. In general, these particles are engineered to have affinity for the molecule of interest. For example, for capture of a template nucleic acid, M13 particles having a cationic peptide (e.g., tetraArg) fused to the major coat protein pVIII can be employed. Such particles have been described, e.g., in Liu et al., Adv. Mater. 2009, 21: 1001-1005, which is hereby incorporated in its entirety for all purposes and in particular for all teachings related to M13 phage particles. In some embodiments, the pill proteins at the tail are engineered to have streptavidin affinity, allowing immobilization of the M13 particles at a properly functionalized reaction site. In specific embodiments, the reaction site may be a nanoscale well in which the base has been functionalized with biotin, to which streptavidin can be bound. An M13 particle having a peptide with affinity for SA on pill has been described (see Nam et al. "Genetically Driven Assembly of Nanorings Based on the M13 Virus" Nano Letters, 2004, 4 (1), pp 23-27, which is hereby incorporated by reference in its entirety for all purposes). Thus in one exemplary embodiment for capture of a template/polymerase complex, an M13 particle having a cationic peptide, including without limitation tetraArg, fused to pVIII and a streptavidin binding peptide fused to pill is immobilized on the biotinylated, streptavidin coated base of a nanoscale well. The molecule of interest, generally a polymerase/template nucleic acid complex, is then added and captured by the particle. In another exemplary embodiment, M13 particles selected for affinity to a particular surface material, e.g., the silica bottom of a ZMW, and also bearing RRRR on pVIII are employed for capture of the template/polymerase complex. See also Seker et al., Molecules, 2011, 16: 1426-1461. In another exemplary embodiment, starting again with a nanoscale well functionalized at the base with biotin, streptavidin fused to a protein is bound to the biotin. The nanoscale well is then washed with M13 containing RRRR on the major coat protein pVIII and a peptide with affinity for the streptavidin-bound protein on pill, so the M13 becomes attached to the protein bound to the bottom of the well. The template/polymerase complex can then be added and will be captured to the RRRR sequence.

IV. Winching

In one aspect, the present disclosure provides methods for active loading of molecules, including without limitation template nucleic acids and complexes that include template nucleic acids, into reaction sites by utilizing "winching" or "fishing" lines that are used to capture the molecules of interest into the reaction sites. In general, such reaction sites can include without limitation nanoscale wells. The winching or fishing lines can include any type of molecule or polymer that can serve as a tether that can ligate to one or more molecules of interest and then undergo a processing step that draws the tether and its captured molecule(s) further into the interior of the reaction site. The winching or fishing lines may further be of a length to protrude outside of the reaction site, although in some embodiments the winching/fishing lines have a length sufficient to interact with distributed molecules of interest, but are not necessarily long enough to protrude outside the reaction site.

In an exemplary embodiment, these methods include the use of a tethering nucleic acid molecule immobilized in a nanoscale well. As in the guidewire methods described herein, the tethering nucleic acid molecule in the winching methods may be long enough to protrude outside of the nanoscale well, or it may be of a length to reach partway up the height of the nanoscale well. In specific embodiments, these methods are conducted using a surface comprising a plurality of nanoscale wells containing the immobilized tethering nucleic acid molecule. A plurality of template nucleic acid monomers is distributed under conditions that allow for the ligation of those template nucleic acid monomers to the tethering nucleic acid molecules. Those ligated molecules can then be processed to draw the molecule into the nanoscale wells. The processing may include any method that serves to physically bring the ligated molecules into the wells—in certain examples, the processing includes the use of polymerase enzymes within the nanoscale wells. The enzymes generate a nascent strand from the ligated molecules and by that method draw the ligated molecules into the wells.

Figure 3:
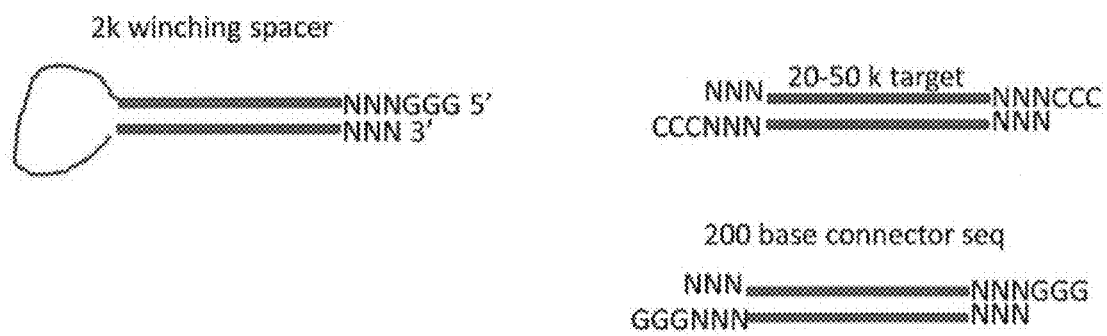
FIG. 3 is a schematic illustration of embodiments of molecules that can be used in loading methods that utilize winching or fishing mechanisms.

In further examples, prior to being processed to draw the molecules into the well, further pluralities of template nucleic acid monomers are distributed to ligate additional monomers to the ends of the tethering nucleic acid. Any number of monomers can be so distributed, resulting in a ligated molecule that comprises a concatemer of the monomers distributed. The monomers making up that concatemer may be identical to each other, or they may be different. The concatemers may further include intervening linker molecules to designate the end of one monomer and the start of the next. These linker molecules may include oligonucleotide sequences, and in further embodiments these oligonucleotide sequences are of known sequence and can in still further embodiments serve as barcodes for the adjacent template nucleic acid monomers. Increasing the number of monomers and intervening linkers can improve genomic coverage by providing more independent, long subreads in downstream sequencing reactions. The linker molecules can be distributed and then ligated to the ends of each concatemer in intervening cycles between distribution of template nucleic acid monomers. More typically, multiple template monomers and intervening connectors are distributed to the surface and ligated in a single reaction step. Control over the ligation to ensure that the linkers only bind to the end of the template nucleic acid monomers rather than to each other can be established by designing overhangs of the linkers such that they are only able to ligate to the monomers but not to each other. See, e.g., the exemplary 200 base pair linker in FIG. 3, whose overhangs are complementary to the overhangs on the template monomer but not to the overhang on the winching tether. Similarly, the overhangs on the monomers can be chose to ensure that they bind to the winch and linkers rather than to each other. Overhangs of 1, 2, 3, 4, 5, 6, or more bases are optionally provided.

As will be appreciated, the concatemers described above can be of any length, as the ability to load them into the reaction sites is significantly improved by the use of the winching tethering nucleic acids. The concatemers may in further embodiments be about 3000-150,000 nucleotides in length. In still further embodiments, the concatemers are about 4000-18000, 5000-16000, 6000-14000, 8000-12000, 10000-11000, 10000-50000, 20000-60000, 30000-70000, 40000-80000, 50000-90000, 10000-100000, 20000-80000, 30000-60000, 80000-200000, 90000-180000, 100000-160000, 110000-140000 nucleotides in length. In further embodiments, the concatemers are at least about 15,000; 20,000; 25,000; 30,000; 40,000; 50,000; 60,000; 70,000; 80,000; 90,000; 100,000; 120,000; 130,000; 140,000; 150,000 nucleotides in length.

In further embodiments and in accordance with any of the above, the tethering nucleic acid molecules are at least about 1000 to about 5000 nucleotides in length. In still further embodiments, the tethering nucleic acid molecules are about 1000-10000, 1500-9000, 2000-8000, 2500-7000, 3000-6000, 3500-5000, 4000-4500 bp (the equivalents for any non-nucleic acid winching molecules) in length. In yet further embodiments, the tethering nucleic acid molecules are about 500, 750, 1000, 1500, 2000, 2500, 3000, 3500, 4000, 4500, 5000, 5500, 6000, 6500, 7000, 7500, 8000, 8500, 9000, 9500, 10000 bp (or the equivalent thereof for non-nucleic acid winching molecules) in length.

As is described in further detail herein, the template nucleic acid monomers may be of any structure and may comprise without limitation DNA, RNA, or a mixture of DNA and RNA. In certain aspects, any of the winching mechanisms described above result in a ligated sequencing template that comprises one or more template nucleic acid monomers ligated in series to a winching molecule such as a tethering nucleic acid. In some embodiments, the ligated sequencing templates in their final form before the processing that draws the ligated molecule into the reaction site comprise a hairpin loop at one or both ends of the ligated sequencing template. Such hairpin loops can provide a way for any subsequent sequencing reactions to provide redundant sequencing information by allowing the sequencing reaction to proceed along both strands of the double stranded portion of the ligated sequencing template, e.g., when added to the terminal template monomer.

As discussed above, the winching molecules are generally immobilized within the reaction site. In embodiments in which the reaction sites are nanoscale wells, the immobilization may be at or near the base of the nanoscale wells. In further embodiments, the winching molecules are tethering nucleic acid molecules that are immobilized through association with a polymerase enzyme that is itself immobilized on the reaction site (such as at or near the base of a nanoscale well), e.g., through interaction of a biotinylated polymerase with streptavidin that is in turn bound to a biotinylated surface.

In embodiments in which a polymerase is used to process the winching molecule to bring it and the captured molecule/complex of interest into the reaction site, the polymerase may be maintained in an inactive state until the molecule/complex is ready to be brought into the reaction site. This provides control over the system such that the winching molecule is not brought into the site until all ligation steps and capture of the molecule of interest onto the winch is complete. Any method known for maintaining polymerases in an inactive state, including the use of analogs that cannot be processed by the polymerases (e.g., non-hydrolyzable analogs) can be used. In other embodiments, polymerization rate can be slowed by employing a low concentration of nucleotides or analogs. In addition, the winch can be locked into place on the polymerase, for example with chemical cross-links. For example, a bifunctional cross-linker can be reacted with residues in the polymerase on each side of the bound winching molecule (which will in this embodiment generally be a tethering nucleic acid), topologically encircling it to stabilize the polymerase/nucleic acid complex. See, e.g., U.S. Pat. No. 7,745,116 and US patent application publication 2015/0086994, each of which is incorporated herein by reference in its entirety for all purposes, and in particular for all teachings related to locking enzymes. Cysteine residues can be introduced into the polymerase at suitable positions for cross-link formation. For example, a recombinant φ29 polymerase can include, e.g., A83C and E420C substitutions, D84C and E418C substitutions, V19C and N409C substitutions, and/or N409C and V568C substitutions. (See, e.g., US patent application publication 2014/0094375, incorporated herein by reference in its entirety for all purposes, for the sequence of wild-type φ29 polymerase.) Existing solvent accessible cysteine residues can be mutated to ensure that the cross-link is formed between the desired pair of residues; thus, a suitable recombinant φ29 polymerase can also include one or more substitutions such as, e.g., C106S and/or C448V. Suitable bifunctional linkers are known in the art, for example, a bismaleimide linker, e.g., a bismaleimide-PEG linker, e.g., 1,11-bismaleimido-triethyleneglycol (BM(PEG)$_3$). Other coupling chemistries that can be employed include, e.g., thiol reactive reagents and disulfide containing reagents, e.g., haloacetyl crosslinkers (e.g., linkers including two iodoacetyl/iodoacetamide or bromoacetyl groups) and linkers with two pyridyl disulfide groups. The body of the linker can include, e.g., PEG (polyethylene glycol), an oligopeptide (e.g., polyglycine), or the like. Optimal linker length can be chosen based on the distance between the two residues to be cross-linked, e.g., in a crystal structure or other model of the polymerase. The linker is typically reacted with the polymerase after binding of the template (or primer/template); suitable reaction conditions for various linker chemistries are known in the art. Noncovalent linkers can also be employed. Such topological encirclement of the nucleic acid by polymerase can be particularly effective for circular nucleic acid molecules (including, e.g., simple circles and SMRTbells™ as described in, e.g., U.S. Pat. No. 8,153,375 "Compositions and Methods for Nucleic Acid Sequencing" and Travers et al. (2010) Nucl. Acids Res. 38(15):e159, each of which is incorporated herein by reference in its entirety for all purposes).

The winching methods described herein may in further embodiments benefit from use of polymerases that lack exonuclease activity to avoid degradation of the primer. Accordingly, polymerases for use in the above techniques optionally include one or more mutations (e.g., substitutions, insertions, and/or deletions) relative to the parental polymerase that reduce or eliminate endogenous exonuclease activity. For example, relative to wild-type φ29 DNA polymerase, one or more of positions N62, D12, E14, T15, H61, D66, D169, K143, Y148, and H149 is optionally mutated to reduce exonuclease activity in a recombinant φ29 polymerase. Exemplary mutations that can reduce exonuclease activity in a recombinant φ29 polymerase include, e.g., N62D, N62H, D12A, T15I, E14I, E14A, D66A, K143D, D145A and D169A substitutions, as well as addition of an exogenous feature at the C-terminus (e.g., a polyhistidine tag). See, e.g., US patent application publication 2014/0094375, incorporated herein by reference in its entirety for all purposes, for the sequence of wild-type φ29 polymerase. In further embodiments, the primer can incorporate one or more phosphorothioate or similar linkages to resist exonuclease activity of the polymerase.

Suitable ligases (e.g., T4 ligase or a single-stranded DNA damage repair ligase) are well known in the art and are commercially available. Appropriate reaction conditions are similarly known. Addition of a "crowding" agent such as polyethylene glycol and/or use of an increased concentration of ligase can be helpful in some instances. In some embodiments, loading of the tether, provision of the template monomers, and/or ligation can benefit from density loading techniques such as those described in U.S. Ser. No. 62/257, 152, filed Nov. 18, 2015, hereby incorporated by reference in its entirety for all purposes. In certain embodiments, rather than ligation, recombinase or transposase techniques (e.g., cre-lox recombination) known in the art can be used to create concatemers used in the methods described herein.

V. Electrode Position

In some examples, the methods described herein utilize a mechanism in which a capture molecule is delivered to a reaction site through the use of electrodeposition. Such mechanisms include the use of a capture molecule that is water soluble and charged at one pH and water insoluble and uncharged at another pH. Thus, changing pH, for example, by applying a voltage differential and taking advantage of the pH change at electrodes in solution, can deposit and immobilize the capture molecule (and any associated molecules, such as template nucleic acids, polymerases, and/or complexes containing both a template nucleic acid and a polymerase) to a reaction region site. In further examples, these electrodeposition methods are used to immobilize reactants at the base of nanoscale wells. In such examples, the nanoscale wells may be part of an array. These arrays may further include a solution layer above the wells as well as a conducting layer that allows exposure of cathodes at or near the base of each nanoscale well. Capture molecules are provided to the array, and those capture molecules will in certain examples have a pKa near neutral pH, e.g., a pKa between 6.0 and 8.0. In some examples, the capture molecules are water soluble in their protonated, charged form and insoluble in their deprotonated, uncharged form. Exemplary such capture molecules include polycations such as chitosan, polyimidazole, and polyhistidine. Reactants can be attached to the capture molecules, and a voltage applied through an anode in the solution layer to selectively deposit the capture molecules onto the bases of the nanoscale wells, thus immobilizing the attached reactants to the bases of the nanoscale wells. As will be appreciated, this configuration can be altered for capture molecules based on their pKa, such that the voltage differential is produced by using a cathode in the solution layer and having the conducting layer that allows exposure of anodes at or near the base of the nanoscale wells, e.g., for electrodeposition of capture molecules that are water soluble in their deprotonated, charged form and insoluble in their protonated, uncharged form, e.g., polyanions such as alginate.

Figure 5:
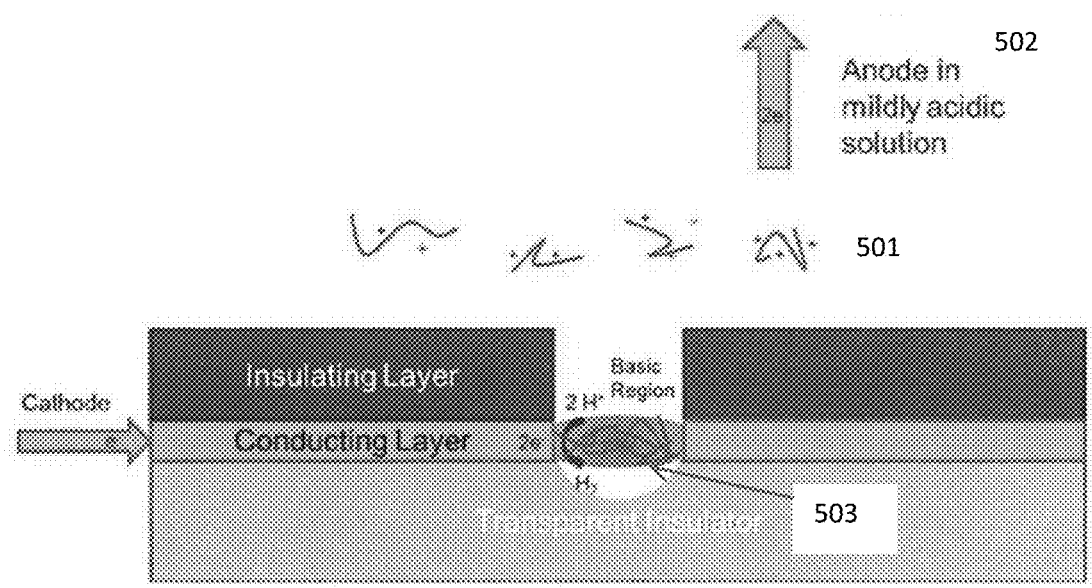
FIG. 5 is a schematic illustration of an exemplary configuration of a reaction site for use with a loading method that utilizes electrodeposition mechanisms with capture molecules whose solubility changes with changes in pH.

One embodiment of the invention is illustrated in FIG. 5. As shown, the device includes an insulating layer, a conducting layer, and a transparent insulator. A nanoscale well is provided that reaches through the insulating and conducting layer to have a base within the transparent insulator. The conducting layer is situated to allow exposure of cathodes at or near the base of the nanoscale well. Capture molecules 501 are provided to a solution layer above the nanoscale well (which in some embodiments is part of an array). In certain embodiments, the capture molecules have a pKa near neutral pH and are water soluble in their protonated form and insoluble in their deprotonated form. Reactants can be attached to the capture molecules using any methods known in the art. A voltage can then be applied through an anode (502) in the solution to selectively deposit the capture molecules onto the bases of the nanoscale wells (503), which serves to also immobilize the attached reactants to the base of the nanoscale well. In other embodiments, the capture molecules are first selectively deposited, and then the reactants are attached to the capture molecules at the base of the nanoscale well. In further exemplary embodiments, the capture molecules include without limitation chitosan and the reactants include complexes containing polymerase enzymes associated with template nucleic acids that are optionally hybridized to primers. In further embodiments, the method includes a step of exposing the nanoscale well to an aqueous solution with pH less than 4 in order to remove the capture molecules and attached reactants to prepare the nanoscale wells for delivery of a new set of capture molecules. In an embodiment related to that shown in FIG. 5, a transparent conducting layer (e.g., an indium tin oxide layer) forms the base of the nanoscale well and serves as the cathode.

As will be appreciated, the above-described electrodeposition method may also be performed through application of voltage by a cathode in the solution layer above the nanoscale well. In such an embodiment, the conducting layer allows exposure of anodes at or near the base of each nanoscale well, and the capture molecules are water soluble in their uncharged form and insoluble in their charged form. As with the method described above, the attaching of reactants to the capture molecules can be accomplished before application of the voltage for selective deposition or after application of the voltage.

For any of the electrodeposition methods described herein, the reaction site may in some embodiments include a nanopore. An exemplary embodiment would be if the device in FIG. 5 were to be drilled completely through such that rather than having a base in the transparent insulator a pore is formed. The use of voltage for selective deposition above would equally apply to such nanopores, and the deposition would be within the nanopore.

In one exemplary embodiment, observation of biochemical reactions in zero-mode waveguides using electrodeposition methods involves the immobilization of reactants at the base of the ZMW. The polysaccharide chitosan (deacetylated chitin) contains primary amino groups with pKa's of about 6. The protonated form is water soluble, while the deprotonated polymer is insoluble. This feature enables selective deposition from mildly acidic solutions at the basic region generated around the cathode under applied voltage (Wu et al., 2002, Langmuir 18:8620-8625). This feature has enabled the controlled assembly of chitosan hydrogels in a variety of micro fluidic devices (Kim et al., 2015, Polymers, 7:1-46). In addition to the polysaccharide, modified chitosans such as protein-chitosan conjugates (Chen et al., 2003, Langmuir, 19:9382-9386) and biotin-chitosan conjugates (Shi et al., 2008, Macromolecular Bioscience, 8:451-457) have also been directed to cathode surfaces through electrodeposition. The incorporation of a conducting layer in a surface (see FIG. 5) would allow exposure of cathodes to solution at the base of each ZMW. Applying voltage through an anode in solution promotes the selective deposition of chitosan or chitosan derivatives at the base of the ZMW, targeting molecules of interest to this location. If a transparent conductor such as indium tin oxide were layered below an opaque insulating material, the upper layer of the chitosan hydrogel could be in the observation volume of the waveguides. While stable in neutral solutions, these chitosan membranes can be resolubilized in mildly acidic solutions (pH<5). If the ZMW devices were fabricated to be tolerant of exposure to aqueous solutions in the pH range of 4-8, the immobilization surface could be removed and regenerated repeatedly. Chitosan has abundant reactive amines that have been coupled to a variety of biomolecules, and thus molecules of interest, including nucleic acid templates and complexes containing polymerases and template nucleic acids, can be readily attached via those reactive amines and delivered to the base of the ZMWs with the above described process.

VI. Electrophoretic/Pressure

In some examples, the methods described herein utilize a mechanism in which template nucleic acids or other molecules of interest are delivered to a reaction site, such as a nanoscale well, through the application of pressure or voltage. In one example, the reaction sites are overlaid by an array of chambers such that the chambers line up directly with the reaction sites. Voltage or pressure is used to drive molecules into the chambers. Then, because the reaction sites will typically have larger openings than the upper openings of the chambers, the molecules within the chambers are more likely to diffuse into the reaction site rather than out of the chambers.

The upper openings of the array of chambers optionally have diameters of about 20-100, 20-80, 25-75, 30-70, 35-65, 40-60, 20-50, 30-75 and 30-55 nm. In yet further embodiments, the upper openings of the chambers have diameters of about 25, 30, 35, 40, 45, 50, 55, 60, 65, 70, 75, 80, 85, 90 nm.

As shown in FIG. 18A, chambers 1801 are conveniently fabricated as holes through layer or sheet 1803, e.g., that is aligned on top of substrate 1805 in which nanoscale wells 1807 (e.g., ZMWs) are formed. Each chamber can be, e.g., cylindrical. More typically, however, the top opening of the chamber is smaller than the bottom opening, as shown in FIG. 18A. The opening of the nanoscale well is optionally smaller, larger, or the same as the bottom opening of the chamber, but is typically larger than the top opening of the chamber. In one exemplary embodiment, the top opening of the chamber is 25-75 nm in diameter while the bottom opening of the chamber is 200-500 nm. In an exemplary embodiment, the depth of the chamber is 100-500 nm.

In another example, a fluid-filled chamber is located above the reaction sites, and a loading screen is provided to the top of the fluid-filled chamber, wherein the loading screen comprises randomly or nonrandomly placed holes. A solution containing template nucleic acids or other molecules of interest is applied to the loading screen and then pressure or voltage is applied to the solution to drive the template nucleic acids into the fluid-filled chamber through the holes of the loading screen. The template nucleic acids then passively diffuse from the fluid-filled chamber into the nanoscale wells. The holes in the loading screen over the fluid filled chamber optionally have diameters of about 20-100, 20-80, 25-75, 30-70, 35-65, 40-60, 20-50, 30-75 and 30-55 nm. In yet further embodiments, the holes in the loading screen have diameters of about 25, 30, 35, 40, 45, 50, 55, 60, 65, 70, 75, 80, 85, 90 nm.

As shown in FIG. 18B, loading screen 1841 is conveniently fabricated as holes 1845 through a film or thin sheet. Screen 1841 overlies fluid-filled chamber 1843. Holes 1845 are optionally randomly placed as shown in FIG. 18B. In other embodiments, the holes are nonrandomly positioned, e.g., to align with the openings of nanoscale wells 1847 in substrate 1849. The holes are typically smaller in diameter than the openings of the nanoscale wells. In one exemplary embodiment, the holes in the screen are 50 nm in diameter and the fluid-filled chamber has a depth of 150-500 nm.

For any of the embodiments involving loading through use of electrophoresis or pressure, the reaction sites may comprise an array of nanoscale wells. The nanoscale wells will typically have openings larger than the upper openings of the array of chambers or the holes in the loading screens. The applied electric field or pressure is optionally pulsed. Without limitation to any particular mechanism, such pulsing can load a small amount of nucleic acid into the chamber at a time to prevent entanglement.

For any of the methods described above, the molecules to be delivered to the reaction sites may include template nucleic acids, e.g., in complex with polymerase enzymes and/or primers. In still further embodiments, the template nucleic acids are about 3-30, 5-20, 7-10, 7-15 kb in length.

Further exemplary embodiments of approaches to electrophoretic loading are provided in FIGS. 6-11. These embodiments include several methods to achieve direct loading through an applied voltage between (1) a conducting functionalized substrate; (2) the metal cladding of a near-field aperture array (ZMW); (3) a polarized electrode; (4) an embedded layer in the substrate and counter electrode in solution. Although the following descriptions are provided in terms of ZMWs, it will be appreciated that any reaction sites can be used in these methods.

Figure 6A:
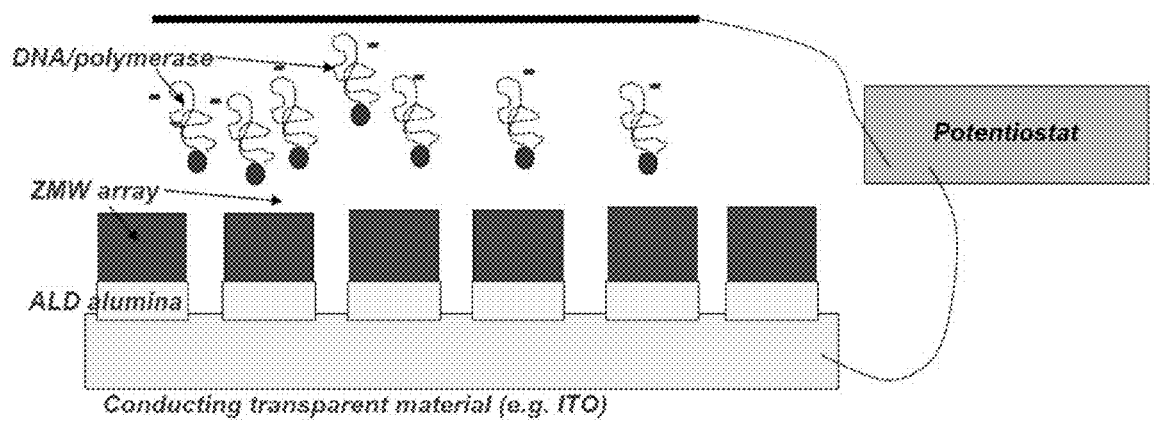
FIG. 6A-FIG. 6C is a schematic illustration of an exemplary configuration of a reaction site for use with a loading method that utilizes electrophoretic mechanisms.
Figure 6B:
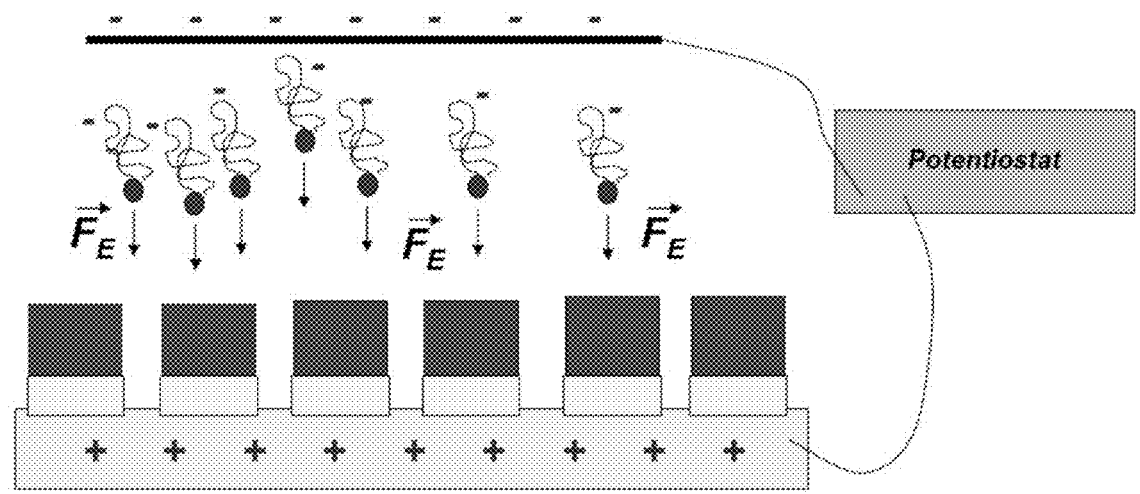
Figure 6C:
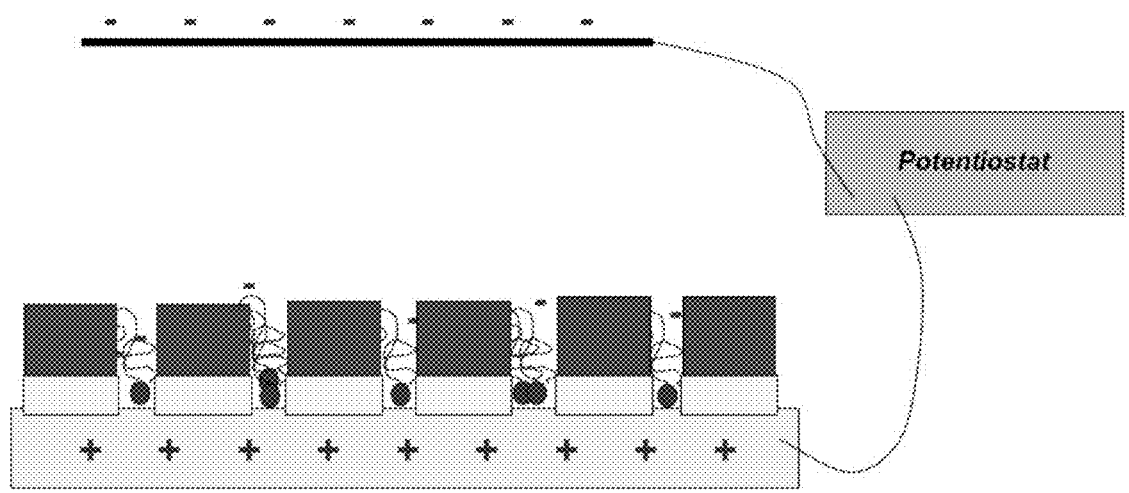

FIG. 6A shows a schematic of approach (1) (A conducting functionalized substrate). The substrate, which is typically fused silica, could be made of any optically transparent material (e.g. ITO). A barrier metal oxide layer serves to insulate the substrate from the metal cladding. The conducting substrate can be connected to a terminal of a suitable voltage source (e.g. battery or potentiostat). A counter electrode (e.g. platinum wire) connects to the voltage supply to complete the circuit. In this manner, charged molecules (e.g. DNA) can be directed to (or from) the ZMW bottom due to the electric field-induced force (FIG. 6B), thereby increasing the local density proximal to the ZMWs and facilitating loading into ZMWs (FIG. 6C). Optionally, the ZMW bottom may be functionalized (e.g. biotinylated) for specific attachment of target molecules.

Figure 7:
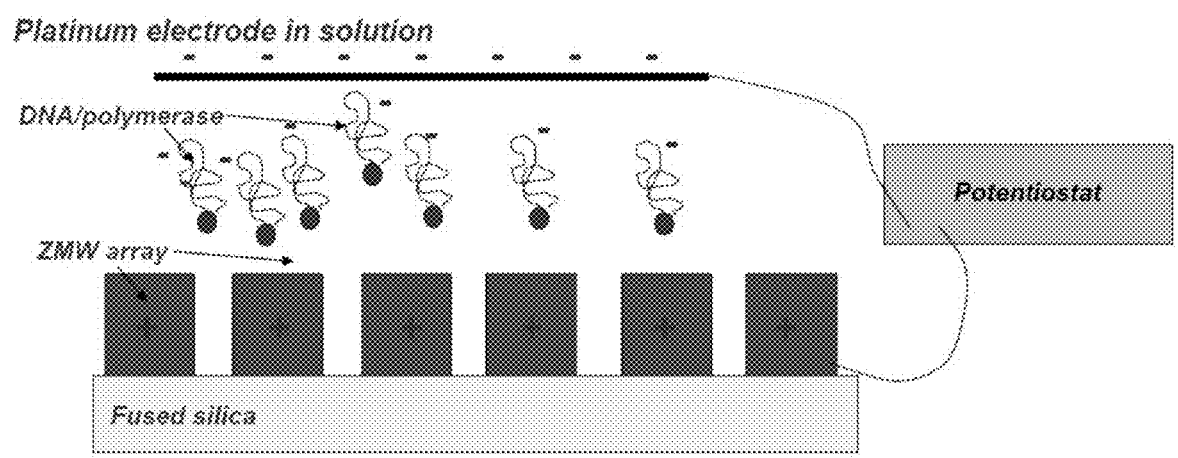
FIG. 7 is a schematic illustration of an exemplary configuration of a reaction site for use with a loading method that utilizes electrophoretic mechanisms.

FIG. 7 shows a schematic of approach 2 (Electrode attachment to the metal cladding of a ZMW array). In this method, a voltage is applied between the ZMW cladding metal and a counter electrode in solution.

Figure 8:
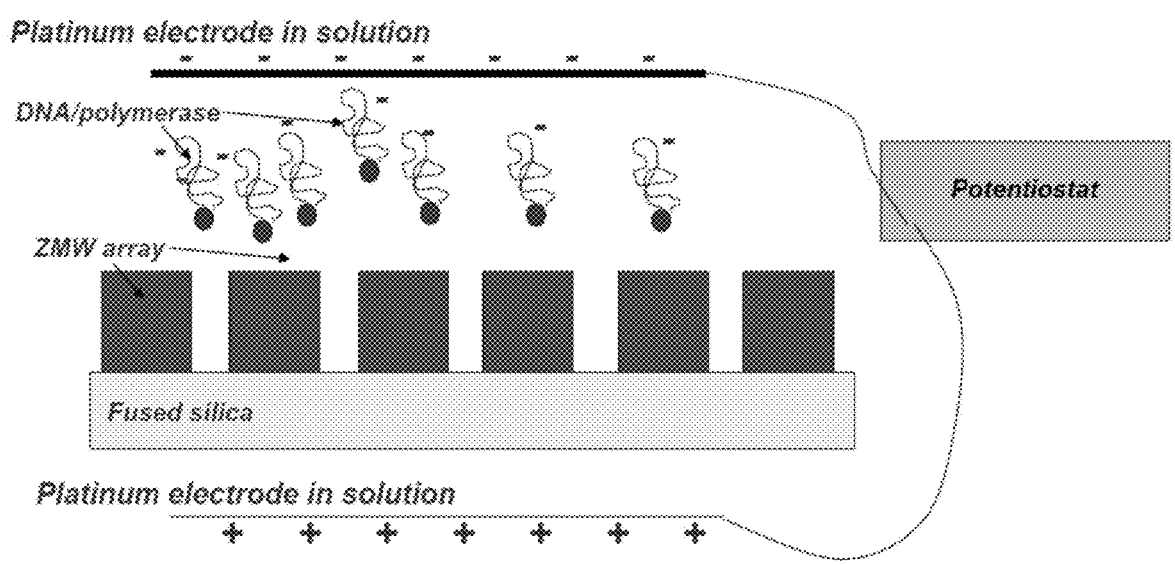
FIG. 8 is a schematic illustration of an exemplary configuration of a reaction site for use with a loading method that utilizes electrophoretic mechanisms.

FIG. 8 shows a schematic of approach 3 (A polarized electrode). In this method, a voltage is applied between a working electrode (e.g. platinum wire or sheet) and a counter electrode (e.g. platinum wire or sheet) in solution with a target ZMW array located in between.

Figure 9:
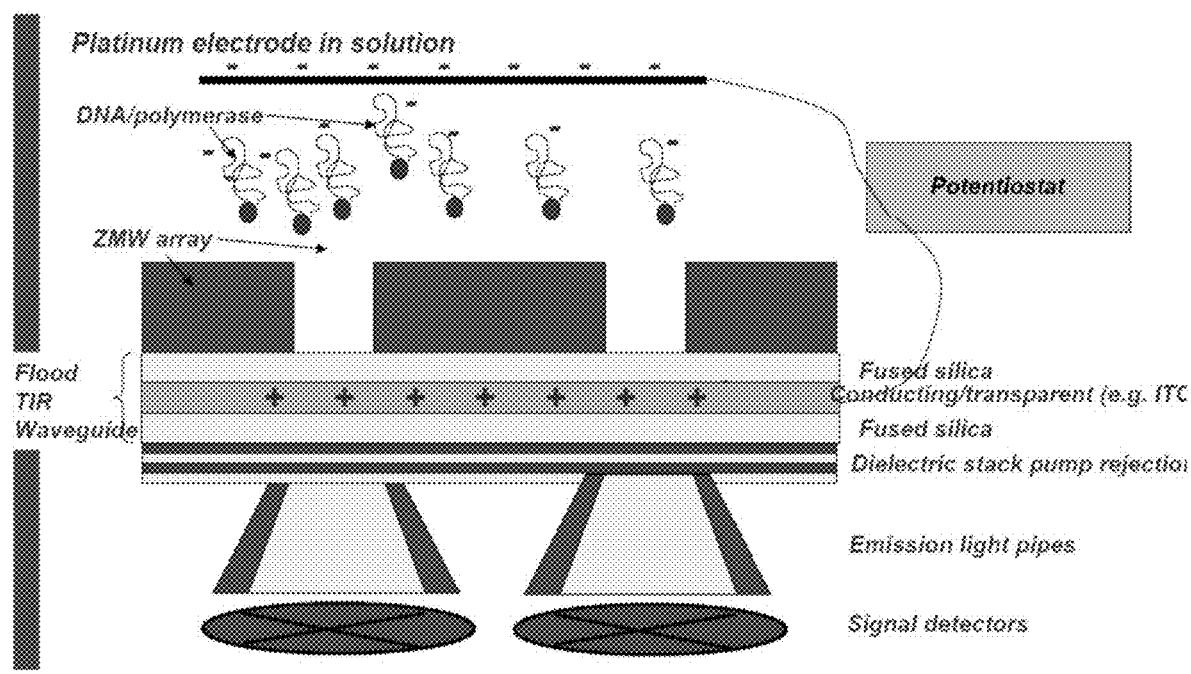
FIG. 9 is a schematic illustration of an exemplary configuration of a reaction site for use with a loading method that utilizes electrophoretic mechanisms.

FIG. 9 shows a schematic of approach 4 (an embedded layer within the substrate). In this method, a voltage is applied between a working electrode (e.g. platinum wire or sheet) and a counter electrode transparent sheet under the substrate. Optionally, this sheet can be integrated into an optode. Optionally, this sheet may form part of the waveguide.

Figure 10:
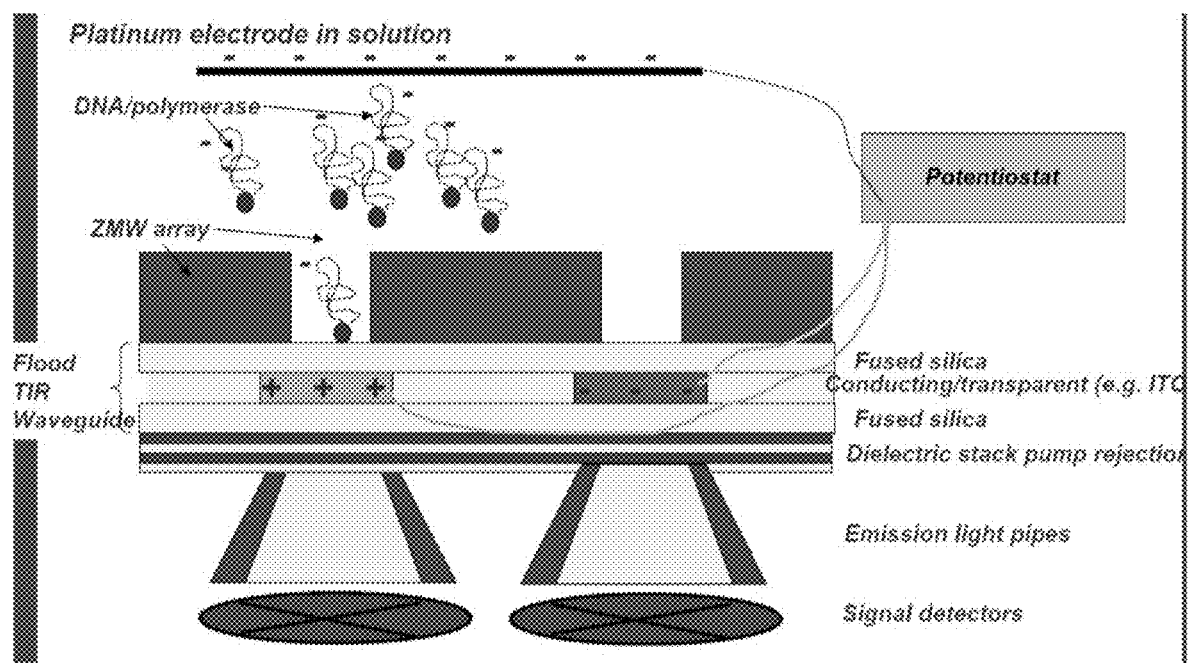
FIG. 10 is a schematic illustration of an exemplary configuration of a reaction site for use with a loading method that utilizes electrophoretic mechanisms.
Figure 11:
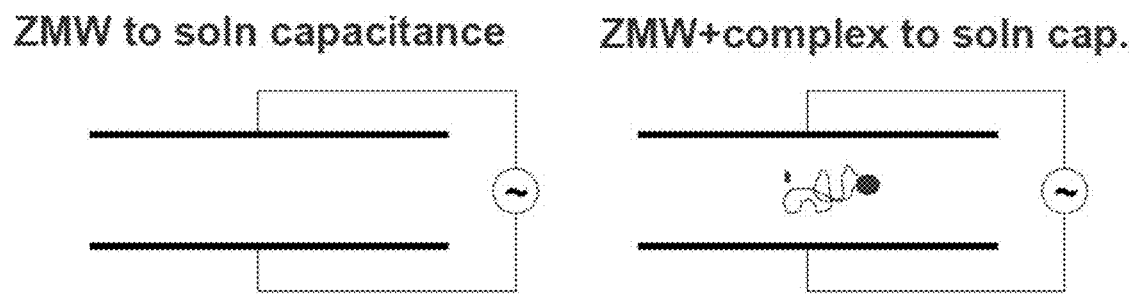
FIG. 11 is a schematic illustration of an exemplary configuration of a reaction site for use with a loading method that utilizes electrophoretic mechanisms.

A potential applied across the electrodes enables controlled mobility of charged molecules in solution. This method can also be applied to individual ZMWs through a counter electrode in solution and a working electrode underneath each ZMW (e.g. a conducting pad or ring) (FIG. 10). Optionally, these ZMW specific pads can be integrated into an optode. Optionally, these pads can be individually addressable or addressed as interlaced arrays, possibly using existing ZMW-specific electrical connections to the proximal detector or pulse-to-base processing unit.

Physical properties of the electrode/ZMW/chemistry composite can also be monitored during active loading, e.g., capacitance, at various scales from individual ZMWs to entire arrays of ZMWs. Physical properties that change when a complex loads into a given ZMW can also be monitored, e.g., capacitance (FIG. 11), which gives a direct readout of the current loading status. For individual ZMWs, this can be used to achieve Super Poisson loading, by facilitating loading per ZMW until loaded, then reversing the voltage to reject further loading (but not so strongly that the loaded template gets ripped out of the ZMW). Optionally, the bias voltage that forces complex to the ZMWs could be modulated, or the sign even reversed for short periods of time. For such an AC signal, the relaxation time constant (1/RC) could be monitored, and a change in that signal corresponding to a loaded complex could be the trigger to stop further loading into that ZMW. For ZMW arrays, the desired loading can be targeted in real time, which could compensate for other factors that impact loading speed (e.g., template size variation, chip quality, ZMW size variation, etc.).

Any of the methods for electrophoretic loading may be combined with any other loading methods described herein and known in the art, including other electrophoretic loading methods such as those described for example in PCT Publication No. WO 2013/096819.

In some embodiments, loading through electrophoresis or pressure includes the use of entropic barriers to facilitate loading in reaction sites such as nanoscale wells. In general, such loading methods are used with a device configured to have at least one fluidic channel overlaying a nanoscale well (generally over an array of nanoscale wells), where the fluidic channel includes alternating thick and thin regions, e.g., regions of differing degrees of confinement (with a lesser confinement relating to "thick" regions and a greater degree of confinement relating to "thin" regions). Voltage or pressure is used to drive nucleic acids through the fluidic channel over the nanoscale well(s). The thin regions of the channel serve as entropic barriers, such that upon application of voltage (electric potential) or pressure (including hydrodynamic pressure), a local increase in nucleic acid concentration occurs through an entropic trapping effect. If the entropic barriers are positioned appropriately, this concentration increase can be situated above the reaction sites, thus improving the ability to load the reaction sites with molecules of interest. Such methods can be particularly useful for loading nanoscale wells, such as ZMW's, which often pose loading barriers due to their own entropic barriers to entry that is a result of their relative scale to the surroundings and the molecules being loaded. An additional benefit of using entropic barriers is that the entropic trapping effect can preferentially concentrate longer molecules (e.g., molecules whose radius of gyration is significantly greater than the depth of the thin regions) and thus act to compensate for length-dependent loading effects that tend to preferentially load small fragments. In certain embodiments, the longer molecules that are successfully loaded comprise nucleic acids on the order of kilobases or megabases in length.

By judicious use of variations in the degrees of confinement along the direction of flow, the directed loading of an individual molecule to an individual sequencing location can also be developed. In general, the thin regions are sufficiently small to act as constrictions to the flow of small objects, such as DNA molecules, polymerase enzyme complexes, proteins, cells, viruses, or other similarly-sized particles, while the thick regions allow molecules to relax for more efficient collection at the thin region. To this end, the thick region depth may be made comparable to, or substantially larger than, the size of a molecule (for example, the radius of gyration $R_o$ for polymer molecules) to be moved through the manifold. Also the thin region depth may be made substantially smaller than the size of the molecule or other object to be moved through the device (e.g., substantially less than $R_o$). Although this configuration of devices used in the methods described herein can be used to load a variety of objects, much of the description herein will be in terms of molecules, and particularly nucleic acid molecules for convenience. Without being bound by theory, the entropic barriers described herein help develop local concentrations of molecules because the equilibrium spherical shape of a molecule such as DNA or protein has a radius of gyration $R_o$, which is the shape the molecule assumes when it is relaxed in an open region, such as in the thick regions of the channel. If the molecule is forced to enter a constriction that is much less than $R_o$, the molecule has to be deformed from its equilibrium shape. Since such a deformation is entropically unfavorable, an increased driving force is required to force the molecule to enter the constriction. This effect is referred to as the entropic trapping of a long polymer, such as a nucleic acid. Thus controlling the driving force allows control over the movement of the molecules along the channel and where local increases of concentration occur due to regions of greater confinement (constrictions) that serve as entropic barriers.

Figure 19:
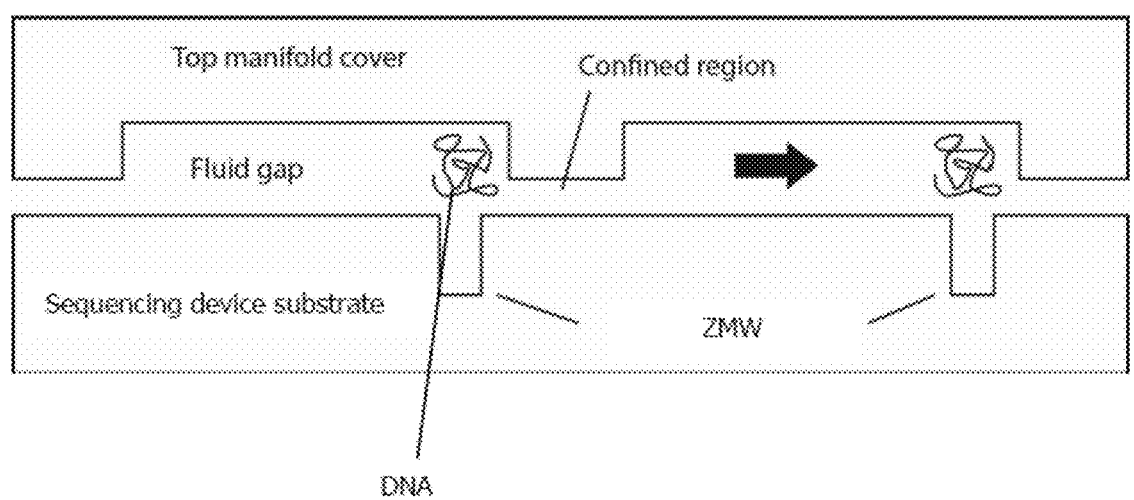
FIG. 19 is a schematic illustration of an exemplary configuration of a device for use in a loading technique utilizing entropic barriers.

One exemplary embodiment of a configuration that utilizes entropic barriers is illustrated in FIG. 19, which provides a side view of the nanoscale well and the overlaying channel. In such a configuration, the flow of nucleic acids (denoted by the arrow pointing from left to right in FIG. 19) is tangential to the surface of a substrate, for example such as one employed in the Pacific Biosciences Sequel System®. In this arrangement, a nanofluidic manifold (designated "top manifold cover" in FIG. 19) is positioned over the substrate to form a channel positioned tangential to the surface of the substrate. The nanofluidic manifold has variations that produce changes in the height of the channel, creating zones of lesser and greater confinement—e.g., "thick" and "thin" regions.

In embodiments utilizing voltage to move the nucleic acid molecules along the length of the channel, electrodes can be positioned at either end of the manifold to provide an electrophoretic force to drive molecules through the device. An aspect of the entropic trap array is that a drive voltage below a certain threshold will allow passage through the larger region of the channel (the "thick" region), but molecules above a certain size will not pass through the smaller region of the channel (the "thin" region). Above the voltage threshold, molecules will pass through both thick and thin regions without stopping. The threshold voltages can be easily identified and utilized based on the size of the molecules that are desired for loading into the reaction sites.

In a first phase of operation, a high driving force is applied to load molecules throughout the manifold. Then, in a second phase, the driving force is reduced so that the molecules collect at the next region of greater confinement (thin region). This will cause an increase in concentration which is proportional to the volume of the portion of the manifold between the two neighboring regions of greater confinement. By positioning the thin regions next to the nanoscale wells, the second phase of the driving force thus favors loading of the nanoscale wells through that local increase in concentration (see FIG. 19).

Figure 20:
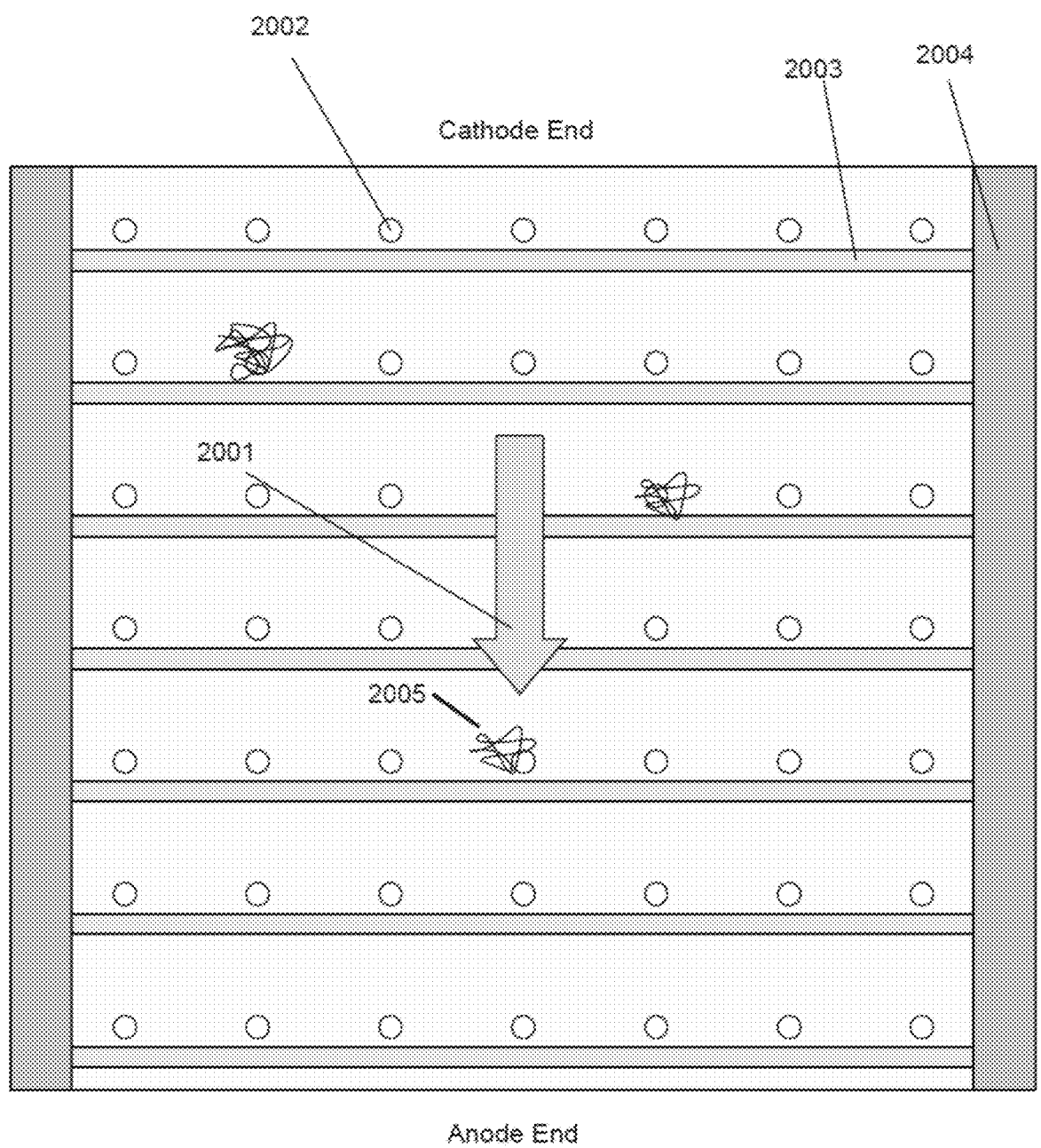
FIG. 20 is a schematic illustration of an exemplary configuration of a device for use in a loading technique utilizing entropic barriers.
Figure 21:
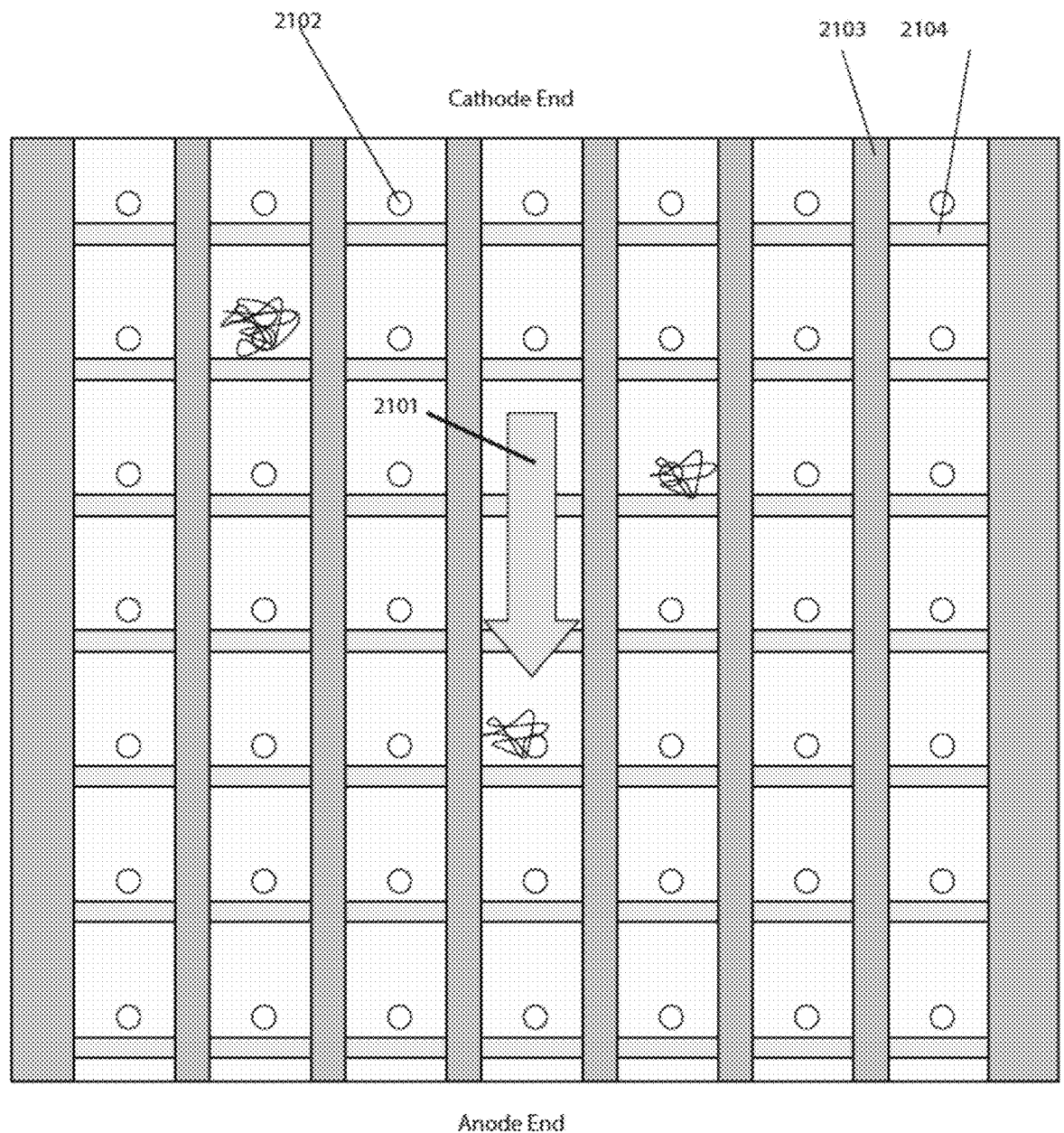
FIG. 21 is a schematic illustration of an exemplary configuration of a device for use in a loading technique utilizing entropic barriers.
Figure 22:
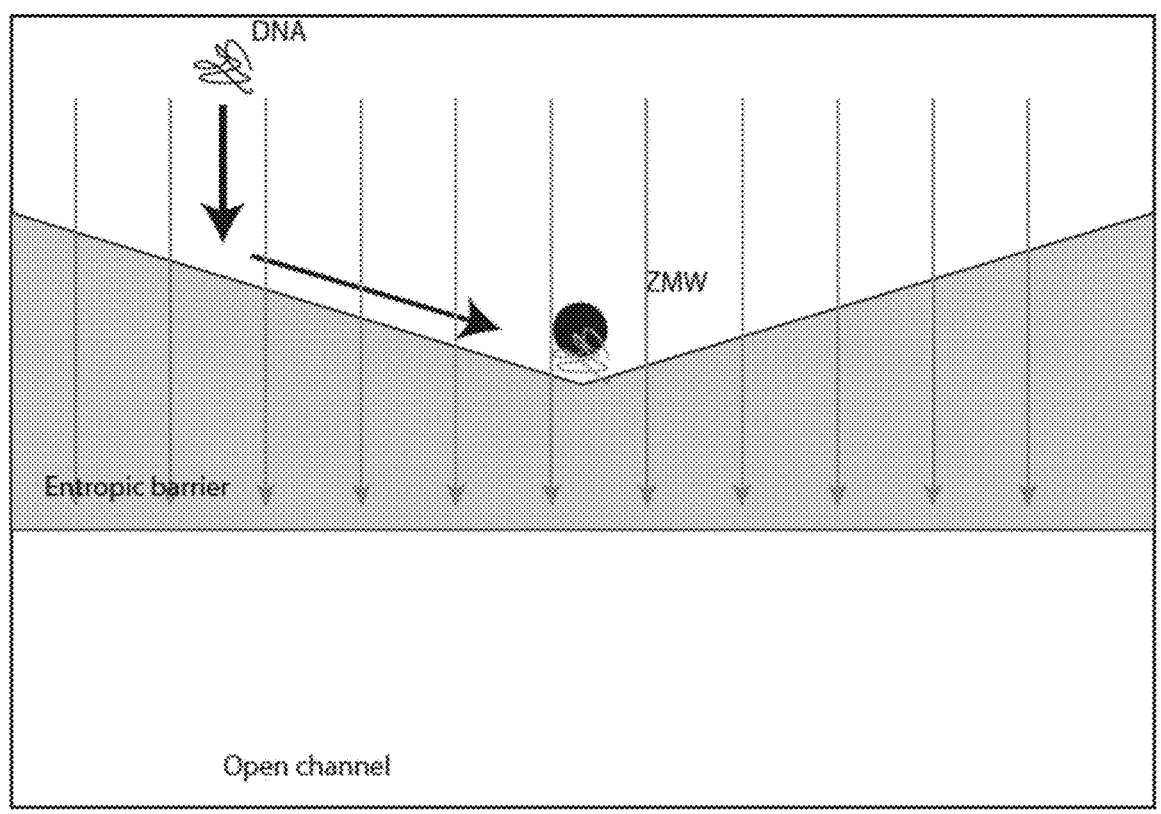
FIG. 22 is a schematic illustration of an exemplary configuration of a device for use in a loading technique utilizing entropic barriers.

As will be appreciated, the configuration of the entropic barriers can include any combination of thick and thin regions of greater and lesser confinement that are useful for loading one or more nanoscale wells with molecules of interest (such as nucleic acids). FIGS. 20-22 illustrate further exemplary embodiments of this aspect of the invention for exemplary arrays of nanoscale wells. As will be appreciated, although the discussion herein is primarily in terms of nanoscale wells for ease of discussion, any other configuration of reaction sites is encompassed by the methods and configurations described herein.

FIG. 20 shows a top-view of an "open channel" configuration in which an array of nanoscale wells (2002) is overlaid by an open channel formed by a wall (2004) on each side of the array—this open channel contains thin regions of greater confinement that form entropic barriers (2003) just after each row of nanoscale wells along the direction of flow (2001). These entropic barriers thus increase the concentration of nucleic acids (2005) over or in close proximity to the nanoscale wells (2002), thus increasing the probability that the nucleic acids are able to diffuse into the nanoscale wells. The exemplary configuration pictured in FIG. 20 shows a driving force that comprises voltage (an electrical potential) that serves to move the nucleic acids from the cathode end of the device toward the anode end. As will be appreciated, the direction of flow could be changed by reversing the electrical potential. In further embodiments, the same open channel configuration can be used in accordance with FIG. 20, but the driving force is provided by hydrodynamic pressure rather than electrical potential. In such an embodiment, the regions of greater confinement work as entropic barriers in the same way as when electrical potential is used as a driving force. In further embodiments, the open channel is large enough to cover the entire array of nanoscale wells. In certain embodiments, the open channel may cover part of the array but leave certain nanoscale wells free of the overlaying channel. Note that FIG. 20 is not drawn to scale, and that any combination of widths and degrees of confinement can be used as long as the ratio between the regions of greater and lesser confinement serve to set up entropic barriers that help to concentrate the nucleic acids at or near the regions of greater confinement, thereby increasing the probability of loading of nearby nanoscale wells with the nucleic acids.

FIG. 21 shows a top-view of an "closed channel" configuration in which an array of nanoscale wells (2102) is overlaid by a series of closed channels formed by walls (2103) separating columns of nanoscale wells from each other. Each of the channels contains regions of greater confinement that form entropic barriers (2104), such that as nucleic acids are driven along the array in a desired direction (2101), the entropic barriers increase the concentration of nucleic acids over or in close proximity to the nanoscale wells, thus increasing the probability that the nucleic acids are able to diffuse into the nanoscale wells. As with the configuration illustrated in FIG. 20, the driving force in a closed channel configuration such as that pictured in FIG. 21 can be an electric potential (illustrated in the figure by driving from a cathode end to an anode end) or by hydrodynamic pressure. In certain embodiments, the number of channels overlaying the array is equal to the number of columns of nanoscale wells that are present in the array, such that every nanoscale well is overlaid by a channel. Note that FIG. 21 is not drawn to scale, and that any combination of widths and degrees of confinement can be used as long as the ratio between the regions of greater and lesser confinement serve to set up entropic barriers that help to concentrate the nucleic acids and thereby increase the probability of loading of the nanoscale wells with the nucleic acids.

FIGS. 20-21 illustrate embodiments in which the entropic barriers are configured to be at right angles to the flow path of the nucleic acid molecules (and the surface of the substrate housing the nanoscale wells). As will be appreciated, any configuration that develops an entropic barrier is encompassed by the disclosed invention. A further exemplary embodiment is illustrated in FIG. 22. FIG. 22 is a top view of a single nanoscale well (ZMW) in which the entropic barrier is formed as a chevron shape in which the sides of the entropic barrier angle toward the ZMW. An advantage of such a configuration is that in addition to increasing the local concentration near the nanoscale wells, the shape of the entropic barrier further enhances loading by disturbing the driving force such that it favors the "point" of the chevron, which is over or near the entrance of the nanoscale well. Although FIG. 22 illustrates an embodiment in which the molecule of interest being driven toward the ZMW is DNA, it will be appreciated that any charged molecule can be used in any of the configurations described herein when an electric potential is used as the driving force. When hydrodynamic pressure is used as the driving force, any molecule susceptible to such a force can also be used in this or any other configuration described herein. FIG. 22 illustrates an embodiment in which the open channel configuration is used, such as that illustrated in FIG. 20—however, similar chevron-shaped entropic barriers may also be used with the closed channel configuration such as that illustrated in FIG. 21.

For any of the configurations described herein for utilizing entropic barriers to assist in loading of nanoscale wells, the thin regions of greater confinement that function as entropic barriers can have any depth the serves to delay or substantially prevent the progress of molecules of interest, particularly charged molecules such as nucleic acids e.g., in polymerase enzyme complexes. In certain embodiments, the regions of greater confinement have a depth of about 1 nm to about 1000 nm. In further embodiments, the regions have a depth of about 10-900, 20-800, 30-700, 40-600, 10-500, 50-500, 60-400, 70-300, 80-200, 50-200, 90-100 nm. In still further embodiments, the regions have a depth of about 2-100, 2-50, 4-50, 30-50, 5-500, 5-10, 20-40, 80-120, 300-500, 100-600 nm. In yet further embodiments, the regions have a depth of about 2, 5, 10, 20, 30, 40, 50, 60, 70, 80, 90, 100, 200, 500, 750, 1000, 1250, 1500 nm. The thick regions of lesser confinement have a depth greater than that of the thin regions. In certain embodiments, the thick regions have a depth between about 0.5 µm and about 10 µm.

The material of the manifold and the substrate housing the nanoscale wells can comprise any suitable material that is conducive to use in the methods described above. Materials and techniques suitable for fabrication of the manifold are known in the art; see, e.g., U.S. Pat. No. 7,918,979. In certain embodiments, the top manifold is made out of a transparent material, and the molecules are labeled, for example with an intercalant dye. Such a configuration allows the observation of the molecules as they flow across the array of nanoscale wells in real-time. An advantage provided by this ability to observe the molecules in real time is that the loading of the nanoscale wells can be tracked—if wells are not loaded during the first pass through the array (which can be detected by observing the pattern of molecules left on the array), then the direction of the driving force can be reversed to allow another pass over the nanoscale wells with the molecules. This reversal and pass through of the detectable molecules can be repeated until the desired percentage of nanoscale wells in the array is loaded. As will be appreciated, any type of label or method that allows observation and monitoring of the movement of the nucleic acids in real time can be used to perform this aspect of the invention.

In further embodiments, and in accordance with any of the embodiments described above, it will be appreciated that the reaction sites may include any of the other types of molecules and configurations described herein such that loading of the reaction sites is further enhanced by such combinations and/or in order to include items in the reaction sites for downstream use of the reaction sites and the loaded nucleic acids. For example, the reaction sites may include capture moieties and/or other tethering molecules, such as those described above, which can interact with the nucleic acids or polymerase enzyme complexes and further encourage loading of the reaction sites with the nucleic acids or complexes. The reaction sites may further include polymerase enzymes and other reagents for use in downstream sequencing reactions once the nucleic acids are loaded.

In still further embodiments, configurations for use in accordance with any of the above described methods for utilizing entropic barriers further include devices, systems and methods described in the art for molecular sieving and trapping, including for example U.S. Pat. Nos. 7,918,979 and 6,635,163, which are herein incorporated by reference in their entirety for all purposes and in particular for all teachings and figures related to separation of molecules. In yet further embodiments, the entropic barrier methods described herein are not operated such that the barriers act as a "sieve" to separate certain molecules from others, but are instead used to concentrate molecules, particularly larger molecules, at certain regions along the path of flow of the driving force.

VII. Affinity Loading

Figure 12:
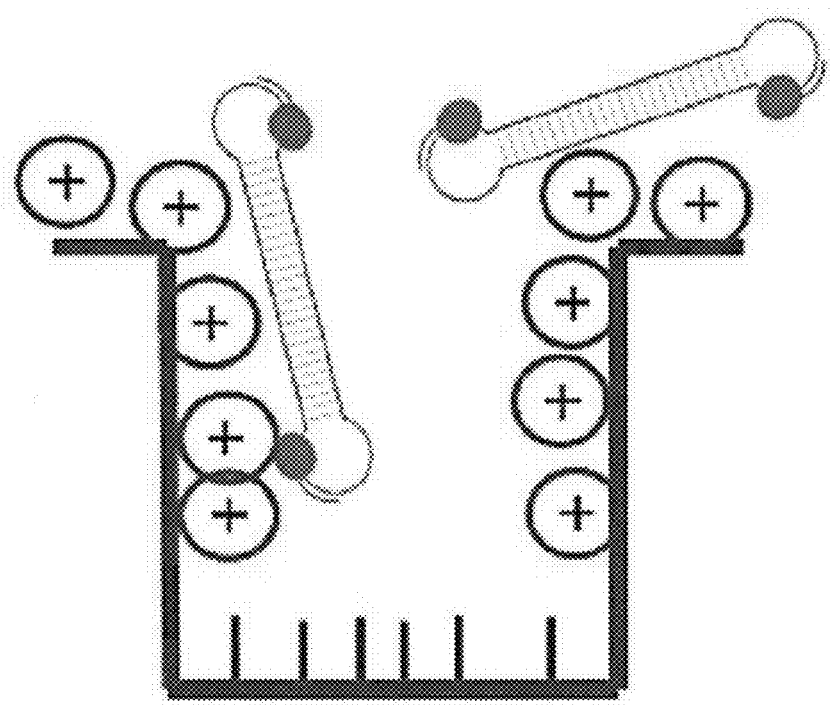
FIG. 12 is a schematic illustration of a loading method that utilizes affinity loading processes.

In some aspects, the methods described herein utilize a process involving affinity loading. In general, a surface containing reaction sites, such as nanoscale wells, is coated with a positively charged peptide. A composition containing molecules of interest that have negative charges (such as nucleic acid templates or polymerase enzyme complexes) is applied to the coated surface such that at least a portion of the molecules attach to the positively charged peptides (see schematic illustration in FIG. 12). This attachment increases the effective local concentration of the molecules of interest near the reaction sites. The molecules are then released from the positively charged surface to allow the molecules to passively diffuse into the reaction sites. A higher percentage of the molecules will load into the reaction sites than is seen with passive diffusion alone, because of the step of increasing the effective local concentration near the sites through affinity attachment to the positively charged peptides.

In specific aspects, these affinity loading methods include the steps of providing a surface comprising an array of nanoscale wells; coating that surface with a positively charged peptide to form a coated surface; applying a composition comprising polymerase enzyme complexes to the coated surface such that at least a portion of the polymerase enzyme complexes attach to the positively charged peptides; and releasing the polymerase enzyme complexes from the positively charged peptides or polypeptides to allow the polymerase enzyme complexes to passively diffuse into the nanoscale wells.

The releasing step generally involves applying a composition to the surface that can weaken or break the attachment between the molecules of interest and the positively charged peptides. For example, release can be accomplished by applying a protease (e.g., trypsin) to the surface to digest the positively charged peptide and release the polymerase enzyme complexes. As another example, the complexes can be released by elution with high salt (e.g., 500 mM potassium acetate).

In some embodiments, loading efficiency can be further improved by applying size exclusion resin to the surface, e.g., after application of the complexes to the coated surface and prior to elution of the complexes. For example, Sephadex G100 size exclusion resin can be applied to the surface (e.g., by application to a liquid layer overlying the surface). Without limitation to any particular mechanism, addition of the size exclusion resin can improve loading by effectively increasing the concentration of the polymerase-template complexes in the excluded volume and/or by acting as a barrier that slows diffusion of the complexes away from the surface after they have been eluted from the coating.

In general, the positively charged peptides or polypeptides that are applied to the surface can comprise anything that would provide a coated surface with an overall positive charge that is able to attract the molecules of interest for attachment near the reaction sites. Such peptides or polypeptides can include without limitation Tat, poly-lysine, poly-arginine, and histone. Peptides rich in arginine, lysine, and histidine may also be used. For peptides rich in histidine, loading would be conducted at pH below ~6. Deprotonation at a higher pH would then cause release from the surface when using such histidine-rich peptides. Non-peptide compositions, including cationic polymers (e.g., cationic branched polyethylene glycols), can also be employed.

In specific embodiments, the molecules loaded in the above-described affinity loading methods include polymerase enzyme complexes comprising polymerase enzymes attached to template nucleic acid molecules. In further embodiments, the template nucleic acid molecules are hybridized to a primer.

In further embodiments, the template nucleic acid molecules are at least 3, 5, 7, 10, 15, 20, 25, 30, 35, 40, 45, 50 kb long. In further embodiments, the template nucleic acid molecules are about 3-20, 5-15, 6-10, 2-25, 1-30 kb long.

These affinity loading methods generally result in loading of the molecules of interest, including polymerase enzyme complexes, at rates that are about 2-20, 4-15, 6-10, 10-150, 20-140, 30-130, 40-120, 50-110, 60-100, 70-80 times faster than seen with diffusion loading alone. In further embodiments, the affinity loading methods result in loading of at least 2, 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 250, 300, 350, 400, or 500 times faster than seen with diffusion loading alone. Without limitation to any particular mechanism, these affinity loading methods can favor loading of larger (e.g., at least 5000 bp) templates over smaller templates (e.g., less than 2000 or 1000 bp).

In specific embodiments, the affinity loading method includes steps of pre-coating a surface containing reaction sites (the surface will in some embodiments comprise a predominantly negatively charged material such as TiN or Al) with positively charged peptides (e.g., Tat, poly-lysine, histones). This coating will serve to condense complexes containing template nucleic acids and polymerases near and onto the surface. Once localized near the surface (which may contain biotin binding sites for capture of streptavidin-associated complexes), the complexes can be released (or affinity weakened) with a high salt elution step. This approach results in an increased local concentration and dwell time and has been shown to greatly improve loading when compared to diffusion loading.

In further embodiments and in accordance with any of the description for affinity loading methods described above, the positive charges may be designed to localize specifically to the reaction sites (such as ZMWs, particularly the bases of ZMWs), for more effective recruitment of the molecules of interest. In an exemplary embodiment, the reaction sites are selectively coated with streptavidins containing cysteines that have been labeled with a maleimide containing high molecular weight polylysine. The polylysine can help attract the DNA in a template nucleic acid such as a SMRTbell™. After the template nucleic acid (and any associated molecules such as polymerase enzymes) have been effectively loaded into the reaction sites, the polylysine can be removed prior to downstream analyses such as sequencing reaction through application of a protease such as trypsin. Similar methods can be accomplished using other coating materials such as polyarginine or any other composition that has affinity for both DNA and the reaction region. In further examples, the molecule/complex of interest can be coupled to a peptide that has affinity for the surface of a reaction site such as a ZMW, particularly the ZMW base (including any functionalization at the reaction site and/or binding moieties at the reaction site). In further embodiments, affinity for the ZMW base can be through a specific interaction such as biotin on the template nucleic acid or polymerase binding to streptavidin on the surface of the ZMW base (or vice versa) or through differential affinity for the ZMW base (which generally comprises a silica-based material) over the rest of the surface (which generally comprises metal or metal oxide). In further embodiments, phage display can be used to select peptides with affinity for various oxide surfaces. (See Seker et al., Molecules, 2011, 16: 1426-1461). Such peptides can be fused to molecules having affinity for nucleic acids (or other molecules of interest). In still further embodiments, affinity for the molecule of interest, particularly for a complex containing a nucleic acid template complexed with a polymerase, may be designed through the use of a nonspecific DNA binding protein selectively deposited at the reaction site (e.g., through specific or differential binding as described above). In other embodiments, any of the charged peptides and polypeptides discussed herein, including Tat, polylysine and polyarginine, can supply affinity for the template/polymerase complex or other molecule of interest. Fusion peptides including streptavidin-Tat, or streptavidin bound to biotinylated Tat, could also be used in accordance with any of the methods described herein as molecules for selective distribution of molecules of interest to a reaction site (e.g. a biotinylated ZMW base).

In still further embodiments the affinity loading methods described herein can be combined with any other Super Poisson loading methods and/or density loading methods known in the art and described for example in U.S. Pat. No. 8,906,831, U.S. Ser. No. 15/078,915, filed Mar. 23, 2016 and U.S. Ser. No. 62/257,152, filed Nov. 18, 2015, hereby incorporated by reference in their entirety for all purposes and in particular for all teachings related to methods and compositions for loading reaction sites, such as nanoscale wells, with molecules of interest, such as polymerase enzyme-template complexes.

VIII. Compositions

VIII.A. Template Molecules

Any of the methods and complexes described herein can include template nucleic acid molecules (also referred to herein as "template sequences"), often as part of the polymerase enzyme complexes described herein. In general, the template nucleic acid is the molecule for which the complementary sequence is synthesized in the polymerase reaction. In some cases, the template nucleic acid is linear; in some cases, the template nucleic acid is circular. The template nucleic acid can be DNA, RNA, and/or a non-natural RNA or DNA analog. Any template nucleic acid that is suitable for replication by a polymerase enzyme can be used in the methods and systems described herein.

In some embodiments, the template nucleic acids used in methods and compositions of the present invention comprise nucleic acids obtained from a sample. The sample may comprise any number of things, including, but not limited to, bodily fluids (including, but not limited to, blood, urine, serum, lymph, saliva, anal and vaginal secretions, perspiration and semen) and cells of virtually any organism, with mammalian samples being preferred and human samples being particularly preferred; environmental samples (including, but not limited to, air, agricultural, water and soil samples); biological warfare agent samples; research samples (i.e. in the case of nucleic acids, the sample may be the products of an amplification reaction, including both target and signal amplification, such as PCR amplification reactions; purified samples, such as purified genomic DNA, RNA preparations, raw samples (bacteria, virus, genomic DNA, etc.); as will be appreciated by those in the art, virtually any experimental manipulation may have been done on the samples.

In further embodiments, nucleic acid molecules are obtained from a sample and fragmented for use in methods of the invention as template nucleic acids. The fragments may be single or double stranded and may further be modified in accordance with any methods known in the art and described herein. Template nucleic acids may be generated by fragmenting source nucleic acids, such as genomic DNA, using any method known in the art. In one embodiment, shear forces during lysis and extraction of genomic DNA generate fragments in a desired range. Also encompassed by the invention are methods of fragmentation utilizing restriction endonucleases.

As will be appreciated, the template nucleic acids may be generated from a source nucleic acid, such as genomic DNA, by fragmentation to produce fragments of a specific size. The target nucleic acids can be, for example, from about 10 to about 100,000 nucleotides in length, from about 10 to about 50,000 nucleotides in length, or from about 10 to about 20,000 nucleotides in length. In one embodiment, the fragments are 50 to 600 nucleotides in length. In another embodiment, the fragments are 300 to 600 or 200 to 2000 nucleotides in length. In yet another embodiment, the fragments are 10-100, 50-100, 50-300, 100-200, 200-300, 50-400, 100-400, 200-400, 400-500, 400-600, 500-600, 50-1000, 100-1000, 200-1000, 300-1000, 400-1000, 500-1000, 600-1000, 700-1000, 700-900, 700-800, 800-1000, 900-1000, 1500-2000, 1750-2000, and 50-2000 nucleotides in length. In further embodiments, the fragments are at least 5000, 10000, 15000, 20000, 25000, 30000, 40000, 50000, 60000, 70000, 80000, 90000, 100,000, 120,000, 130,000, 140,000, or 150,000 nucleotides in length. In yet further embodiments, the nucleic acid templates are 10-100, 50-100, 50-300, 100-200, 200-300, 50-400, 100-400, 200-400, 400-500, 400-600, 500-600, 50-1000, 100-1000, 200-1000, 300-1000, 400-1000, 500-1000, 600-1000, 700-1000, 700-900, 700-800, 800-1000, 900-1000, 1500-2000, 1750-2000, 50-2000, 100-25000, 200-24000, 300-23000, 400-22000, 500-21000, 600-20000, 700-19000, 800-18000, 900-17000, 1000-16000, 1100-15000, 1200-14000, 1300-13000, 1400-12000, 1500-11000, 1600-10000, 1700-9000, 1800-8000, 1900-7000, 2000-6000, 2100-5000, 2200-4000, 2300-3000, 5000-20000, 10000-30000, 12000-28000, 14000-26000, 16000-24000, 18000-22000, 19000-20000, 20000-40000, or 40000-60000 nucleotides in length. In yet further embodiments, the nucleic acid templates are at least 5000, 10000, 15000, 20000, 25000, 30000, 40000, 50000, 60000, 70000, 80000, 90000, 100,000, 120,000, 130,000, 140,000, or 150,000 nucleotides in length. In further embodiments, the nucleic acid templates are part of polymerase-template complexes. In yet further embodiments, the nucleic acid templates are themselves further hybridized to primers.

In some cases, the template sequence may be a linear single or double stranded nucleic acid sequence. In still other embodiments, the template may be provided as a circular or functionally circular construct that allows redundant processing of the same nucleic acid sequence by the synthesis complex. Use of such circular constructs has been described in, e.g., U.S. Pat. No. 7,315,019 and U.S. patent application Ser. No. 12/220,674, filed Jul. 25, 2008, and alternate functional circular constructs are also described in US Pat. App. Pub. No. 20090298075, the full disclosures of each of which are incorporated herein by reference in their entirety for all purposes and in particular for all teachings related to template nucleic acid constructs. Briefly, such alternate constructs include template sequences that possess a central double stranded portion that is linked at each end by an appropriate linking oligonucleotide, such as a hairpin loop segment. Such structures not only provide the ability to repeatedly replicate a single molecule (and thus sequence that molecule), but also provide for additional redundancy by replicating both the sense and antisense portions of the double stranded portion. In the context of sequencing applications, such redundant sequencing provides great advantages in terms of sequence accuracy.

In further aspects, the template nucleic acid used in the compositions of the present invention includes: a double stranded nucleic acid segment having a first and second end; a first hairpin oligonucleotide connecting each strand of the single template nucleic acid at the first end; a second hairpin oligonucleotide connecting each strand of the single template nucleic acid at the second end. In some embodiments, the first hairpin and second hairpin oligonucleotide are identical. In other embodiments, the first hairpin and second hairpin oligonucleotides are not identical—in other words, the template nucleic acid, despite being an alternate circular construct, is nevertheless asymmetrical. In further embodiments, the first hairpin oligonucleotide includes a primer binding site whereas the second hairpin oligonucleotide includes a capture adapter (or vice versa). The capture adapter is generally of a sequence that can be used to enrich a population for the hairpins of choice—for example, in some embodiments, the capture adapter comprises a polyA sequence, thereby allowing capture using beads or column chromatography utilizing polyT sequences. In other embodiments, the capture adapter comprises at least one methoxy residue. In further embodiments, the capture adapter is complementary to an oligonucleotide attached to a bead, which can in further embodiments be a magnetic bead that can be used to enrich a population for template nucleic acids containing the capture adapter. In some embodiments in which the population of templates includes templates with different adapters or in which each template comprises a different adapter at each end, different beads can be used which contain oligonucleotides complementary to the different adapters. Thus, for templates with two different adapters, two different beads can be used. For populations containing a plurality of different adapters, a concomitant number of different types of beads can be used that are directed to those adapters. In other embodiments, the same bead can contain different oligonucleotides complementary to the different adapters in the population of templates, such that the same bead can capture different adapters (and their associated templates).

In still further embodiments, the first or second hairpin comprises a self-primed adapter sequence in which the primer is part of the adapter. In such embodiments, an additional oligonucleotide primer is not needed to allow a polymerase molecule to begin replicating the template.

In yet further embodiments, the nucleic acid template contains only a single hairpin at one end or the other.

VIII.B. Nucleotides and Nucleotide Analogs

Nucleotides of use in the present invention include, e.g., naturally occurring nucleotides such as dATP, dCTP, dGTP, and dTTP. Various nucleotide analogs are also of use in the present invention. Upon incorporation into a growing oligonucleotide chain, the analog can leave a residue that is the same as or different than a natural nucleotide in the growing oligonucleotide (the polymerase can incorporate any non-standard moiety of the analog, or can cleave it off during incorporation into the oligonucleotide). A "nucleotide analog" herein is a compound, that, in a particular application, functions in a manner similar or analogous to a naturally occurring nucleoside triphosphate (a "nucleotide"), and does not otherwise denote any particular structure. A nucleotide analog is an analog other than a standard naturally occurring nucleotide, i.e., other than A, G, C, T, or U, though upon incorporation into the oligonucleotide, the resulting residue in the oligonucleotide can be the same as (or different from) an A, G, C, T, or U residue.

In one useful aspect of the invention, nucleotide analogs can be modified to achieve any of the improved properties desired. For example, various linkers or other substituents can be incorporated into analogs that have the effect of reducing branching fraction, improving processivity, or altering rates. Modifications to the analogs can include extending the phosphate chains, e.g., to include a tetra-, penta-, hexa- or heptaphosphate group, and/or adding chemical linkers to extend the distance between the nucleotide base and the dye molecule, e.g., a fluorescent dye molecule. Substitution of one or more non-bridging oxygen in the polyphosphate, for example with S or $BH_3$, can change the polymerase reaction kinetics, e.g., to achieve a system having two slow steps as described hereinbelow. Optionally, one or more, two or more, three or more, or four or more non-bridging oxygen atoms in the polyphosphate group of the analog has an S substituted for an O. While not being bound by theory, it is believed that the properties of the nucleotide, such as the metal chelation properties, electronegativity, or steric properties, can be altered by substitution of the non-bridging oxygen(s).

Many nucleotide analogs are available and can be incorporated by polymerases. These include analog structures with core similarity to naturally occurring nucleotides, such as those that comprise one or more substituent on a phosphate, sugar, or base moiety of the nucleoside or nucleotide relative to a naturally occurring nucleoside or nucleotide. In one embodiment, the nucleotide analog includes three phosphate containing groups; for example, the analog can be a labeled nucleoside triphosphate analog and/or an α-thiophosphate nucleotide analog having three phosphate groups. In one embodiment, a nucleotide analog can include one or more extra phosphate containing groups, relative to a nucleoside triphosphate. For example, a variety of nucleotide analogs that comprise, e.g., from 4-6 or more phosphates are described in detail in US patent application publication 2007-0072196, incorporated herein by reference in its entirety for all purposes. Other exemplary useful analogs, including tetraphosphate and pentaphosphate analogs, are described in U.S. Pat. No. 7,041,812, incorporated herein by reference in its entirety for all purposes.

For example, the analog can include a labeled compound of the formula:

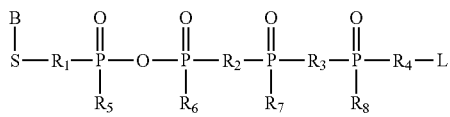

wherein B is a nucleobase (and optionally includes a label); S is selected from a sugar moiety, an acyclic moiety or a carbocyclic moiety (and optionally includes a label); L is an optional detectable label; $R_1$ is selected from O and S; $R_2$, $R_3$ and $R_4$ are independently selected from O, NH, S, methylene, substituted methylene, C(O), C($CH_2$), $CNH_2$, $CH_2CH_2$, and C(OH)$CH_2$R where R is 4-pyridine or 1-imidazole, provided that $R_4$ may additionally be selected from

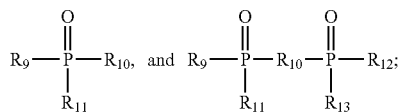

$R_5$, $R_6$, $R_7$, $R_8$, $R_{11}$ and $R_{13}$ are, when present, each independently selected from O, $BH_3$, and S; and $R_9$, $R_{10}$ and $R_{12}$ are independently selected from O, NH, S, methylene, substituted methylene, $CNH_2$, $CH_2CH_2$, and C(OH)$CH_2$R where R is 4-pyridine or 1-imidazole. In some cases, phosphonate analogs may be employed as the analogs, e.g., where one of $R_2$, $R_3$, $R_4$, $R_9$, $R_{10}$ or $R_{12}$ are not O, e.g., they are methyl etc. See, e.g., US patent application publication 2007-0072196, previously incorporated herein by reference in its entirety for all purposes.

The base moiety incorporated into the analog is generally selected from any of the natural or non-natural nucleobases or nucleobase analogs, including, e.g., purine or pyrimidine bases that are routinely found in nucleic acids and available nucleic acid analogs, including adenine, thymine, guanine, cytosine, uracil, and in some cases, inosine. As noted, the base optionally includes a label moiety. For convenience, nucleotides and nucleotide analogs are generally referred to based upon their relative analogy to naturally occurring nucleotides. As such, an analog that operates, functionally, like adenosine triphosphate, may be generally referred to herein by the shorthand letter A. Likewise, the standard abbreviations of T, G, C, U and I, may be used in referring to analogs of naturally occurring nucleosides and nucleotides typically abbreviated in the same fashion. In some cases, a base may function in a more universal fashion, e.g., functioning like any of the purine bases in being able to hybridize with any pyrimidine base, or vice versa. The base moieties used in the present invention may include the conventional bases described herein or they may include such bases substituted at one or more side groups, or other fluorescent bases or base analogs, such as 1,N6 ethenoadenosine or pyrrolo C, in which an additional ring structure renders the B group neither a purine nor a pyrimidine. For example, in certain cases, it may be desirable to substitute one or more side groups of the base moiety with a labeling group or a component of a labeling group, such as one of a donor or acceptor fluorophore, or other labeling group. Examples of labeled nucleobases and processes for labeling such groups are described in, e.g., U.S. Pat. Nos. 5,328,824 and 5,476,928, each of which is incorporated herein by reference in its entirety for all purposes.

In the analogs, the S group is optionally a sugar moiety that provides a suitable backbone for a synthesizing nucleic acid strand. For example, the sugar moiety is optionally selected from a D-ribosyl, 2' or 3' D-deoxyribosyl, 2',3'-D-dideoxyribosyl, 2',3'-D-didehydrodideoxyribosyl, 2' or 3' alkoxyribosyl, 2' or 3' aminoribosyl, 2' or 3' mercaptoribosyl, 2' or 3' alkothioribosyl, acyclic, carbocyclic or other modified sugar moieties. A variety of carbocyclic or acyclic moieties can be incorporated as the "S" group in place of a sugar moiety, including, e.g., those described in U.S. Patent Application Publication No. 2003/0124576, which is incorporated herein by reference in its entirety for all purposes.

For most cases, the phosphorus containing chain in the analogs, e.g., a triphosphate in conventional NTPs, is preferably coupled to the 5' hydroxyl group, as in natural nucleoside triphosphates. However, in some cases, the phosphorus containing chain is linked to the S group by the 3' hydroxyl group.

L generally refers to a detectable labeling group that is coupled to the terminal phosphorus atom via the $R_4$ (or $R_{10}$ or $R_{12}$ etc.) group. The labeling groups employed in the analogs of the invention may comprise any of a variety of detectable labels. Detectable labels generally denote a chemical moiety that provides a basis for detection of the analog compound separate and apart from the same compound lacking such a labeling group. Examples of labels include, e.g., optical labels, e.g., labels that impart a detectable optical property to the analog, electrochemical labels, e.g., labels that impart a detectable electrical or electrochemical property to the analog, and physical labels, e.g., labels that impart a different physical or spatial property to the analog, e.g., a mass tag or molecular volume tag. In some cases, individual labels or combinations may be used that impart more than one of the aforementioned properties to the analogs of the invention.

Optionally, the labeling groups incorporated into the analogs comprise optically detectable moieties, such as luminescent, chemiluminescent, fluorescent, fluorogenic, chromophoric and/or chromogenic moieties, with fluorescent and/or fluorogenic labels being preferred. A variety of different label moieties are readily employed in nucleotide analogs. Such groups include, e.g., fluorescein labels, rhodamine labels, cyanine labels (i.e., Cy3, Cy5, and the like, generally available from the Amersham Biosciences division of GE Healthcare), and the Alexa family of fluorescent dyes and other fluorescent and fluorogenic dyes available from Molecular Probes/Invitrogen, Inc. and described in 'The Handbook—A Guide to Fluorescent Probes and Labeling Technologies, Eleventh Edition' (2010) (available from Invitrogen, Inc./Molecular Probes). A variety of other fluorescent and fluorogenic labels for use with nucleoside polyphosphates, and which would be applicable to the nucleotide analogs incorporated by the polymerases of the present invention, are described in, e.g., U.S. Patent Application Publication No. 2003/0124576, previously incorporated herein by reference in its entirety for all purposes.

Thus, in one illustrative example, the analog can be a phosphate analog (e.g., an analog that has more than the typical number of phosphates found in nucleoside triphosphates) that includes, e.g., an Alexa dye label. For example, an Alexa488 dye can be labeled on a delta phosphate of a tetraphosphate analog (denoted, e.g., A488dC4P or A488dA4P, for the Alexa488 labeled tetraphosphate analogs of C and A, respectively), or an Alexa568 or Alexa633 dye can be used (e.g., A568dC4P and A633dC4P, respectively, for labeled tetraphosphate analogs of C or A568dT6P for a labeled hexaphosphate analog of T), or an Alexa546 dye can be used (e.g., A546dG4P), or an Alexa594 dye can be used (e.g., A594dT4P). As additional examples, an Alexa555 dye (e.g., A555dC6P or A555dA6P), an Alexa 647 dye (e.g., A647dG6P), an Alexa 568 dye (e.g., A568dT6P), and/or an Alexa660 dye (e.g., A660dA6P or A660dC6P) can be used in, e.g., single molecule sequencing. Similarly, to facilitate color separation, a pair of fluorophores exhibiting FRET (fluorescence resonance energy transfer) can be labeled on a delta phosphate of a tetraphosphate analog (denoted, e.g., FAM-amb-A532dG4P or FAM-amb-A594dT4P).

As noted above, an analog can include a linker that extends the distance between the nucleotide base and the label moiety, e.g., a fluorescent dye moiety. Exemplary linkers and analogs are described in U.S. Pat. No. 7,968,702. Similarly, a protein or other moiety can be employed to provide spacing and/or shielding between the base and the label, e.g., as described in U.S. patent application Ser. No. 13/767,619 "Polymerase Enzyme Substrates with Protein Shield" filed Feb. 14, 2013, and U.S. patent application Ser. No. 14/452,497 "Protected Fluorescent Reagent Compounds" filed Aug. 5, 2013. Suitable polymerase substrates optionally include two or more nucleoside polyphosphates and/or two or more label moieties, e.g., as described in U.S. patent application Ser. No. 13/767,619 "Polymerase Enzyme Substrates with Protein Shield," U.S. patent application Ser. No. 14/452,497 "Protected Fluorescent Reagent Compounds," and US patent application publication 2009-0208957 Alternate Labeling Strategies for Single Molecule Sequencing.

Additional details regarding labels, analogs, and methods of making such analogs can be found in US patent application publication 2007-0072196, WO 2007/041342 Labeled Nucleotide Analogs and Uses Therefor, WO 2009/114182 Labeled Reactants and Their Uses, US patent application publication 2009-0208957 Alternate Labelling Strategies for Single Molecule Sequencing, U.S. patent application Ser. No. 13/218,412 Functionalized Cyanine Dyes, U.S. patent application Ser. No. 13/218,395 Functionalized Cyanine Dyes, U.S. patent application Ser. No. 13/218,428 Cyanine Dyes, U.S. patent application Ser. No. 13/218,382 Scaffold-Based Polymerase Enzyme Substrates, US patent application publication 2010-0167299 Phospholink Nucleotides for Sequencing Applications, US patent application publication 2010-0152424 Modular Nucleotide Compositions and Uses Therefor, U.S. patent application Ser. No. 13/767,619 "Polymerase Enzyme Substrates with Protein Shield," and U.S. patent application Ser. No. 14/452,497 "Protected Fluorescent Reagent Compounds," each of which is incorporated herein by reference in its entirety for all purposes.

VIII.C. Polymerases

The methods and compositions of the present disclosure utilize polymerase enzymes (also referred to herein as "polymerases"). Any suitable polymerase enzyme can be used in the systems and methods disclosed herein. Suitable polymerases include DNA dependent DNA polymerases, DNA dependent RNA polymerases, RNA dependent DNA polymerases (reverse transcriptases), and RNA dependent RNA polymerases. In certain embodiments, the polymerases used in the methods and compositions of the present invention are strand-displacing polymerases.

As disclosed in further detail herein, polymerases of use in the presently disclosed methods may include modifications that improve certain characteristics of the enzyme, including processivity, resistance to photodamage, and conduciveness to immobilization. In certain aspects, polymerases used in the methods and systems disclosed herein include a linker through which the polymerases (and any other molecules they are complexed with, such as template nucleic acids and optionally replication initiating moieties) can be immobilized onto a surface. In certain aspects, these linkers are resistant to cleavage by a protease. Such linkers can be designed in conjunction with choices made for protease treatment methods. For example, for the loading methods described herein that utilize the protease trypsin, polymerases of use in such methods can be designed to include linkers that are resistant to digestion by trypsin, e.g., peptide linkers that contain no lysine or arginine side chains, which are recognition sites for trypsin activity.

DNA polymerases are sometimes classified into six main groups based upon various phylogenetic relationships, e.g., with *E. coli* Pol I (class A), *E. coli* Pol II (class B), *E. coli* Pol III (class C), Euryarchaeotic Pol II (class D), human Pol beta (class X), and *E. coli* UmuC/DinB and eukaryotic RAD30/xeroderma pigmentosum variant (class Y). For a review of recent nomenclature, see, e.g., Burgers et al. (2001) "Eukaryotic DNA polymerases: proposal for a revised nomenclature" J Biol Chem. 276(47):43487-90. For a review of polymerases, see, e.g., Hübscher et al. (2002) "Eukaryotic DNA Polymerases" Annual Review of Biochemistry Vol. 71: 133-163; Alba (2001) "Protein Family Review: Replicative DNA Polymerases" Genome Biology 2(1):reviews 3002.1-3002.4; and Steitz (1999) "DNA polymerases: structural diversity and common mechanisms" J Biol Chem 274:17395-17398. The basic mechanisms of action for many polymerases have been determined. The sequences of literally hundreds of polymerases are publicly available, and the crystal structures for many of these have been determined, or can be inferred based upon similarity to solved crystal structures of homologous polymerases. For example, the crystal structure of φ29, a preferred type of parental enzyme to be modified according to the invention, is available.

In addition to wild-type polymerases, chimeric polymerases made from a mosaic of different sources can be used. For example, φ29 polymerases made by taking sequences from more than one parental polymerase into account can be used as a starting point for mutation to produce the polymerases of the invention. Chimeras can be produced, e.g., using consideration of similarity regions between the polymerases to define consensus sequences that are used in the chimera, or using gene shuffling technologies in which multiple φ29-related polymerases are randomly or semi-randomly shuffled via available gene shuffling techniques (e.g., via "family gene shuffling"; see Crameri et al. (1998) "DNA shuffling of a family of genes from diverse species accelerates directed evolution" Nature 391:288-291; Clackson et al. (1991) "Making antibody fragments using phage display libraries" Nature 352:624-628; Gibbs et al. (2001) "Degenerate oligonucleotide gene shuffling (DOGS): a method for enhancing the frequency of recombination with family shuffling" Gene 271:13-20; and Hiraga and Arnold (2003) "General method for sequence-independent site-directed chimeragenesis: J. Mol. Biol. 330:287-296). In these methods, the recombination points can be predetermined such that the gene fragments assemble in the correct order. However, the combinations, e.g., chimeras, can be formed at random. For example, using methods described in Clarkson et al., five gene chimeras, e.g., comprising segments of a Phi29 polymerase, a PZA polymerase, an M2 polymerase, a B103 polymerase, and a GA-1 polymerase, can be generated. Appropriate mutations to improve branching fraction, increase closed complex stability, or alter reaction rate constants can be introduced into the chimeras.

Available DNA polymerase enzymes have also been modified in any of a variety of ways, e.g., to reduce or eliminate exonuclease activities (many native DNA polymerases have a proof-reading exonuclease function that interferes with, e.g., sequencing applications), to simplify production by making protease digested enzyme fragments such as the Klenow fragment recombinant, etc. As noted, polymerases have also been modified to confer improvements in specificity, processivity, and improved retention time of labeled nucleotides in polymerase-DNA-nucleotide complexes (e.g., WO 2007/076057 Polymerases For Nucleotide Analogue Incorporation by Hanzel et al. and WO 2008/051530 Polymerase Enzymes And Reagents For Enhanced Nucleic Acid Sequencing by Rank et al.), to alter branch fraction and translocation (e.g., US Pub. No. 20100075332 entitled "Engineering Polymerases And Reaction Conditions For Modified Incorporation Properties"), to increase photostability (e.g., US Pub. No. 20100093555 entitled "Enzymes Resistant to Photodamage"), and to improve surface-immobilized enzyme activities (e.g., WO 2007/075987 Active Surface Coupled Polymerases by Hanzel et al. and WO 2007/076057 Protein Engineering Strategies To Optimize Activity Of Surface Attached Proteins by Hanzel et al.). In some cases, the polymerase is modified in order to more effectively incorporate desired nucleotide analogs, e.g. analogs having four or more phosphates in their polyphosphate chain. Enzymes mutated to more readily accept nucleotide analogs having such properties are described, for example in the applications described above and in US 20120034602—Recombinant Polymerases for Improved Single Molecule Sequencing; US 20100093555—Enzymes Resistant to Photodamage; US 20110189659—Generation of Modified Polymerases for Improved Accuracy in Single Molecule Sequencing; US 20100112645—Generation of Modified Polymerases for Improved Accuracy in Single Molecule Sequencing; US 2008/0108082-Polymerase enzymes and reagents for enhanced nucleic acid sequencing; and US 20110059505—Polymerases for Nucleotide Analogue Incorporation which are incorporated herein by reference in their entirety for all purposes.

Many polymerases that are suitable for modification are available, e.g., for use in sequencing, labeling and amplification technologies. For example, human DNA Polymerase Beta is available from R&D systems. DNA polymerase I is available from Epicenter, GE Health Care, Invitrogen, New England Biolabs, Promega, Roche Applied Science, Sigma Aldrich and many others. The Klenow fragment of DNA Polymerase I is available in both recombinant and protease digested versions, from, e.g., Ambion, Chimerx, eEnzyme LLC, GE Health Care, Invitrogen, New England Biolabs, Promega, Roche Applied Science, Sigma Aldrich and many others. φ29 DNA polymerase is available from e.g., Epicentre. Poly A polymerase, reverse transcriptase, Sequenase, SP6 DNA polymerase, T4 DNA polymerase, T7 DNA polymerase, and a variety of thermostable DNA polymerases (Taq, hot start, titanium Taq, etc.) are available from a variety of these and other sources. Recent commercial DNA polymerases include Phusion™ High-Fidelity DNA Polymerase, available from New England Biolabs; GoTaq® Flexi DNA Polymerase, available from Promega; RepliPHI™ φ29 DNA Polymerase, available from Epicentre Biotechnologies; PfuUltra™ Hotstart DNA Polymerase, available from Stratagene; KOD HiFi DNA Polymerase, available from Novagen; and many others. Biocompare(dot)com provides comparisons of many different commercially available polymerases.

DNA polymerases that are preferred substrates for mutation to improve desired properties (e.g., for use in single molecule sequencing, include, e.g. Taq polymerases, exonuclease deficient Taq polymerases, E. coli DNA Polymerase 1, Klenow fragment, reverse transcriptases, φ29-related polymerases including wild type φ29 polymerase and derivatives of such polymerases such as exonuclease deficient forms, T7 DNA polymerase, T5 DNA polymerase, an RB69 polymerase, etc.

In one aspect, the polymerase of use in the methods and compositions described herein is a modified φ29-type DNA polymerase. For example, the modified recombinant DNA polymerase can be homologous to a wild-type or exonuclease deficient φ29 DNA polymerase, e.g., as described in U.S. Pat. Nos. 5,001,050, 5,198,543, or 5,576,204. Alternately, the modified recombinant DNA polymerase can be homologous to other φ29-type DNA polymerases, such as B103, GA-1, PZA, φ15, BS32, M2Y, Nf, G1, Cp-1, PRD1, PZE, SFS, Cp-5, Cp-7, PR4, PR5, PR722, L17, α21, or the like. For nomenclature, see also, Meijer et al. (2001) "φ29 Family of Phages" Microbiology and Molecular Biology Reviews, 65(2):261-287. Suitable polymerases are described, for example, in U.S. Patent application publications 2007-0196846, 2008-0108082, 2010-0075332, 2010-0093555, 2010-0112645, 2011-0189659, 2012-0034602, 2013-0217007, 2014-0094374, and 2014-0094375.

In further embodiments, the polymerase enzyme used in the methods of the invention includes RNA dependent DNA polymerases or reverse transcriptases. Suitable reverse transcriptase enzymes include HIV-1, M-MLV, AMV, and Telomere Reverse Transcriptase. Reverse transcriptases also allow for the direct sequencing of RNA substrates such as messenger RNA, transfer RNA, non-coding RNA, ribosomal RNA, micro RNA or catalytic RNA.

The polymerase enzymes of use in the present invention generally require a primer. While in most cases an oligonucleotide primer is used, in some cases a protein such as a terminal protein can act as a primer. In other embodiments, self-priming templates are employed. Oligonucleotide primers are generally complementary to a portion of the template nucleic acid. The primers can comprise naturally occurring RNA or DNA oligonucleotides. The primers may also be synthetic analogs. The primers may have alternative backbones as described above for the nucleic acids of the invention. The primer may also have other modifications, such as the inclusion of heteroatoms, the attachment of labels, such as dyes, or substitution with functional groups which will still allow for base pairing and for recognition by the enzyme. Primers can select tighter binding primer sequences, e.g., GC rich sequences, as well as employ primers that include within their structure non-natural nucleotides or nucleotide analogs, e.g., peptide nucleic acids (PNAs) or locked nucleic acids (LNAs), that can demonstrate higher affinity pairing with the template. The primer can also be selected to influence the kinetics of the polymerase reaction.

To reduce or prevent undesired dissociation of the polymerase from the template and primer, the processivity of the polymerase can be increased by locking the template in place in the enzyme, e.g., with chemical cross-links. For example, a bifunctional cross-linker can be reacted with residues in the polymerase on each side of the bound template, topologically encircling the template. See, e.g., U.S. Pat. No. 7,745,116 and US patent application publication 2015/0086994, each of which is incorporated herein by reference in its entirety for all purposes. Cysteine residues can be introduced into the polymerase at suitable positions for cross-link formation. For example, a recombinant φ29 polymerase can include, e.g., A83C and E420C substitutions, D84C and E418C substitutions, V19C and N409C substitutions, and/or N409C and V568C substitutions. (See, e.g., US patent application publication 2014/0094375, incorporated herein by reference in its entirety for all purposes, for the sequence of wild-type φ29 polymerase.) Existing solvent accessible cysteine residues can be mutated to ensure that the cross-link is formed between the desired pair of residues; thus, a suitable recombinant φ29 polymerase can also include one or more substitutions such as, e.g., C106S and/or C448V. Suitable bifunctional linkers are known in the art, for example, a bismaleimide linker, e.g., a bismaleimide-PEG linker, e.g., 1,11-bismaleimido-triethyleneglycol (BM(PEG)$_3$). Other coupling chemistries that can be employed include, e.g., thiol reactive reagents and disulfide containing reagents, e.g., haloacetyl crosslinkers (e.g., linkers including two iodoacetyl/iodoacetamide or bromoacetyl groups) and linkers with two pyridyl disulfide groups. The body of the linker can include, e.g., PEG (polyethylene glycol), an oligopeptide (e.g., polyglycine), or the like. Optimal linker length can be chosen based on the distance between the two residues to be cross-linked, e.g., in a crystal structure or other model of the polymerase. The linker is typically reacted with the polymerase after binding of the template (or primer/template); suitable reaction conditions for various linker chemistries are known in the art. Noncovalent linkers can also be employed. Such topological encirclement of the template by polymerase can be particularly effective for circular templates (including, e.g., simple circles and SMRTbells™ as described in, e.g., U.S. Pat. No. 8,153,375 "Compositions and Methods for Nucleic Acid Sequencing" and Travers et al. (2010) Nucl. Acids Res. 38(15):e159, each of which is incorporated herein by reference in its entirety for all purposes).

Many native DNA polymerases have a proof-reading exonuclease function which can yield substantial data analysis problems in processes that utilize real time observation of incorporation events as a method of identifying sequence information, e.g., single molecule sequencing applications. Even where exonuclease activity does not introduce such problems in single molecule sequencing, reduction of exonuclease activity can be desirable since it can increase accuracy (in some cases at the expense of readlength).

Accordingly, polymerases for use in the above techniques optionally include one or more mutations (e.g., substitutions, insertions, and/or deletions) relative to the parental polymerase that reduce or eliminate endogenous exonuclease activity. For example, relative to wild-type φ29 DNA polymerase, one or more of positions N62, D12, E14, T15, H61, D66, D169, K143, Y148, and H149 is optionally mutated to reduce exonuclease activity in a recombinant φ29 polymerase. Exemplary mutations that can reduce exonuclease activity in a recombinant φ29 polymerase include, e.g., N62D, N62H, D12A, T15I, E14I, E14A, D66A, K143D, D145A and D169A substitutions, as well as addition of an exogenous feature at the C-terminus (e.g., a polyhistidine tag). See, e.g., US patent application publication 2014/0094375, incorporated herein by reference in its entirety for all purposes, for the sequence of wild-type φ29 polymerase.

IX. Applications for Methods and Compositions of the Invention: Sequencing

The methods, devices, and compositions of the invention are particularly useful for single molecule sequencing methods, and specifically single molecule sequencing by incorporation in real time, because the present invention provides a way to efficiently load reaction regions occupied by a single polymerase composition. In general, the high density single molecule loading achieved by methods and compositions described herein allow single molecule analysis to be conducted more efficiently and with greater speed, because there will be fewer "unusable" regions on a substrate surface for the sequencing reaction (i.e., regions that have no or multiple polymerase compositions loaded, which provide either no information (for the empty regions) or sequencing information that must be deconvoluted to account for the multiply loaded molecules).

In some aspects, the present invention includes methods of analyzing the sequence of template nucleic acids associated with the polymerase compositions described herein. In such aspects, the sequence analysis employs template dependent synthesis in identifying the nucleotide sequence of the template nucleic acid. Nucleic acid sequence analysis that employs template dependent synthesis identifies individual bases, or groups of bases, as they are added during a template mediated synthesis reaction, such as a primer extension reaction, where the identity of the base is required to be complementary to the template sequence to which the primer sequence is hybridized during synthesis. Other such processes include ligation driven processes, where oligo- or polynucleotides are complexed with an underlying template sequence, in order to identify the sequence of nucleotides in that sequence. Typically, such processes are enzymatically mediated using nucleic acid polymerases, such as DNA polymerases, RNA polymerases, reverse transcriptases, and the like, or other enzymes such as in the case of ligation driven processes, e.g., ligases.

Sequence analysis using template dependent synthesis can include a number of different processes. For example, in embodiments utilizing sequence by synthesis processes, individual nucleotides or nucleotide analogs are identified iteratively as they are added to the growing primer extension product.

For sequencing processes that rely upon monitoring of the incorporation of nucleotides into growing nascent strands being synthesized by the complex, the progress of the reaction through these steps can of significant importance. In particular, for certain "real-time" nucleotide incorporation monitoring processes, the detectability of the incorporation event is improved based upon the amount of time the nucleotide is incorporated into and retained within the synthesis complex during its ultimate incorporation into a primer extension product. By way of example, in certain exemplary processes, the presence of the nucleotide in the synthesis complex is detected either by virtue of a focused observation of the synthesis complex, or through the use of interactive labeling techniques that produce characteristic signals when the nucleotide is within the synthesis complex. See, e.g., Levene, et al., Science 299:682-686, January 2003, and Eid, J. et al., Science, 323(5910), 133-138 (2009), the full disclosures of which are incorporated herein by reference in their entirety for all purposes.

In further aspects, the methods of the present invention include steps from any single molecule sequencing methods known in the art. See, e.g., Rigler, et al., DNA-Sequencing at the Single Molecule Level, Journal of Biotechnology, 86(3): 161 (2001); Goodwin, P. M., et al., Application of Single Molecule Detection to DNA Sequencing. Nucleosides & Nucleotides, 16(5-6): 543-550 (1997); Howorka, S., et al., Sequence-Specific Detection of Individual DNA Strands using Engineered Nanopores, Nature Biotechnology, 19(7): 636-639 (2001); Meller, A., et al., Rapid Nanopore Discrimination Between Single Polynucleotide Molecules, Proceedings of the National Academy of Sciences of the United States of America, 97(3): 1079-1084 (2000); Driscoll, R. J., et al., Atomic-Scale Imaging of DNA Using Scanning Tunneling Microscopy. Nature, 346(6281): 294-296 (1990).

In further embodiments, methods of single molecule sequencing known in the art include detecting individual nucleotides as they are incorporated into a primed template, i.e., sequencing by synthesis. Such methods often utilize exonucleases to sequentially release individual fluorescently labeled bases as a second step after DNA polymerase has formed a complete complementary strand. See Goodwin et al., "Application of Single Molecule Detection to DNA Sequencing," Nucleos. Nucleot. 16: 543-550 (1997).

In general, for sequencing methods utilizing compositions of the present invention, individual polymerase compositions are provided within separate discrete regions of a support. For example, in some cases, individual complexes may be provided within individual confinement structures, including nanoscale structures such as nanoscale wells. In further examples, zero-mode waveguide cores or any of the reaction chambers discussed above in the stepwise sequencing section serve as the reaction regions for sequencing methods utilizing compositions of the present invention. Examples of waveguides and processes for immobilizing individual complexes therein are described in, e.g., Published International Patent Application No. WO 2007/123763, the full disclosure of which is incorporated herein by reference in its entirety for all purposes and in particular for all teachings related to providing individual complexes into individual confinement structures. In some cases the molecules of interest (e.g., polymerase/template complexes) can be provided onto or proximal to structures or regions that allow for electronic single molecule sequencing. Such structures can include nanoscale electronic structures such as electrodes, capacitors, or field effect transducers (nanoFETs). NanoFETs include those having carbon nanotube gates. Such structures and their use for single molecule sequencing are described, for example, in U.S. Patent Application Publication No. 2015/0065353 which is incorporated herein in its entirety for all purposes and in particular for all teachings related to structures for use in single molecule sequencing.

Incorporation of labeled nucleotide analogs by polymerases is particularly useful in a variety of different nucleic acid analyses, including real-time monitoring of DNA polymerization. The label can itself be incorporated, or more preferably, can be released during incorporation of the analog. For example, analog incorporation can be monitored in real time by monitoring label release during incorporation of the analog by the polymerase. The portion of the analog that is incorporated can be the same as a natural nucleotide, or can include features of the analog that differ from a natural nucleotide.

In general, label incorporation or release can be used to indicate the presence and composition of a growing nucleic acid strand, e.g., providing evidence of template replication/amplification and/or sequence of the template. Signaling from the incorporation can be the result of detecting labeling groups that are liberated from the incorporated analog, e.g., in a solid phase assay, or can arise upon the incorporation reaction. For example, in the case of FRET labels where a bound label is quenched and a free label is not, release of a label group from the incorporated analog can give rise to a fluorescent signal. Alternatively, the enzyme may be labeled with one member of a FRET pair proximal to the active site, and incorporation of an analog bearing the other member will allow energy transfer upon incorporation. The use of enzyme bound FRET components in nucleic acid sequencing applications is described, e.g., in U.S. Patent Application Publication No. 2003/0044781, incorporated herein by reference.

In one example reaction of interest, a polymerase reaction can be isolated within an extremely small observation volume that effectively results in observation of individual polymerase molecules. As a result, the incorporation event provides observation of an incorporating nucleotide analog that is readily distinguishable from non-incorporated nucleotide analogs. In a preferred aspect, such small observation volumes are provided by immobilizing the polymerase enzyme within an optical confinement, such as a Zero Mode Waveguide (ZMW). For a description of ZMWs and their application in single molecule analyses, and particularly nucleic acid sequencing, see, e.g., U.S. Patent Application Publication No. 2003/0044781 and U.S. Pat. No. 6,917,726, each of which is incorporated herein by reference in its entirety for all purposes. See also Levene et al. (2003) "Zero-mode waveguides for single-molecule analysis at high concentrations" Science 299:682-686, Eid et al. (2009) "Real-time DNA sequencing from single polymerase molecules" Science 323:133-138, and U.S. Pat. Nos. 7,056,676, 7,056,661, 7,052,847, and 7,033,764, the full disclosures of which are incorporated herein by reference in their entirety for all purposes.

In general, a polymerase enzyme is complexed with the template strand in the presence of one or more nucleotides and/or one or more nucleotide analogs. For example, in certain embodiments, labeled analogs are present representing analogous compounds to each of the four natural nucleotides, A, T, G and C, e.g., in separate polymerase reactions, as in classical Sanger sequencing, or multiplexed together, e.g., in a single reaction, as in multiplexed sequencing approaches. When a particular base in the template strand is encountered by the polymerase during the polymerization reaction, it complexes with an available analog that is complementary to such nucleotide, and incorporates that analog into the nascent and growing nucleic acid strand. In one aspect, incorporation can result in a label being released, e.g., in polyphosphate analogs, cleaving between the α and β phosphorus atoms in the analog, and consequently releasing the labeling group (or a portion thereof). The incorporation event is detected, either by virtue of a longer presence of the analog and, thus, the label, in the complex, or by virtue of release of the label group into the surrounding medium. Where different labeling groups are used for each of the types of analogs, e.g., A, T, G or C, identification of a label of an incorporated analog allows identification of that analog and consequently, determination of the complementary nucleotide in the template strand being processed at that time. Sequential reaction and monitoring permits real-time monitoring of the polymerization reaction and determination of the sequence of the template nucleic acid. As noted above, in particularly preferred aspects, the polymerase enzyme/template complex is provided immobilized within an optical confinement that permits observation of an individual complex, e.g., a zero mode waveguide. For additional information on single molecule sequencing monitoring incorporation of phosphate-labeled analogs in real time, see, e.g., Eid et al. (2009) "Real-time DNA sequencing from single polymerase molecules" Science 323:133-138.

In a first exemplary technique, a nucleic acid synthesis complex, including a polymerase enzyme, a template sequence and a complementary primer sequence, is provided immobilized within an observation region that permits illumination and observation of a small volume that includes the complex without excessive illumination of the surrounding volume. By illuminating and observing only the volume immediately surrounding the complex, one can readily identify fluorescently labeled nucleotides that become incorporated during that synthesis, as such nucleotides are retained within that observation volume by the polymerase for longer periods than those nucleotides that are simply randomly diffusing into and out of that volume. In particular, when a nucleotide is incorporated into DNA by the polymerase, it is retained within the observation volume for a prolonged period of time, and upon continued illumination yields a prolonged fluorescent signal. By comparison, randomly diffusing and not incorporated nucleotides remain within the observation volume for much shorter periods of time, and thus produce only transient signals, many of which go undetected due to their extremely short duration.

In particularly preferred exemplary systems, the confined illumination volume is provided through the use of arrays of optically confined apertures termed zero mode waveguides (ZMWs). See, e.g., U.S. Pat. No. 6,917,726, which is incorporated herein by reference in its entirety for all purposes. For sequencing applications, the DNA polymerase is typically provided immobilized upon the bottom of the ZMW, although another component of the complex (e.g., a primer or template) is optionally immobilized on the bottom of the ZMW to localize the complex. See, e.g., Korlach et al. (2008) PNAS U.S.A. 105(4):1176-1181 and US patent application publication 2008-0032301, each of which is incorporated herein by reference in its entirety for all purposes.

In operation, the fluorescently labeled nucleotides (e.g., analogs corresponding to A, C, G and T) bear one or more fluorescent dye groups on a terminal phosphate moiety that is cleaved from the nucleotide upon incorporation. As a result, synthesized nucleic acids do not bear the build-up of fluorescent labels, as the labeled polyphosphate groups diffuse away from the complex following incorporation of the associated nucleotide, nor do such labels interfere with the incorporation event. See, e.g., Korlach et al. (2008) Nucleosides, Nucleotides and Nucleic Acids 27:1072-1083.

In a second exemplary technique, the immobilized complex and the nucleotides to be incorporated are each provided with interactive labeling components. Upon incorporation, the nucleotide borne labeling component is brought into sufficient proximity to the complex borne (or complex proximal) labeling component, such that these components produce a characteristic signal event. For example, the polymerase may be provided with a fluorophore that provides fluorescent resonant energy transfer (FRET) to appropriate acceptor fluorophores. These acceptor fluorophores are provided upon the nucleotide to be incorporated, where each type of nucleotide bears a different acceptor fluorophore, e.g., that provides a different fluorescent signal. Upon incorporation, the donor and acceptor are brought close enough together to generate energy transfer signal. By providing different acceptor labels on the different types of nucleotides, one obtains a characteristic FRET-based fluorescent signal for the incorporation of each type of nucleotide, as the incorporation is occurring.

In a related aspect, a nucleotide analog may include two interacting fluorophores that operate as a donor/quencher pair, where one member is present on the nucleobase or other retained portion of the nucleotide, while the other member is present on a phosphate group or other portion of the nucleotide that is released upon incorporation, e.g., a terminal phosphate group. Prior to incorporation, the donor and quencher are sufficiently proximal on the same analog as to provide characteristic signal quenching. Upon incorporation and cleavage of the terminal phosphate groups, e.g., bearing a donor fluorophore, the quenching is removed and the resulting characteristic fluorescent signal of the donor is observable.

In exploiting the foregoing processes, where the incorporation reaction occurs too rapidly, it may result in the incorporation event not being detected, i.e., the event speed exceeds the detection speed of the monitoring system. The missed detection of incorporated nucleotides can lead to an increased rate of errors in sequence determination, as omissions in the real sequence. In order to mitigate the potential for missed pulses due to short reaction or product release times, in one aspect, the current invention can result in increased reaction and/or product release times during incorporation cycles. Similarly, very short interpulse distances can occasionally cause pulse merging. An advantage of employing polymerases with reduced reaction rates, e.g., polymerases exhibiting decreased rates and/or two slow-step kinetics as described in US patent application publications 2009-0286245 and 2010-0112645, is an increased frequency of longer, detectable, binding events. This advantage may also be seen as an increased ratio of longer, detectable pulses to shorter, non-detectable pulses, where the pulses represent binding events.

The sequencing processes, e.g., using the substrates described above and the compositions of the invention, are generally exploited in the context of a fluorescence optical system that is capable of illuminating the various complexes on the substrate, and obtaining, detecting and separately recording fluorescent signals from these complexes. Such systems typically employ one or more illumination sources that provide excitation light of appropriate wavelength(s) for the labels being used. An optical train directs the excitation light at the reaction region(s) and collects emitted fluorescent signals and directs them to an appropriate detector or detectors. Additional components of the optical train can provide for separation of spectrally different signals, e.g., from different fluorescent labels, and direction of these separated signals to different portions of a single detector or to different detectors. Other components may provide for spatial filtering of optical signals, focusing and direction of the excitation and or emission light to and from the substrate. An exemplary system is also described in Lundquist et al., Published U.S. Patent Application No. 2007-0036511, Optics Letters, Vol. 33, Issue 9, pp. 1026-1028, the full disclosure of which is incorporated herein by reference in its entirety for all purposes.

Fluorescence reflective optical trains can be used in the applications of the systems of the invention. For a discussion on the advantages of such systems, see, e.g., U.S. patent application Ser. No. 11/704,689, filed Feb. 9, 2007, Ser. No. 11/483,413, filed Jul. 7, 2006, and Ser. No. 11/704,733, filed Feb. 9, 2007, the full disclosures of which are incorporated herein by reference in their entirety for all purposes.

In the context of the nucleic acid sequencing methods described herein, it will be appreciated that the signal sources each represent sequencing reactions, and particularly, polymerase mediated, template dependent primer extension reactions, where in preferred aspects, each base incorporation event results in a prolonged illumination (or localization) of one of four differentially labeled nucleotides being incorporated, so as to yield a recognizable pulse (peak) that carries a distinguishable spectral profile or color.

In further embodiments, compositions of the present invention are utilized in sequencing methods utilizing nanopores. In exemplary embodiments, enzymes are loaded into a nanopore—the nanopore comprises binding moieties complementary to reaction moieties on the enzyme (or another molecule associated with the enzyme, e.g., a template). In this way, a single enzyme is loaded into each nanopore. In certain embodiments, the enzymes are attached proximal to the nanopore. As will be appreciated, helicases and exonucleases as well as polymerases can be used in nanopore sequencing and can be loaded by the techniques described herein. Methods of nanopore sequencing are known in the art and disclosed for example in US Published App. Nos. 2013/0327644 and 2014/0051068, which are hereby incorporated by reference for all purposes and in particular for all teachings, written description, figures and figure legends related to nanopore sequencing.

The present invention can further include computer implemented processes, and/or software incorporated onto a computer readable medium instructing such processes, as set forth in greater detail below. As such, signal data generated by the reactions and optical systems described above, is input or otherwise received into a computer or other data processor, and subjected to one or more of the various process steps or components set forth below. Once these processes are carried out, the resulting output of the computer implemented processes may be produced in a tangible or observable format, e.g., printed in a user readable report, displayed upon a computer display, or it may be stored in one or more databases for later evaluation, processing, reporting or the like, or it may be retained by the computer or transmitted to a different computer for use in configuring subsequent reactions or data processes.

Computers for use in carrying out the processes of the invention can range from personal computers such as PC or Macintosh® type computers running Intel Pentium or Duo-Core processors, to workstations, laboratory equipment, or high speed servers, running UNIX, LINUX, Windows®, or other systems. Logic processing of the invention may be performed entirely by general purposes logic processors (such as CPU's) executing software and/or firmware logic instructions; or entirely by special purposes logic processing circuits (such as ASICs) incorporated into laboratory or diagnostic systems or camera systems which may also include software or firmware elements; or by a combination of general purpose and special purpose logic circuits. Data formats for the signal data may comprise any convenient format, including digital image based data formats, such as JPEG, GIF, BMP, TIFF, or other convenient formats, while video based formats, such as avi, mpeg, mov, rmv, or other video formats may be employed. The software processes of the invention may generally be programmed in a variety of programming languages including, e.g., Matlab, C, C++, C#, NET, Visual Basic, Python, JAVA, CGI, and the like.

In some cases, the compositions, methods, and systems of the invention can be used as part of an integrated sequencing system, for example, as described in US 20120014837—Illumination of Integrated Analytical Systems, US 20120021525—Optics Collection and Detection System and Method, US 20120019828—Integrated Analytical System and Method, 61/660,776 filed Jun. 17, 2012—Arrays of Integrated Analytical Devices and Methods for Production, and US 20120085894—Substrates and Optical Systems and Methods of Use Thereof which are incorporated herein by reference in their entirety for all purposes.

In certain embodiments, the sequencing compositions described herein will be provided in whole, or in part, in kit form enabling one to carry out the processes described herein. Such kits will typically comprise one or more components of the reaction complex, such as the polymerase enzyme and primer sequences. Such kits will also typically include buffers and reagents for loading of the polymerase and/or a template as in the processes described herein. The kits will also optionally include other components for carrying out sequencing applications in accordance with those methods described herein. In particular, such kits may include ZMW array substrates for use in observing individual reaction complexes as described herein.

In addition to the various components set forth above, the kits will typically include instructions for combining the various components in the amounts and/or ratios set forth herein, to carry out the desired processes, as also described or referenced herein, e.g., for performing sequence by incorporation reactions.

X. Substrates and Surfaces

Substrates of use in particular sequencing methods of the invention are known in the art and discussed herein, and as will be appreciated, any of the substrates discussed herein can be used in any combination for any embodiments discussed herein.

In exemplary embodiments, methods of sequencing of the invention utilize substrates that include one or more reaction regions (also referred to herein as "reaction chambers" and "array regions") arranged in the form of an array on an inert substrate material, also referred to herein as a "solid support" or "surface", that allows for combination of the reactants in a sequencing reaction in a defined space and for detection of the sequencing reaction event. A reaction region can be a localized area on the substrate material that facilitates interaction of reactants, e.g., in a nucleic acid sequencing reaction. A reaction region may in certain embodiments be a nanoscale well (also referred to herein as a nanowell), and in further embodiments the nanowell is a ZMW. A nanoscale well typically has dimensions in the nanometer range, i.e., less than 1 micrometer. In some embodiments, a nanoscale well has a cross-sectional diameter of less than 1000, 900, 800, 700, 600, or 500 nm, e.g., less than 400, 350, 300, 250, or 200 nm. In some embodiments, a nanoscale well has a depth of less than 1000, 900, 800, 700, 600, or 500 nm, e.g., less than 400, 350, 300, 250, or 200 nm. As discussed herein, the sequencing reactions contemplated by the invention can in some embodiments occur on numerous individual nucleic acid samples in tandem, in particular simultaneously sequencing numerous nucleic acid samples, e.g., derived from genomic and chromosomal DNA. The apparatus of the invention can therefore include an array having a sufficient number of array regions/reaction regions to carry out such numerous individual sequencing reactions. In one embodiment, the array comprises at least 1,000 reaction regions. In another embodiment, the array comprises greater than 400,000 reaction regions, preferably between 400,000 and 20,000,000 reaction regions. In a more preferred embodiment, the array comprises between 1,000,000 and 16,000,000 reaction regions, e.g., 1,000,000, 2,000,000, 3,000,000, 4,000,000, 5,000,000, 6,000,000, 7,000,000, 8,000,000, 9,000,000, or 10,000,000 reaction regions.

The reaction regions on the array may take the form of a cavity or well in the substrate material, having a width and depth, into which reactants can be deposited. One or more of the reactants typically are bound to the substrate material in the reaction region and the remainder of the reactants are in a medium which facilitates the reaction and which flows through or contacts the reaction region. When formed as cavities or wells, the chambers are preferably of sufficient dimension and order to allow for (i) the introduction of the necessary reactants into the chambers, (ii) reactions to take place within the chamber and (iii) inhibition of mixing of reactants between chambers. The shape of the well or cavity is preferably circular or cylindrical, but can be multisided so as to approximate a circular or cylindrical shape. In another embodiment, the shape of the well or cavity is substantially hexagonal. The cavity can have a smooth wall surface. In an additional embodiment, the cavity can have at least one irregular wall surface. The cavities can have, e.g., a planar bottom or a concave bottom.

The reaction regions may in some situations take the form of a nanopore. Such reaction regions, including arrays of nanopores, are known in the art and described for example in US Published App. Nos. 2013/0327644 and 2014/0051068, which are hereby incorporated by reference in their entirety for all purposes and in particular for all teachings related to nanopore arrays.

Any material can be used as the solid support material, as long as the surface allows for stable attachment of polymerase enzyme complexes and optionally detection of nucleotide incorporation. The solid support material can be planar or can be cavitated, e.g., in a cavitated terminus of a fiber optic or in a microwell etched, molded, or otherwise micromachined into the planar surface, e.g. using techniques commonly used in the construction of microelectromechanical systems. See e.g., Rai-Choudhury, HANDBOOK OF MICROLITHOGRAPHY, MICROMACHINING, AND MICROFABRICATION, VOLUME 1: MICROLITHOGRAPHY, Volume PM39, SPIE Press (1997); Madou, CRC Press (1997), Aoki, Biotech. Histochem. 67: 98-9 (1992); Kane et al., Biomaterials. 20: 2363-76 (1999); Deng et al., Anal. Chem. 72:3176-80 (2000); Zhu et al., Nat. Genet. 26:283-9 (2000). In some embodiments, the solid support is optically transparent, e.g., glass.

Suitable substrates include chips having arrays of nanoscale wells or zero mode waveguides. Exemplary substrates include substrates having a metal or metal oxide layer on a silica-based layer, with nanoscale wells disposed through the metal or metal layer to or into the silica-based layer. Such substrates are described, for example in U.S. patent application Ser. Nos. 10/259,268, 14/187,198, 14/107,730, 13/920,037, and U.S. Pat. Nos. 8,994,946, 8,906,670, 8,993,307, 8,802,600, 7,907,800, and 7,302,146, which are incorporated herein by reference in their entirety for all purposes and in particular for all teachings related to substrates.

EXAMPLES

Figure 14:
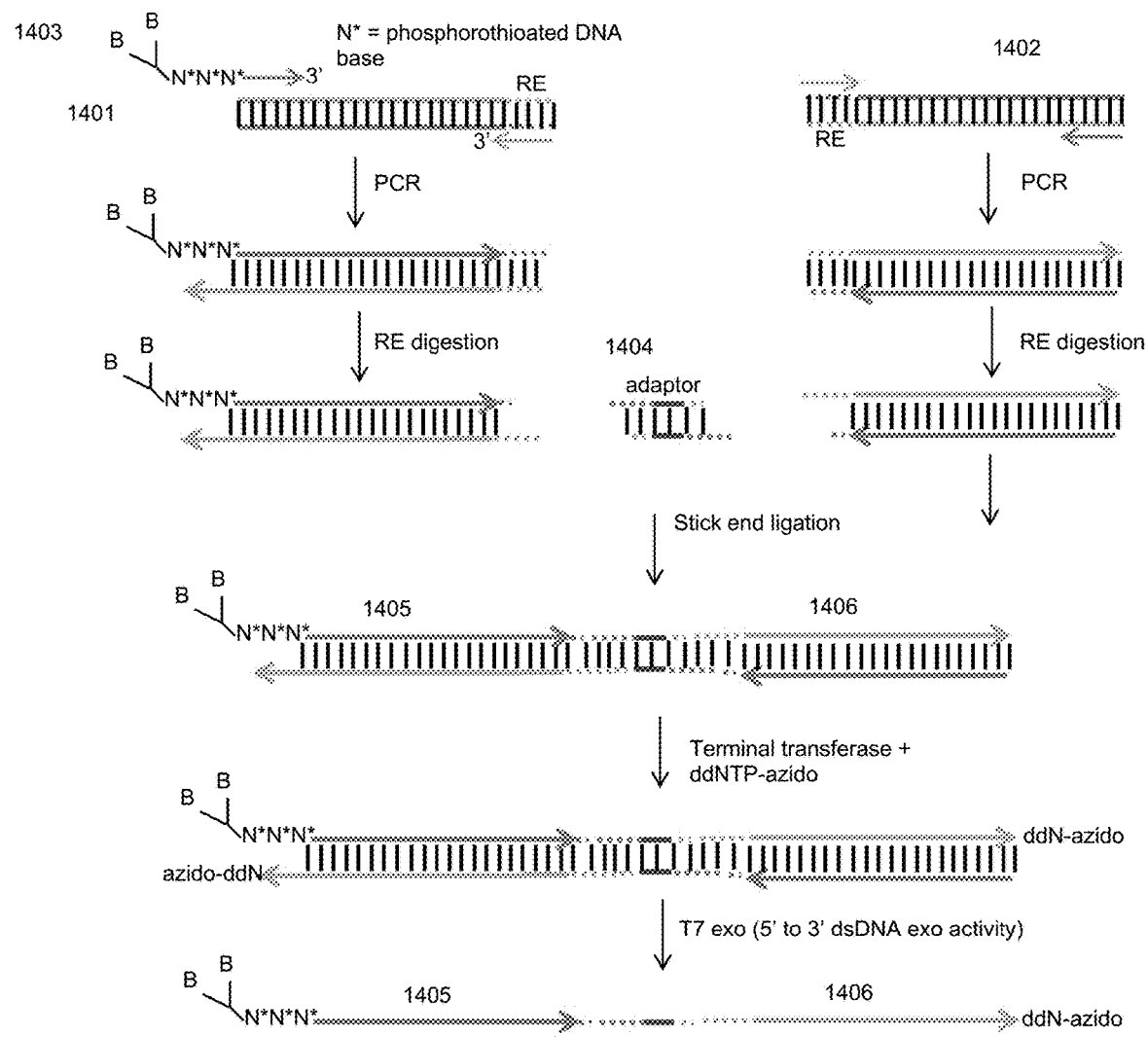
FIG. 14 is a schematic illustration of one embodiment of preparing a tethering nucleic acid reagent for use in helix drive methods described herein.

Example 1: Preparing Tethered Nucleic Acid Reagent for Use in Helix Drive Methods An exemplary route for preparing a tethered nucleic acid for use in the helix drive methods described herein is provided in FIG. 14. As pictured in FIG. 14, two DNA fragments that are mirror images of each other (i.e., the top strand of 1401 is identical to the bottom strand of 1402) are subjected to PCR amplification. 1401 has a biotin containing capture moiety (1403) added to the 5' end of one strand through the PCR reaction. The resultant products are then subjected to restriction endonuclease digestion to create overhangs that are complementary to adaptor 1404. Sticky end ligation joins the two fragments, creating a double stranded nucleic acid where each strand contains self-complementary regions (i.e., region 1405 and 1406 of the top strand are complementary to each other). A terminal transferase reaction adds a ddNTP-azido group to the 3' end of both strands, which can allow for further attachment of moieties for surface attachment. For example, biotin (or another means of immobilizing the tethering nucleic acid on a surface) can be attached via reaction with the azido group. After immobilization of the tether at a desired site and capture of a molecule of interest, the lower strand can then be digested by T7 exonuclease, which has 5' to 3' dsDNA exonuclease activity, leaving the top strand and its capture moiety (and anything that may be attached to the capture moiety, such as a molecule of interest) intact. The two complementary regions 1405 and 1406 would then be free to hybridize to each other to draw the nucleic acid 1408 into a hairpin shape as described in further detail herein.

Figure 15:
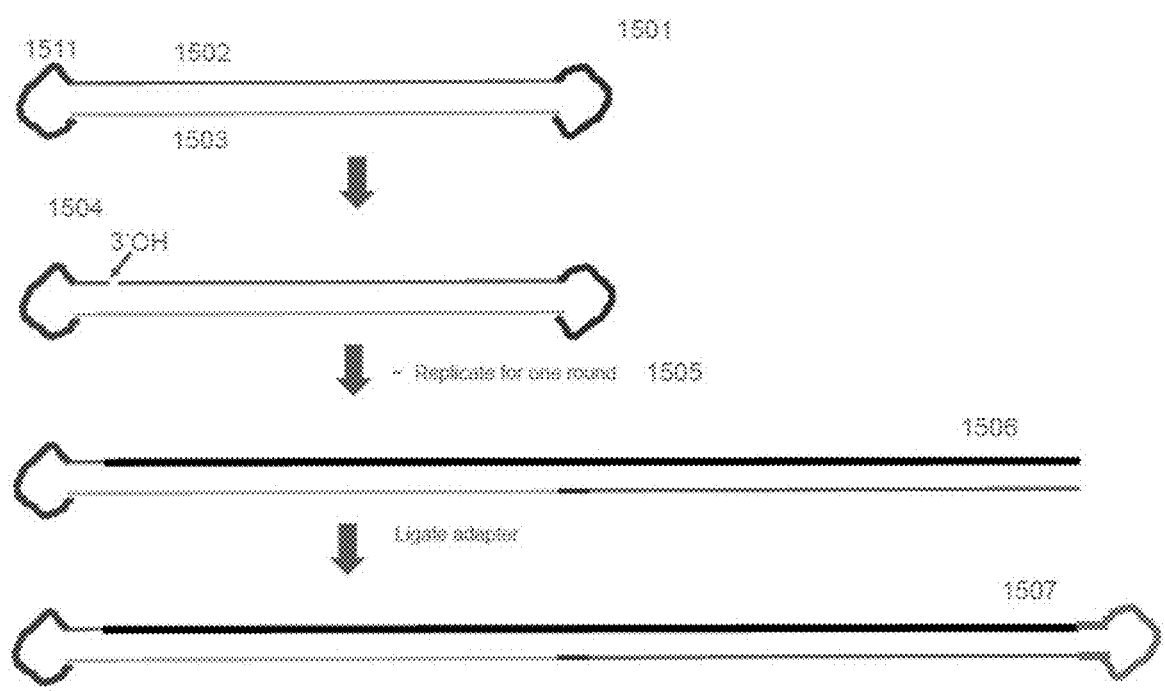
FIG. 15 is a schematic illustration of one embodiment of preparing a tethering nucleic acid reagent for use in helix drive methods described herein.

Another exemplary route for preparing a tethered nucleic acid for use in helix drive methods is provided in FIG. 15. This route produces a partially double stranded, partially single stranded construct that contains long inverted repeat sequences. Starting with the circular construct 1501, the double stranded portion has complementary strands 1502 and 1503. A nick 1504 generated using methods known in the art, including a site-specific nickase or a lyase, results in the circular construct becoming a linear construct that is then replicated for one round (1505) to produce duplex 1506 that now contains an inverted repeat. Optionally, this round of replication is performed with dUTP such that the product strand can be digested later with UDG (uracil-DNA glycosylase) and endonuclease VIII. An adapter 1507 can optionally be ligated to the end of the duplex to produce the double stranded tethering nucleic acid reagent for use in helix drive methods described herein. It will be evident that although adapter 1507 as shown in FIG. 15 is a hairpin, an adapter having a 5' or 3' overhang or blunt ends can also be employed.

As noted, one technique for removing one strand of the double stranded tethering nucleic acid is to incorporate uracil into that strand. Another exemplary technique for removing one strand of the double stranded tethering nucleic acid employs an exonuclease. In this example, construct 1501 includes an exonuclease resistant moiety (e.g., one or more phosphorothioate linkages or a biotin moiety), e.g., in loop 1511. Adapter 1507 can in such an example be a hairpin adapter that includes a nick site; in other embodiments, instead of being a hairpin the adapter is a linear adapter having a free end such that it is subject to exonuclease degradation. (The adapter optionally includes a biotin or other immobilization moiety, e.g., on the other terminus of a linear adapter.) A suitable exonuclease is then employed to digest one strand, starting at the nick in hairpin adapter 1507 or at its free end in embodiments where it is a linear adapter; the exonuclease resistant moiety in loop 1511 can then halt the exonuclease and protect the other strand from degradation.

Figure 16:
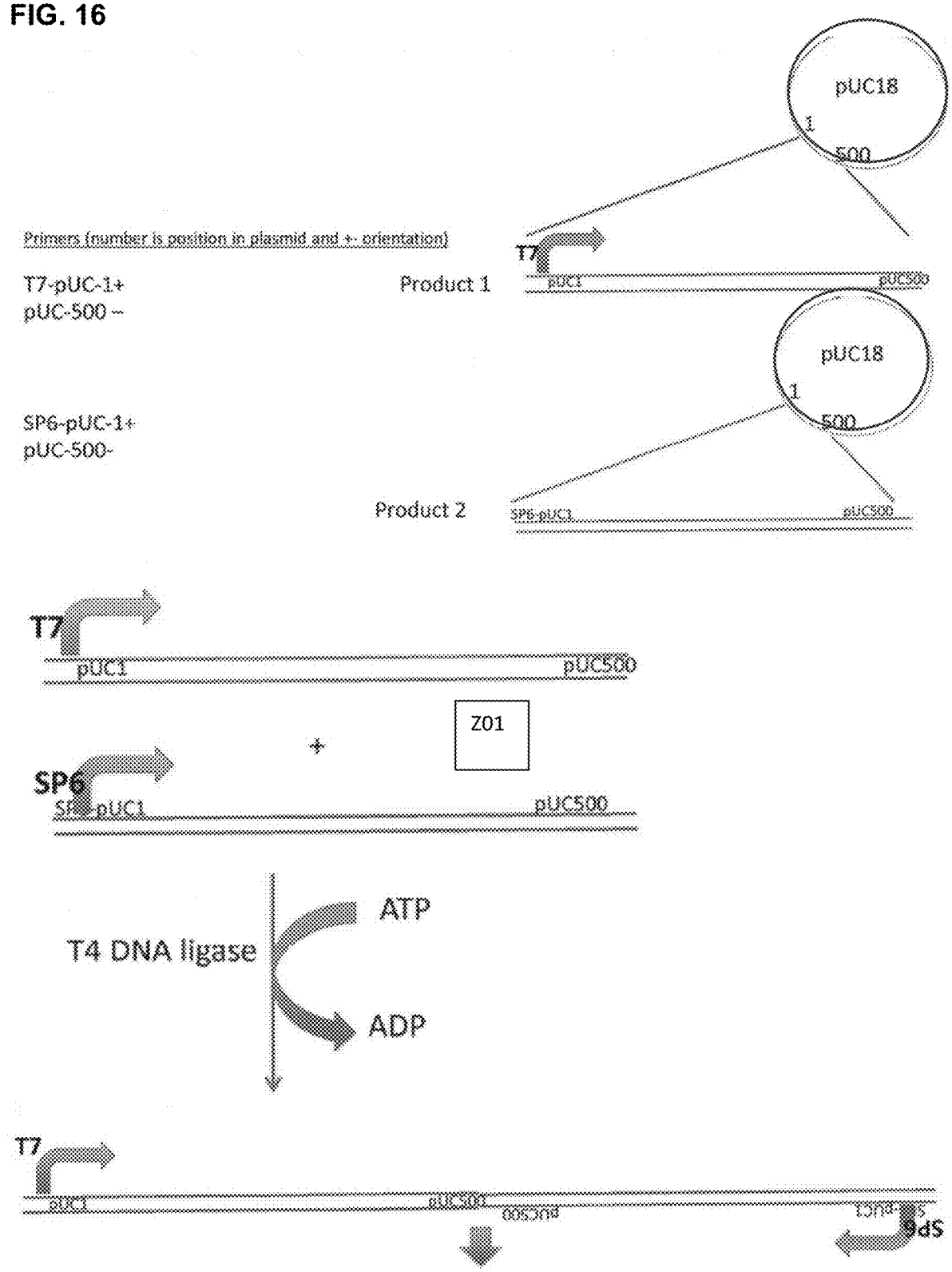
FIG. 16 a schematic illustration of one embodiment of preparing a tethering nucleic acid reagent for use in helix drive methods described herein.

A further method for creating a tethering nucleic acid molecule containing long inverted repeats for use in helix drive methods is to create a long RNA strand that is self-complementary via transcription with a phage polymerase. Long inverted repeats can be difficult to clone into bacteria, and this method thus provides a way to manufacture nucleic acids, particularly DNA/RNA hybrids, containing such long inverted repeats at scale in a test tube. FIG. 16 shows a method in which two separate PCR reactions are performed to create the same approximate product but with T7 and SP6 bacteriophage promoters on opposite ends. The exemplary embodiment shown in FIG. 16 is for creation of a 1 kb RNA/DNA hybrid. The phage polymerases allow the production of a large amount of 50-1000 nt RNA and the short (~20 nt) promoter sequence can be appended onto the 5' end of an oligonucleotide during standard phosphoramidite synthesis. PCR with Taq DNA polymerase synthesis toward the polylinker sequence of pUC18 plasmid (or any other generic non-organismal sequence) is performed. The amplification products can be joined tail to tail to create one transcription cassette for RNA production. In the exemplary embodiment of FIG. 16, the first 500 nt of the RNA is complementary to the 2nd 500 nt. Possible joining strategies include (1) phosphorylation on only one end of each PCR product and then blunt ligation or (2) incorporation of a sticky end restriction site in the PCR primers so that cutting and stitching together is more favorable. In this second method, it may be useful to use non-palindromic sites so that only the correct linkage of product 1+product 2 can form. For either 1 or 2, it can also be beneficial to use pS {phosphorothioate} at the 5' terminal 4 bonds of the T7 primer and the SP6 primer so that only final correct product is protected from T7 exonuclease digestion. The sequence at the junction can be changed by primer choice. The junction determines the nature of the hairpin capping the long RNA helix. Possibilities include a GNRA tetraloop or potentially a larger loop that can favor the single stranded DNA to hybridize to the long single stranded RNA to produce the desired RNA-DNA hybrid.

To produce the DNA strand of the desired RNA/DNA tethering nucleic acid, the transcription cassette can then be used as a template to perform PCR, generally using a thermophilic DNA polymerase. The primers used include a T7 primer and an SP6 primer that has 4×pS (phosphorothioate) bonds at the 5' terminus. ~1000 bp double stranded DNA is purified and digested with T7 exonuclease to completion. The resulting single stranded DNA will fold back on itself and is optionally purified. To produce the RNA strand of the desired RNA/DNA tethering nucleic acid, in vitro transcription of the transcription cassette is performed. High yield kits such as Ambion MegaScript or NEB HiScribe can be used for these methods, as can other techniques involving T7 RNA polymerase. Following transcription, RNase-free DNase I is added to stop the reaction and degrade the template, EDTA is added, and the product is purified by acid phenol chloroform extraction and precipitation with ammonium acetate and ethanol. The RNA is optionally further purified using methods such as LiCl precipitation and column chromatography (G50) and/or native or denaturing urea-PAGE. Biotin groups may further be added using methods known in the art, including use of capping guanosine nucleotides. For example, a capping guanosine nucleotide can be added to the transcript in vitro by a capping enzyme or incorporated as the first nucleotide during transcription. T7 kits that incorporate a cap are commercially available. Periodate oxidation can then be used to create a cis-diol at both the cap and the 3' end of the RNA. This diol is unstable and resolves to dual aldehydes. The aldehyde can then be reacted with a biotin-hydrazide (several are commercially available, e.g., Pierce EZ-Link). As another example, a synthetic guanosine cap with a specific reactive moiety (e.g., azide for click chemistry) can be added to the transcript. Biotin can then be added through an appropriate reaction.

In a further example for creating a tethering nucleic acid, the tethering nucleic acid is a double stranded nucleic acid that has a tag on both ends of a single strand of the duplex. The strand without the tags is then selectively digested and the self-complementary base pairing of the remaining strand causes the strand to fold onto itself and thereby bring any attached molecules down to the reaction site with it, as is discussed in further detail herein above. One method to create such a tagged molecule is to amplify a double stranded DNA molecule using a sense and an anti-sense primer designed for these purposes. The sense primer is designed to have an attachment group at the 5' end (a bisbiotin tag for example). The sequence of the sense primer further includes a recognition site for a nickase that will nick the opposing strand a few bases upstream from the 3' end. The primer may also contain phosphorothioate or methylphosphonate groups to protect against degradation. The antisense primer can be designed to contain a site at the 5' end that can be removed but will still leave a 5' phosphate. This could incorporate a dU for USER excision or a ribo base for RNase or the same nick site as the other primer, as long as it leaves a 5' phosphate. The fragment produced by PCR amplification with these primers can be treated with terminal deoxynucleotidyl transferase and a dideoxy nucleotide that has the attachment group. This will attach one of the attachment nucleotides to each 3' end. This is followed by treatment with the nickase (and/or USER/RNase) whose sequence was designed into the primers. This will create both a 5' and 3' overhang on the sense strand and leave a 5' phosphate on the antisense strand and remove the antisense strand attachment tag. The nicked off bases can be easily removed while the main duplex stays bound together. The double stranded duplex is now ready to be loaded into the reaction site (e.g., ZMW) to capture molecules of interest such as active sequencing complexes. Once the complexes have been captured, the non-tagged strand can be removed by a combination of exonucleases. Designing the ssDNA to fold onto itself will ensure that the complex is rapidly brought to the bottom of the ZMW. Lambda exonuclease preferentially degrades dsDNA to ssDNA in a 5'->3' if there is a 5' phosphate. The 5' P on the antisense strand will target it for degradation and the lack of phosphate (and/or the presence of phosphorothioates and methylphosphonates) on the 5' end of the sense strand will protect it from degradation. The lack of a 5' phosphate on the sequencing primer will also protect it if present. Another option is to use Exonuclease III, which preferentially degrades one strand of dsDNA in a 3'->5' direction only if there is a blunt end or a 5' overhang. The recessed 3' end of the antisense strand will target it for degradation and the 3' overhang (>4 bases) of the sense strand will protect it from degradation. The polymerase over the 3' end of the primer should protect it from degradation. Polarity of the double stranded DNA can be designed, for example, by using different tags (attachment chemistries) at each end.

Example 2: Preparing Tethered Nucleic Acid Reagent for Use in Guidewire Methods

Figure 17:
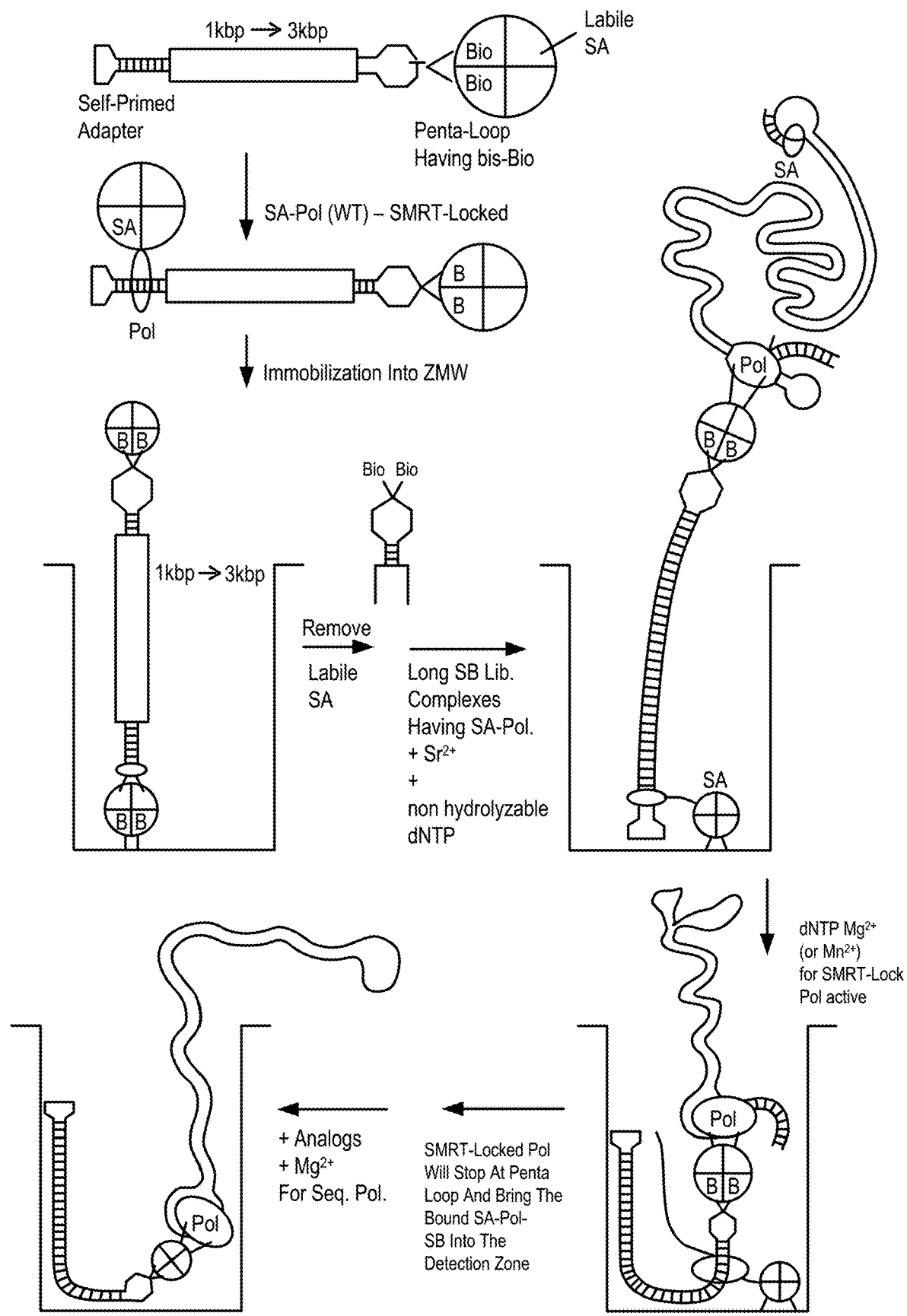
FIG. 17 is a schematic illustration of a loading method that utilizes guidewire mechanisms.

An exemplary route for preparing a tethered nucleic acid and using it in accordance with guidewire methods described herein is schematically illustrated in FIG. 17. This guidewire molecule is generally used to load complexes into deep nanoscale wells. An exemplary DNA molecule acting as a tether has a self-primed adapter (SP) at one end and an amino-adapter at the other end which can be converted into bis-biotins (or clusters of biotins for even more efficient capture). The bis-biotins can be protected by a labile streptavidin (SA) (or bisbiotins can be added later to the amino-adapter). The tether DNA is allowed to complex at the SP-adapter with a strand-displacing SA-polymerase (Pol) (e.g., wild type Phi29 Pol-SA, which does not use nucleotide analogs having six phosphate groups (dN6P) for incorporation). This Pol is then locked onto the tethering DNA, e.g., through reaction of a chemical cross-linker as detailed herein above. This SP-DNA-Pol-SA complex is immobilized at ZMW bottom through SA-biotin interaction. The locked Pol on the SP-adapter is at the bottom of ZMW while the other DNA end having amino-adapter reaches outside of the ZMW or near the entrance. If the amino-adapter was converted into bis-biotins by "click-chemistry" in advance and protected by a labile SA then dissociation of the labile SA from bis-biotins frees the biotins to interact. For example, a native (non-labile) SA bound to a polymerase complexed with a sequencing template (e.g., a large SMRTbell™) could compete with this labile SA. This second polymerase, which will be employed in sequencing, can be stalled as described above, e.g., using non-hydrolyzable dN6P. After capture of the long SMRTbell™-Pol-SA complexes by the bisbiotins at the end of the tether DNA, the immobilized locked WT Pol, binding at the SP adapter of the tether DNA, can start replication when Mg/dNTP is added (+non-hydrolyzable dN6P to maintain the sequencing polymerase in a stalled state). The replication action of this immobilized WT Phi29 Pol, pulling the template through the immobilized Pol, allows the amino-adapter end to move down to the bottom of ZMW and pulls the captured stalled SA-Pol-SMRTbell™ complex toward the bottom of ZMW. The locked WT Pol will stop pulling the tethering DNA further when it hits the bisbiotins-SA-Pol-long SMRTbell™ complex. At this time, the bisbiotin-captured SA-Pol-long SMRTbell™ complex is in the detection zone at the bottom of the ZMW. The detectable incorporation of labeled dN6P analogs during replication of this captured SA-sequencing Pol can now produce sequencing information for the long SMRTbell™.

Figure 4:
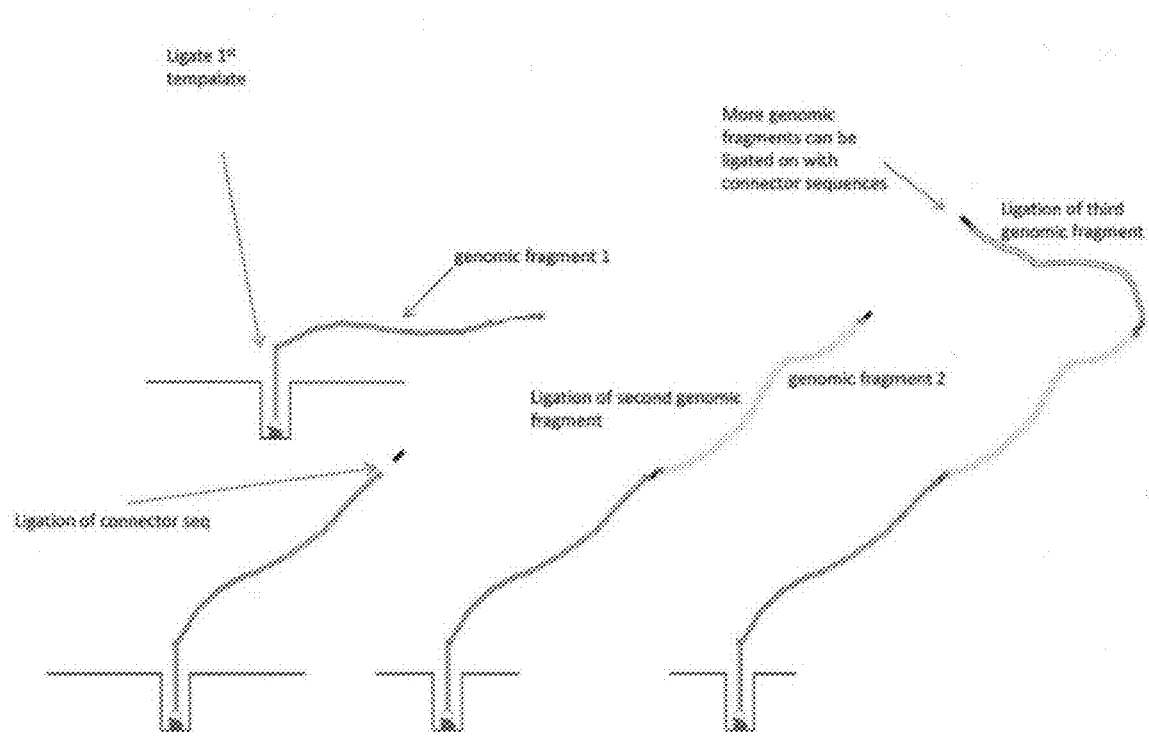
FIG. 4 is a schematic illustration of a loading method that utilizes winching mechanisms and concatemers of template sequences.

Example 3: Preparing Tethered Nucleic Acid Reagent for Use in Winching/Fishing Methods An exemplary route for preparing a tethered nucleic acid for use in Winching/Fishing methods described herein includes the following work flow:
(1) Create the fishing/winching sequence by:
PCR reaction of a 1-2 kb template with a blunt end restriction site near one end;
add SmrtBell™ hairpins
clean up SmrtBell™
restriction digest to take one hairpin off to expose sticky end (although these methods will work with blunt ends as well)
ligate on sticky overhang or use existing sticky overhang
clean up one hairpin with overhang template
anneal primer
bind polymerase with excess template to polymerase which increases the cleanliness of the subsequent sequencing
to the primed hairpin add nucleotide lock or covalent polymerase locking domain or even biotin lock
(2) Create Template molecules by:
Shear to appropriate size
Optional cleanup of fragments
Ligate sticky ends compatible with the fishing/winching template sticky ends (or with optional connector sequence)
Size selection
Clean up ligated sticky ended templates
(3) Optionally create connector sequence (e.g., about 50-200 bp) with same sticky ends as on the fishing/winching sequence
(4) Load fishing/winching sequence into ZMW by diffusion loading
(5) Add the template molecules to the loaded ZMW chip plus ligation mix of choice and ligate the templates to the preloaded fishing/winching sequences; optionally add the connector sequences to make concatemers of templates separated by identifiable connectors
(6) After ligation time, wash the chip and load with sequencing mix, hot start and start observation. Initial sequence will be the fishing/winching template which will pull the ligated template molecule into the ZMW and yield the sequence; optionally one could further observe a connecter sequence followed by additional template and connectors (see FIG. 4).

The present specification provides a complete description of the methodologies, systems and/or structures and uses thereof in example aspects of the presently-described technology. Although various aspects of this technology have been described above with a certain degree of particularity, or with reference to one or more individual aspects, those skilled in the art could make numerous alterations to the disclosed aspects without departing from the spirit or scope of the technology hereof. Since many aspects can be made without departing from the spirit and scope of the presently described technology, the appropriate scope resides in the claims hereinafter appended. Other aspects are therefore contemplated. Furthermore, it should be understood that any operations may be performed in any order, unless explicitly claimed otherwise or a specific order is inherently necessitated by the claim language. It is intended that all matter contained in the above description shall be interpreted as illustrative only of particular aspects and are not limiting to the embodiments shown. Unless otherwise clear from the context or expressly stated, any concentration values provided herein are generally given in terms of admixture values or percentages without regard to any conversion that occurs upon or following addition of the particular component of the mixture. To the extent not already expressly incorporated herein, all published references and patent documents referred to in this disclosure are incorporated herein by reference in their entirety for all purposes. Changes in detail or structure may be made without departing from the basic elements of the present technology as defined in the following claims.

What is claimed:

1. A method of delivering polymerase enzyme complexes to nanoscale wells, the method comprising:
    (a) providing a substrate comprising an array of nanoscale wells;
    (b) coating the top surface of the substrate between the nanoscale wells with a positively charged molecule to form a coated surface;
    (c) applying a composition comprising polymerase enzyme complexes to the coated surface such that at least a portion of the polymerase enzyme complexes attach to the positively charged molecules, wherein the polymerase enzyme complexes comprise template nucleic acids complexed with polymerase enzymes; and
    (d) after step c), releasing the polymerase enzyme complexes from the positively charged molecules to allow the polymerase enzyme complexes to passively diffuse into the nanoscale wells,
thereby delivering polymerase enzyme complexes to the nanoscale wells.

2. The method of claim 1, wherein releasing the polymerase enzyme complexes from the positively charged molecules comprises releasing the polymerase enzyme complexes from the positively charged molecules by applying a solution containing high salt to the coated surface.

3. The method of claim 1, wherein the releasing step comprises applying a size exclusion resin to the coated surface.

4. The method of claim 1, wherein the template nucleic acid molecules are further hybridized to a primer.

5. The method of claim 1, wherein the template nucleic acid molecules are at least 5 kb long.

6. The method of claim 1, wherein the template nucleic acid molecules are about 3 kb to about 20 kb in length.

7. The method of claim 1, wherein the delivering of the polymerase enzyme complexes is accomplished about 4 to about 100 times faster than seen when the surface is not coated with the positively charged molecule.

8. The method of claim 1, wherein the delivering of the polymerase enzyme complexes is accomplished at least 30, 40, 50, 60, 70 or 80 times faster than seen when the surface is not coated with the positively charged molecule.

9. The method of claim 1, wherein the delivering of the polymerase enzyme complexes is accomplished about 30 to about 150 times faster than seen when the surface is not coated with the positively charged molecule.

10. The method of claim 1, wherein the delivering of the polymerase enzyme complexes is accomplished about 20 to about 80 times faster than seen when the surface is not coated with the positively charged molecule.

11. The method of claim 1, wherein the positively charged molecule is a positively charged peptide or polypeptide.

12. The method of claim 11, wherein releasing the polymerase enzyme complexes from the positively charged molecules comprises releasing the polymerase enzyme complexes from the positively charged molecules by applying a protease to the coated surface.

13. The method of claim 12, wherein the protease comprises trypsin.

14. The method of claim 11, wherein the positively charged peptide or polypeptide is a member selected from the group consisting of Tat, poly-lysine, poly-arginine, and histone.

15. The method of claim 11, wherein the positively charged peptide or polypeptide comprises a Tat peptide.

16. The method of claim 1, wherein the positively charged molecule is a cationic polymer.

17. The method of claim 1, wherein the base of the nanoscale well comprises biotin and wherein the polymerase enzyme comprises a biotin-binding moiety, the method comprising, after the releasing step, localizing the polymerase enzyme complexes to the base of the nanoscale wells through binding of the biotin-binding moiety on the polymerase to the biotin on the base of the nanoscale well.

18. The method of claim 1, wherein the base of the nanoscale well comprises a biotin-binding moiety and wherein the polymerase enzyme comprises biotin, the method comprising, after the releasing step, localizing the polymerase enzyme complexes to the base of the nanoscale wells through binding of the biotin on the polymerase to the biotin-binding moiety on the base of the nanoscale well.

19. The method of claim 1, wherein the substrate comprises a metal or metal oxide layer on a silica-based layer, wherein the nanoscale wells are disposed through the metal or metal oxide layer to or into the silica-based layer.

20. The method of claim 1, wherein the top surface of the substrate between the nanoscale wells comprises aluminum or titanium nitride.

* * * * *